US010202396B2

(12) United States Patent
Gebbie et al.

(10) Patent No.: US 10,202,396 B2
(45) Date of Patent: Feb. 12, 2019

(54) PROCESS FOR IMPROVED OPIOID SYNTHESIS

(71) Applicant: RHODES TECHNOLOGIES, Coventry, RI (US)

(72) Inventors: Stuart James Gebbie, Norwood, MA (US); Joshua R. Giguere, Sharon, MA (US); Keith McCarthy, Old Lyme, CT (US); Lonn S. Rider, Foster, RI (US)

(73) Assignee: RHODES TECHNOLOGIES, Coventry, RI (US)

( * ) Notice: Subject to any disclaimer, the term of this patent is extended or adjusted under 35 U.S.C. 154(b) by 0 days.

(21) Appl. No.: 15/700,345

(22) Filed: Sep. 11, 2017

(65) Prior Publication Data
US 2018/0111946 A1    Apr. 26, 2018

Related U.S. Application Data

(62) Division of application No. 14/413,360, filed as application No. PCT/IB2013/001538 on Jul. 15, 2013, now abandoned.

(60) Provisional application No. 61/762,657, filed on Feb. 8, 2013, provisional application No. 61/672,265, filed on Jul. 16, 2012.

(51) Int. Cl.
*C07D 489/08* (2006.01)
*A61K 31/485* (2006.01)

(52) U.S. Cl.
CPC .................. *C07D 489/08* (2013.01)

(58) Field of Classification Search
CPC .......................... C07D 489/08; A61K 31/485
USPC ............................................. 546/45; 514/282
See application file for complete search history.

(56) References Cited

U.S. PATENT DOCUMENTS

| | | | |
|---|---|---|---|
| 2,772,270 A | 11/1956 | Weiss et al. | |
| 3,133,132 A | 5/1964 | Loeb et al. | |
| 3,173,876 A | 3/1965 | Zobrist | |
| 3,276,586 A | 10/1966 | Rosaen | |
| 3,541,005 A | 11/1970 | Strathmann et al. | |
| 3,541,006 A | 11/1970 | Bixler et al. | |
| 3,546,876 A | 12/1970 | Fokker et al. | |
| 3,845,770 A | 11/1974 | Theeuwes et al. | |
| 3,916,899 A | 11/1975 | Theeuwes et al. | |
| 4,063,064 A | 12/1977 | Saunders et al. | |
| 4,088,864 A | 5/1978 | Theeuwes et al. | |
| 4,160,020 A | 7/1979 | Ayer et al. | |
| 4,200,098 A | 4/1980 | Ayer et al. | |
| 4,285,987 A | 8/1981 | Ayer et al. | |
| 4,861,598 A | 8/1989 | Oshlack | |
| 4,957,681 A | 9/1990 | Klimesch et al. | |
| 5,215,758 A | 6/1993 | Krishnamurthy | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,356,467 A | 10/1994 | Oshlack et al. | |
| 5,472,712 A | 12/1995 | Oshlack et al. | |
| 8,846,923 B1 | 9/2014 | Itov et al. | |
| 9,060,620 B1 | 6/2015 | Patel | |
| 9,062,062 B1 | 6/2015 | Itov et al. | |
| 9,090,620 B2 | 7/2015 | Itov et al. | |
| 9,108,976 B2 | 8/2015 | Itov et al. | |
| 9,233,972 B2 | 1/2016 | Itov et al. | |
| 9,309,257 B2 | 4/2016 | Itov et al. | |
| 9,932,348 B2 | 4/2018 | Giguere et al. | |
| 9,938,285 B2 | 4/2018 | Giguere et al. | |
| 2005/0038251 A1 | 2/2005 | Francis et al. | |
| 2006/0111383 A1 | 5/2006 | Casner et al. | |
| 2007/0088162 A1 | 4/2007 | Snuparek et al. | |
| 2007/0117286 A1 | 5/2007 | Jang et al. | |
| 2007/0117826 A1 | 5/2007 | Janjikhel et al. | |
| 2010/0048905 A1 | 2/2010 | Wang et al. | |
| 2010/0324338 A1 | 12/2010 | Maeda et al. | |
| 2013/0253228 A1 | 9/2013 | Tsuda et al. | |
| 2015/0166552 A1 | 6/2015 | Itov et al. | |
| 2015/0166554 A1 | 6/2015 | Itov et al. | |
| 2015/0166556 A1 | 6/2015 | Itov et al. | |
| 2015/0166557 A1 | 6/2015 | Itov et al. | |
| 2015/0259355 A1 | 9/2015 | Gebbie et al. | |
| 2015/0315203 A1 | 11/2015 | Gebbie et al. | |
| 2017/0022209 A1 | 1/2017 | Giguere et al. | |
| 2017/0022210 A1 | 1/2017 | Giguere et al. | |

FOREIGN PATENT DOCUMENTS

| | | |
|---|---|---|
| CA | 2 610 859 A1 | 12/2006 |
| CN | 101198612 A | 6/2008 |
| CN | 103113378 A | 5/2013 |
| CN | 103433076 A | 12/2013 |
| WO | WO 03/007802 A2 | 1/2003 |

(Continued)

OTHER PUBLICATIONS

King, R.E., "Chapter 89: Tablets, Capsules, and Pills," in *Remington's Pharmaceutical Sciences*, Arthur Osol, ed., pp. 1553-1584, Mack Publishing Company, United States (1980).

Robinson, M.J., "Chapter 90: Coating of Pharmaceutical Dosage Forms," in *Remington's Pharmaceutical Sciences*, Arthur Osol, ed., pp. 1585-1593, Mack Publishing Company, United States (1980).

Seher, A. and Lange, J., "Gemeinschaftsarbeiten der DGF, 60. Mitteilung, Deutsche Einheitsmethoden zur Untersuchung von Fetten, Fettprodukten und verwandten Stoffen, 45. Mitt.: Analyse von Wachsen und Wachsprodukten X," *Fette, Seifen, Anstrichmittel* 76(3):135, Wiley-VCH Verlag GmbH & Co., Germany (1974).

Weiss, U., "Derivatives of Morphine. II. Demethylation of 14-hydroxycodeinone. 14-Hydroxymorphinone and 8,14-Dihydroxydihydromorphinone," *J. Org. Chem.* 22(11):1505-1508, American Chemical Society, United States (1957).

(Continued)

*Primary Examiner* — Charanjit Aulakh
(74) *Attorney, Agent, or Firm* — Sterne, Kessler, Goldstein & Fox P.L.L.C.

(57) ABSTRACT

Compounds and compositions for use as starting materials or intermediate materials in the preparation of opioids including, e.g., oxycodone base and/or an oxycodone salt; processes for preparing these compounds and compositions; uses of these compounds and compositions in the preparation of APIs and pharmaceutical dosage forms; and uses of said APIs and pharmaceutical dosage forms in the treatment of medical conditions.

29 Claims, No Drawings

(56) References Cited

FOREIGN PATENT DOCUMENTS

| WO | WO 2005/097801 A1 | 10/2005 |
|---|---|---|
| WO | WO 2006/019364 A1 | 2/2006 |
| WO | WO 2006/091885 A2 | 8/2006 |
| WO | WO 2008/070656 A2 | 6/2008 |
| WO | WO 2008/070658 A1 | 6/2008 |
| WO | WO 2008/072018 A1 | 6/2008 |
| WO | WO 2008/118654 A1 | 10/2008 |
| WO | WO 2008/130553 A1 | 10/2008 |
| WO | WO 2011/032214 A1 | 3/2011 |
| WO | WO 2011/117172 A1 | 9/2011 |
| WO | WO 2011/154826 A1 | 12/2011 |
| WO | WO 2012/003468 A1 | 1/2012 |
| WO | WO 2012/005795 A1 | 1/2012 |
| WO | WO 2013/188418 A1 | 12/2013 |
| WO | WO 2014/013313 A1 | 1/2014 |
| WO | WO 2015/095585 A2 | 6/2015 |

OTHER PUBLICATIONS

Yang, J.W., et al., "A Metal-Free Transfer Hydrogenation: Organocatalytic Conjugate Reduction of α,β-Unsaturated Aldehydes," *Angew. Chem. Int. Ed. Engl.* 43(48):6660-6662, Wiley-VCH Verlag GmbH & Co., Germany (2004).

International Search Report for International Patent Application No. PCT/IB2013/001538, European Patent Office, Rijswijk, Netherlands, dated Nov. 19, 2013.

International Preliminary Report on Patentability and Written Opinion for International Patent Application No. PCT/IB2013/001538, WIPO, Geneva, Switzerland, dated Jan. 20, 2015.

Devi, R.B., et al., "Domino alkylation/oxa-Michael of 1,3-cyclohexanediones: Steering the C/O-chemoselectivity to reach tetrahydrobenzofuranones," *Organic & Biomolecular Chemistry* 9(19):6509-6512, The Royal Society of Chemistry, England (2011).

English language Abstract of Chinese Patent Publication No. CN 103113378 A, Espacenet database—Worldwide, European Patent Office (listed as document FP16 on the accompanying form PTO/SB/08A) (2013).

English language Abstract of Chinese Patent Publication No. CN 103433076 A, Espacenet database—Worldwide, European Patent Office (listed as document FP18 on the accompanying form PTO/SB/08A) (2013).

Hale, M.E., et al., "Efficacy and Safety of OPANA ER (Oxymorphone Extended Release) for Relief of Moderate to Severe Chronic Low Back Pain in Opioid-Experienced Patients: A 12-Week, Randomized, Double-blind, Placebo-controlled Study," *The Journal of Pain* 8(2):175-184, American Pain Society, United States (2007).

Haynes, D.A., et al., "Occurrence of Pharmaceutically Acceptable Anions and Cations in the Cambridge Structural Database," *Journal of Pharmaceutical Sciences* 94(10):2111-2120, Wiley-Liss, Inc., United States (2005).

International Preliminary Report on Patentability for International Application No. PCT/IB2015/050294, WIPO, Geneva, Switzerland, dated Jul. 19, 2016, 7 pages.

International Preliminary Report on Patentability for International Application No. PCT/IB2015/050295, WIPO, Geneva, Switzerland, dated Jul. 19, 2016, 7 pages.

International Search Report and Written Opinion for International Application No. PCT/IB2015/050294, European Patent Office, Netherlands, dated Mar. 16, 2015, 10 pages.

International Search Report and Written Opinion for International Application No. PCT/IB2015/050295, European Patent Office, Netherlands, dated Mar. 16, 2015, 10 pages.

Liu, M-Q., et al., "Synthesis of Long-Acting Analgetic Hydrazone Derivatives of 14-Hydroxycodeinone and 14-Hydroxymorphinone," *Acta Pharmaceutica Sinica* 18(6):475-477, China Academic Journal Electronic Publishing House, China (1983).

Maxwell, G.M., "The Central Nervous System," in *Principles of Paediatric Pharmacology*, Maxwell, G.M., ed., p. 126, Oxford University Press, England (1984).

Office Action dated Dec. 22, 2015, in U.S. Appl. No. 14/413,360, Gebbie et al., having a 35 U.S.C. § 371(c) date of Jan. 7, 2015.

Office Action dated Jul. 12, 2017, in U.S. Appl. No. 14/413,362, Gebbie et al., having a 35 U.S.C. § 371(c) date of Jan. 7, 2015.

Office Action dated Jul. 6, 2016, in U.S. Appl. No. 14/413,360, Gebbie et al., having a 35 U.S.C. § 371(c) date of Jan. 7, 2015.

Office Action dated Jun. 12, 2017, in U.S. Appl. No. 14/413,360, Gebbie et al., having a 35 U.S.C. § 371(c) date of Jan. 7, 2015.

Office Action dated Jun. 20, 2017, in U.S. Appl. No. 15/110,824, Giguere et al., having a 35 U.S.C. § 371(c) date of Jul. 11, 2016.

Office Action dated May 30, 2017, in U.S. Appl. No. 15/110,825, Giguere et al., having a 35 U.S.C. § 371(c) date of Jul. 11, 2016.

Sevillano, L.G., et al., "Synthesis of B,B-dinor-B-secosteroids as potential cardenolide analogues," Tetrahedron 58:10103-10112, Elsevier Science Ltd., England (2002).

The United States Pharmacopeial Convention, "USP 34-NF 29, First Supplement, Monograph on Oxycodone Hydrochloride," p. 5016 (Aug. 1, 2011).

Watson, C.P.N., et al., "Controlled-release oxycodone relieves neuropathic pain: a randomized controlled trial in painful diabetic neuropathy," Pain 105(1-2):71-78, Elsevier Science B.V., Netherlands (2003).

Zhang, B. et al., "Oxycodone Hydrochloride," Chinese Journal ofMedicinal Chemistry 21(2):166, China Academic Journal Electronic Publishing House, China (2011).

Notice of Allowance dated Nov. 22, 2017 in U.S. Appl. No. 15/110,825, Giguere., et al., filed Jul. 11, 2016, 5 pages.

Notice of Allowance dated Nov. 30, 2017 in U.S. Appl. No. 15/110,824, Giguere., et al., filed Jul. 11, 2016, 6 pages.

International Search Report for International Patent Application No. PCT/IB2013/001541, European Patent Office, Rijswijk, Netherlands, dated May 12, 2013, 7 pages.

International Preliminary Report on Patentability and Written Opinion for International Patent Application No. PCT/IB2013/001541, WIPO, Geneva, Switzerland, dated Jan. 20, 2015, 15 pages.

Office Action dated May 31, 2018, in U.S. Appl. No. 14/413,362, Gebbie et al., having a 35 U.S.C. § 371(c) date of Jan. 7, 2015.

Grant, Roger L., Grant & Hackh's Chemical Dictionary, p. 148, 5th Ed., McGraw-Hill, Inc., United States of America (1987).

An English language translation of CN 103113378 A (cited as document FP16 in the Fourth Supplemental IDS filed on Mar. 26, 2018), Google translate, Aug. 28, 2018.

An English language translation of CN 103433076 A (cited as document FP17 in the Fourth Supplemental IDS filed on Mar. 26, 2018), Google translate, Aug. 28, 2018.

Kok, G.B. and Scammells, P.J., "Improved synthesis 14-hydroxy opioid pharmaceuticals and intermediates," *RSC Advances* 2(30):11318-11325, The Royal Society of Chemistry, England (Oct. 2012).

Office Action dated Jan. 4, 2017 in U.S. Appl. No. 14/413,362, Gebbie, S.J., et al., § 371(c) Date Jan. 7, 2015.

PROCESS FOR IMPROVED OPIOID SYNTHESIS

The present invention is in the field of pharmaceutical compositions comprising opioids and in the field of pharmaceutical opioid synthesis. It provides compounds and compositions for use as starting materials or intermediate materials in the preparation of opioids including, e.g., oxycodone base and/or an oxycodone salt; processes for preparing these compounds and compositions; uses of these compounds and compositions in the preparation of APIs and pharmaceutical dosage forms; and uses of said APIs and pharmaceutical dosage forms in the treatment of medical conditions.

BACKGROUND OF THE INVENTION

Opioids like oxycodone and its hydrochloride salt have long been used as analgesics.

Typically, oxycodone base is prepared by oxidation of thebaine to 14-hydroxycodeinone, and reducing the 14-hydroxycodeinone to oxycodone base. A conventional route for the preparation of oxycodone via oxidation of thebaine to 14-hydroxycodeinone is illustrated in Scheme 1:

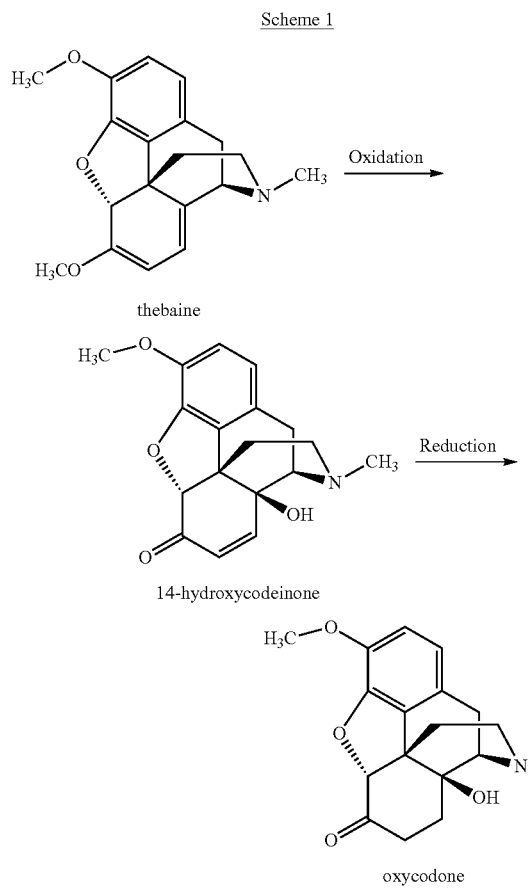

Once the oxycodone base has been prepared, it is usually reacted with an acid to produce an oxycodone salt, typically oxycodone hydrochloride, as shown below in Scheme 2:

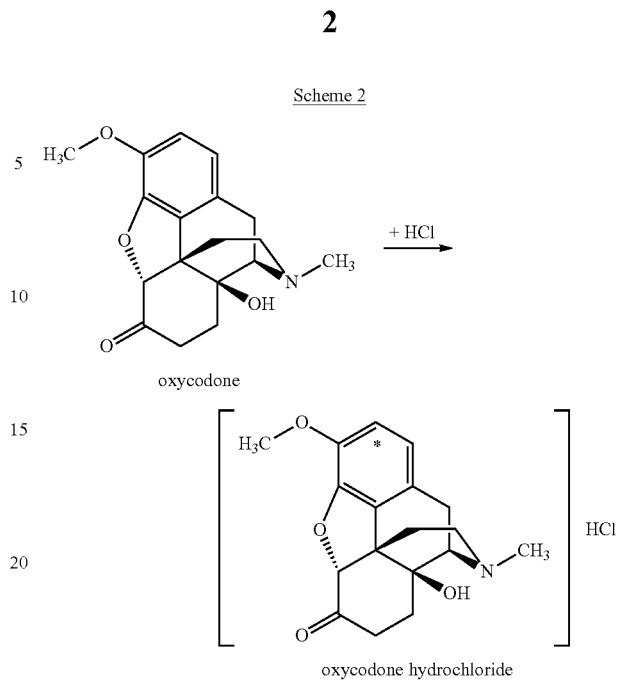

The oxidation step in the synthetic route illustrated in Scheme 1 can yield by-products which may be converted into other by-products during further conversion of the oxidation product (e.g., during the reaction shown in Scheme 2) or may be carried over into the final opioid compound, final pharmaceutical composition or final dosage form. These by-products may be undesired in the final pharmaceutical composition or final dosage form. Separation of these by-products from the final opioid may often be difficult, time-consuming and not volume efficient (e.g., if a separation by HPLC is required).

For example, during oxidation of thebaine to 14-hydroxycodeinone, certain by-products can be formed, e.g., 8-hydroxyoxycodone. 8-Hydroxyoxycodone can have two stereoconfigurations, 8α-hydroxyoxycodone (8-alpha-hydroxyoxycodone) and 8β-hydroxyoxycodone (8-beta-hydroxyoxycodone). It is known from the prior art that 8α-hydroxyoxycodone can convert to 14-hydroxycodeinone under acidic conditions (e.g., when HCl is added) (WO 2005/097801 to Chapman et al.). It is further known that, under harsher reaction conditions, 8β-hydroxyoxycodone can also convert to 14-hydroxycodeinone (Weiss U., J. Org. Chem. 22 (1957), pp. 1505 to 1508). These conversions described in the art are illustrated in Schemes 3 and 4:

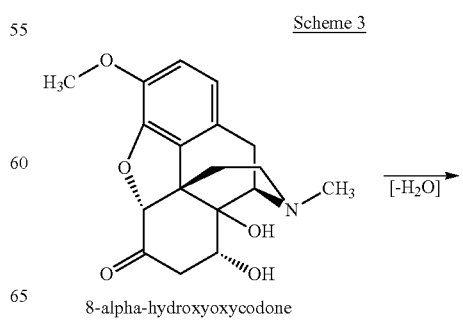

-continued

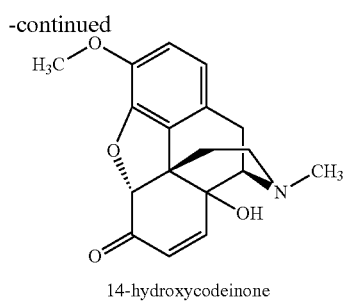
14-hydroxycodeinone

Scheme 4

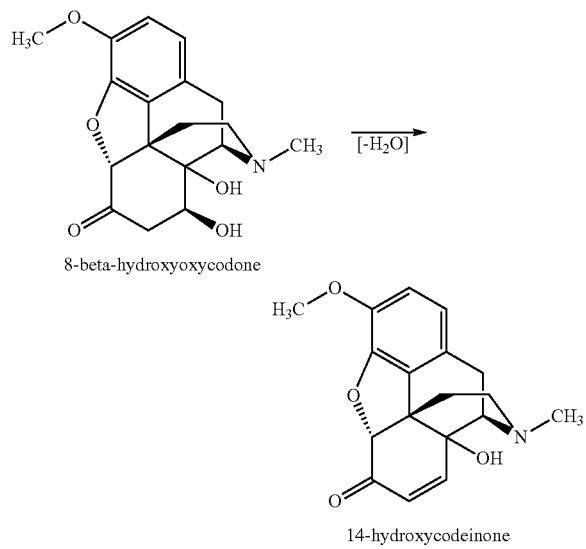

Thus, the 14-hydroxycodeinone intermediate shown in Scheme 1 is not only the immediate precursor to oxycodone, it is also often found in the final oxycodone salt used in pharmaceutical compositions, e.g., 14-hydroxycodeinone derived from 8α-hydroxyoxycodone is found in oxycodone hydrochloride. Some regulatory authorities do not approve a pharmaceutical composition or dosage form for use and sale to the public if the amount of 14-hydroxycodeinone in the pharmaceutical composition or dosage form exceeds the amount set by these authorities. The reason for this is that 14-hydroxycodeinone belongs to a class of compounds known as α,β-unsaturated ketones (ABUKs). These compounds contain a substructural component (the α,β-unsaturated ketone component) which produces a structure-activity relationship alert for genotoxicity. The United States Food and Drug Administration ("FDA") currently requires that, in order to obtain approval to market single-entity oxycodone HCl products, applicants must limit the level of ABUKs in oxycodone hydrochloride to NMT 10 ppm (not more than 10 ppm) of the oxycodone hydrochloride. The amount of 14-hydroxycodeinone in the oxycodone hydrochloride first obtained from a conventional reaction of thebaine to oxycodone hydrochloride, however, typically exceeded said 10 ppm limit.

The conventional oxycodone hydrochloride compositions would thus have to be subjected to one or more additional processing steps (e.g., hydrogenation, multiple recrystallizations, etc.) to reduce the amount of 14-hydroxycodeinone or its hydrochloride salt in the oxycodone hydrochloride compositions below the limit set by the FDA or another regulatory authority, before these compositions could be incorporated into pharmaceutical dosage forms and/or administered to mammals. These additional processing steps typically increase the production costs of pharmaceutical dosage forms, and have the potential to form new compounds and/or increase amounts of certain compounds above the limits set by the regulatory authorities for these compounds.

The conventional processes for preparing oxycodone or oxycodone salts are also often not very volume and cost efficient in their oxidation step, or they are complicated and require specific equipment.

There is a continuing need for oxycodone compositions and oxycodone salt compositions which may directly be incorporated into pharmaceutical dosage forms without or with a reduced number of additional processing steps, processes for preparing these compositions, and starting and intermediary compounds or compositions used in and/or produced by these processes.

There is also a continuing need for processes which allow for an increase in volume efficiency, comprise a reduced number of processing steps and/or reduce manufacturing costs of processes for preparation of pharmaceutical compositions and dosage forms containing opioids, as compared to the conventional processes.

There is also a continuing need for processes for preparing opioids which exhibit a reduced amount of by-products in the process intermediates (e.g., of 8-hydroxyoxycodone in the intermediate 14-hydroxycodeinone) and/or in the final opioid product (e.g., of 14-hydroxycodeinone in oxycodone hydrochloride).

SUMMARY OF THE INVENTION

The invention is directed to compounds and compositions for use as starting materials or intermediate materials in the preparation of opioids including, e.g., oxycodone base and/or an oxycodone salt; processes for preparing these compounds and compositions; uses of these compounds and compositions in the preparation of APIs and pharmaceutical dosage forms; and uses of said APIs and pharmaceutical dosage forms in the treatment of medical conditions.

The compounds and compositions of the invention allow, inter alia, for more efficient (e.g., more volume efficient) and cheaper preparation of pharmaceutical products comprising opioids (e.g., oxycodone salts) than conventional processes, e.g., because the compounds and compositions of the invention may be incorporated into pharmaceutical dosage forms without additional processing steps (e.g., without being (re)hydrogenated and/or (re)crystallized prior to the incorporation into the pharmaceutical dosage forms).

In one aspect, the invention is directed to compounds and compositions for use as starting materials or intermediate materials in the preparation of oxycodone base and/or oxycodone salts; processes for preparing these compounds and compositions; and uses of these compounds and compositions in the preparation of pharmaceutical dosage forms containing oxycodone or an oxycodone salt. These compounds, compositions, and dosage forms in preferred embodiments comprise or are prepared from a salt of 14-hydroxycodeinone or compositions comprising a salt of 14-hydroxycodeinone. They may be used in the treatment of medical conditions (e.g., pain, addiction, cough, diarrhea, etc.).

In another aspect, the invention is directed to compositions comprising a salt of 14-hydroxycodeinone (e.g., 14-hydroxycodeinone sulfate), which compositions are useful as starting materials or intermediate materials in the preparation of pharmaceutical compositions and dosage forms comprising oxycodone base and pharmaceutical compositions and dosage forms comprising an oxycodone salt (e.g., oxycodone hydrochloride).

In one aspect, the present invention is directed to a process for preparing a compound of formula V, or a solvate thereof, by oxidation of a compound of formula I (Scheme 5):

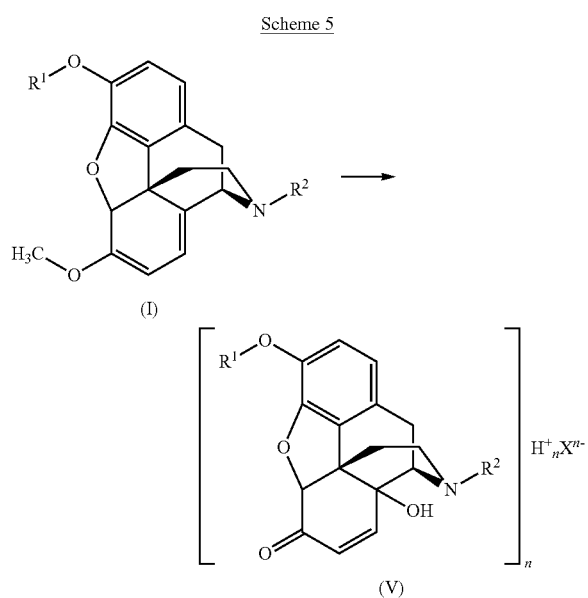

Said compound of formula V contains a compound of formula II as structural element:

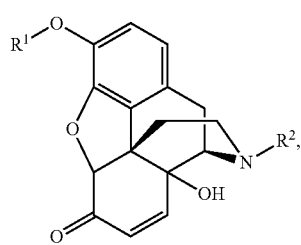

wherein $R^1$ and $R^2$ are defined as below. An example of a compound of formula II is 14-hydroxycodeinone. In the compound of formula V, the compound of formula II is typically protonated by a proton (H+), and thus forms a cation. For example, when n=2, the two protons and two compounds of formula II which are present in the compound of formula V form two cations of formula II in its protonated form.

Said compound of formula V or solvate thereof may be precipitated from the reaction mixture formed in the reaction of Scheme 5. The compound of formula V or solvate thereof can then be used as a starting material (either isolated or directly) for preparing other opioids, for example, a compound of formula IV:

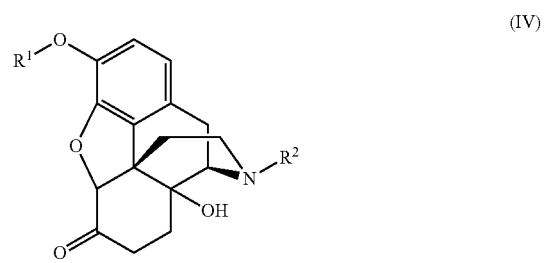

wherein $R^1$ and $R^2$ are defined as below, or an (optionally pharmaceutically acceptable) salt or solvate thereof. The compound of formula V may or may not be isolated from the reaction mixture prior to preparing the compound of formula IV. In one aspect, the compound of formula V or solvate thereof is used as a starting material for preparing a salt of the compound of formula IV or solvate thereof, wherein the anion in the salt of the compound of formula IV is the same $X^{n-}$ as in the compound of formula V.

The present invention is also directed to the compounds of formula V and to other opioids prepared by the processes of the present invention, to compositions comprising said compounds, and to their use in the preparation of pharmaceutical compositions and dosage forms.

Hence, in certain embodiments, the present invention provides a process for preparing a compound of formula V or a solvate thereof

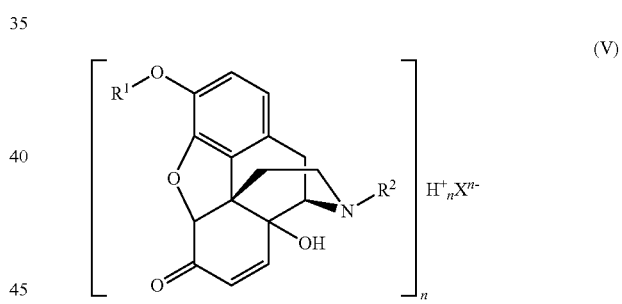

from a compound of formula I or a salt or solvate thereof, the process comprising:

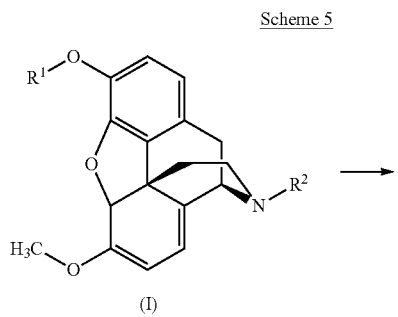

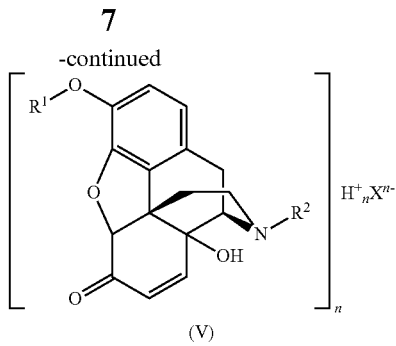

(a) oxidizing the compound of formula I; and
(b) adding an acid $H^+_n X^{n-}$ to the reaction mixture before, during and/or after the oxidation reaction, wherein
$R^1$ is —$CH_3$;
$R^2$ is —H, —$CH_3$, —($C_2$-$C_7$)alkyl, —($C_2$-$C_4$)alkenyl, benzyl, —($C_1$-$C_7$)alkyl-($C_3$-$C_7$)cycloalkyl, —CN, or an N-protecting group;
$X^{n-}$ is an anion selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof; and
n is 1, 2, or 3.
In a preferred embodiment, the acid $H^+_n X^{n-}$ is added to the reaction mixture before or during the oxidation reaction. More preferably, the acid $H^+_n X^{n-}$ is present in the reaction mixture during the complete oxidation reaction, i.e. it is added before the start of the oxidation reaction, or at the start of the oxidation reaction.

In addition to the compound of formula V, the oxidation of compound of formula I may generate a compound of formula III or a salt or solvate thereof. The compound of formula III may be formed as follows:

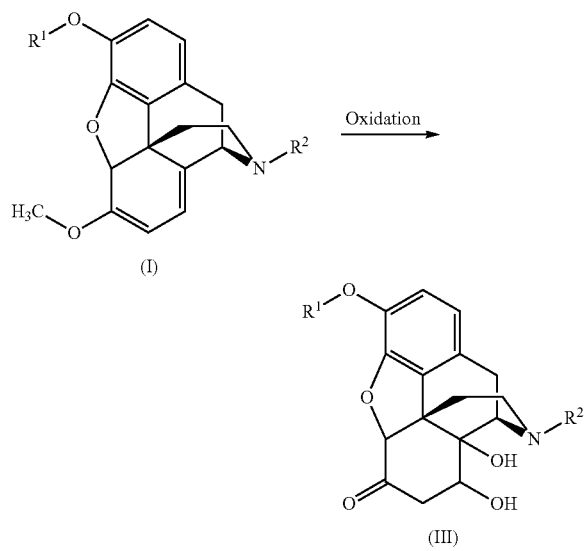

Scheme 6

The compound of formula III is an 8-hydroxy compound, e.g., 8-hydroxyoxycodone. The compound of formula III may have 8α or 8β stereoconfiguration. The 8α and 8β stereoconfiguration are exemplified for 8-hydroxyoxycodone in Schemes 3 and 4. The compound of formula III may be the 8α compound, or the 8β compound, or a mixture of the 8α compound of formula III and the 8β compound of formula III.

The formation of the compound of formula V or solvate thereof can reduce the amount of the compound of formula III which is present after oxidation of the compound of formula I, as compared to a process where the compound of formula I is oxidized without involving the compound of formula V.

Once the compound of formula V is formed, the compound of formula V or solvate thereof can be precipitated and optionally isolated. Typically, at least some compound of formula III or salt or solvate thereof remains in the supernatant. Thus, a separation of the compound of formula III from the compound of formula V or solvate thereof may be achieved by the precipitation. The precipitated and optionally isolated precipitate, which contains the compound of formula V or the solvate thereof, may contain a lower ratio of the compound of formula III to the compound of formula V than the ratio of the compound of formula III to the compound of formula V in the mother liquor.

Thus, the formation of a 14-hydroxycodeinone salt (compound of formula V) and the isolation of the precipitated salt appear to prevent or reduce (i) the formation of 8-hydroxyoxycodone during oxidation of thebaine, as compared to processes which do not involve the formation of the compound of formula V, (ii) the presence of 8-hydroxyoxycodone in a composition comprising oxycodone base made via a compound of formula V, and (iii) the presence of 8-hydroxyoxycodone or a salt thereof and 14-hydroxycodeinone or a salt thereof in an oxycodone salt or in a pharmaceutical composition comprising an oxycodone salt. The same applies to other compounds of formula V and the corresponding compounds of formulae I, II, III, and IV.

Pharmaceutical compositions prepared by processes of the present invention may be quantitatively different from pharmaceutical compositions prepared by conventional processes which do not utilize the compound of formula V, and may offer advantages over the compositions prepared by conventional processes, e.g., in terms of safety, efficiency and reduced manufacturing costs. For example, these compositions may contain less by-products and/or require less or no further processing steps after synthesis of their API.

Moreover, adding the acid $H^+_n X^{n-}$ may allow for a more volume efficient oxidation process, as compared to the conventional oxidation reaction which is exemplified in the Background Section for oxidation of thebaine. The volume efficiency of a subsequent reaction utilizing the compound of formula V or solvate thereof as starting material may also be improved, e.g., when the compound of formula V or solvate thereof is used in its precipitated form.

An exemplary embodiment of the process for preparing a compound of formula V is a process for preparing 14-hydroxycodeinone as its sulfate salt (or a solvate thereof), which encompasses the oxidation of thebaine illustrated in Scheme 7:

Scheme 7

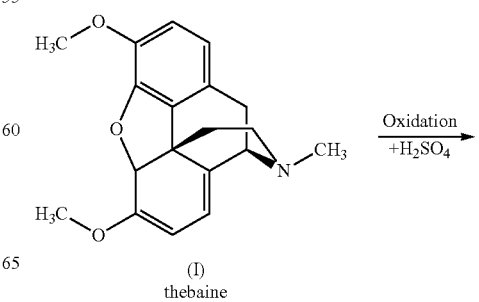

(I)
thebaine

-continued

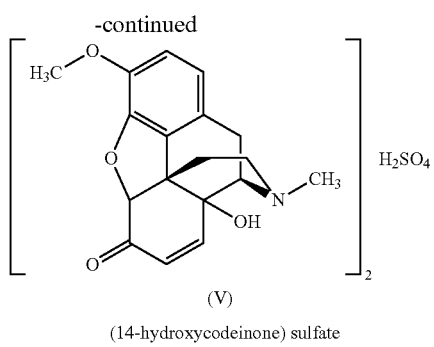

(V)

(14-hydroxycodeinone) sulfate

In one preferred embodiment, the compound of formula I is thebaine, the compound of formula II is 14-hydroxycodeinone, the acid $H^+_n X^{n-}$ is $H_2SO_4$, and the compound of formula V is a sulfate of 14-hydroxycodeinone:

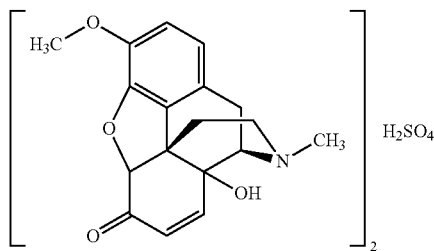

or a solvate thereof.

The present invention, in certain embodiments, provides a compound having the formula V or a solvate thereof (V)

wherein $R^1$, $R^2$, $X^{n-}$ and n are defined as above.

In one embodiment of the present invention, the compound of formula V is

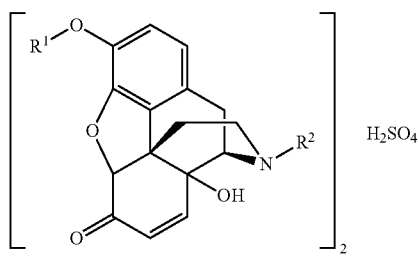

or a solvate thereof,
wherein $R^1$ and $R^2$ are defined as above.

In one embodiment, the compound of formula V is or a solvate thereof. In the context of the present invention, this compound will be designated as 14-hydroxycodeinone sulfate. Because of its stoichiometric composition, it may also be designated as bis(14-hydroxycodeinone)sulfate. The terms (compound of formula II)sulfate (e.g., 14-hydroxycodeinone sulfate) and bis(compound of formula II)sulfate (e.g., bis(14-hydroxycodeinone)sulfate) are used interchangeably in the context of the present invention.

Moreover, provided is a process for preparing a compound of formula IV or an (optionally pharmaceutically acceptable) salt or solvate thereof, the process comprising a conversion of a compound of formula V or a solvate thereof to a compound of formula IV or salt or solvate thereof, e.g., by hydrogenation of the compound of formula V or solvate thereof. In said process, the compound of formula V or a solvate thereof may be used as a starting material or as an intermediate material. In each of these cases, said compound of formula V or solvate thereof may be prepared by the process starting from the compound of formula I as described above.

Said process for preparing a compound of formula IV or an (optionally pharmaceutically acceptable) salt or solvate thereof may be represented by the following reaction Scheme 8:

Scheme 8

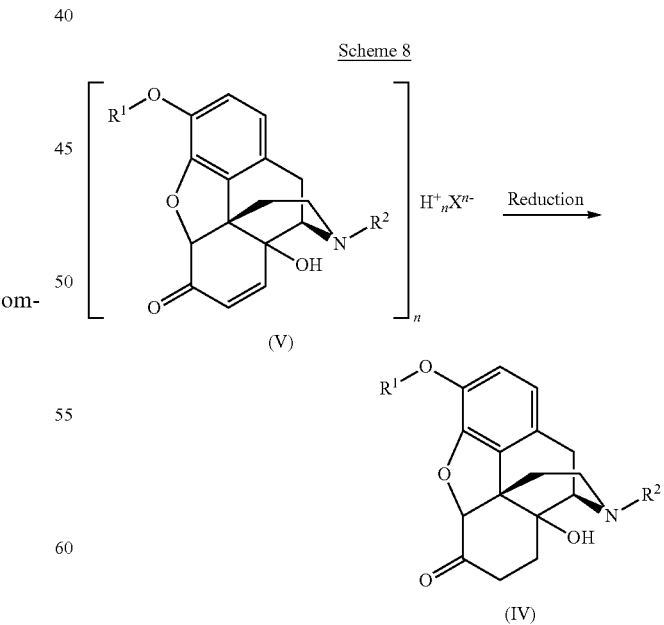

wherein $R^1$, $R^2$, $X^{n-}$ and n are defined as above.

The process may comprise the steps of providing a solution or suspension of the compound of formula V or a solvate thereof; and reducing the compound of formula V or solvate thereof to the compound of formula IV or an (optionally pharmaceutically acceptable) salt or solvate thereof.

Hence, the present invention also provides a process for preparing a compound of formula IV or a salt or solvate thereof from a compound having formula V or a solvate thereof

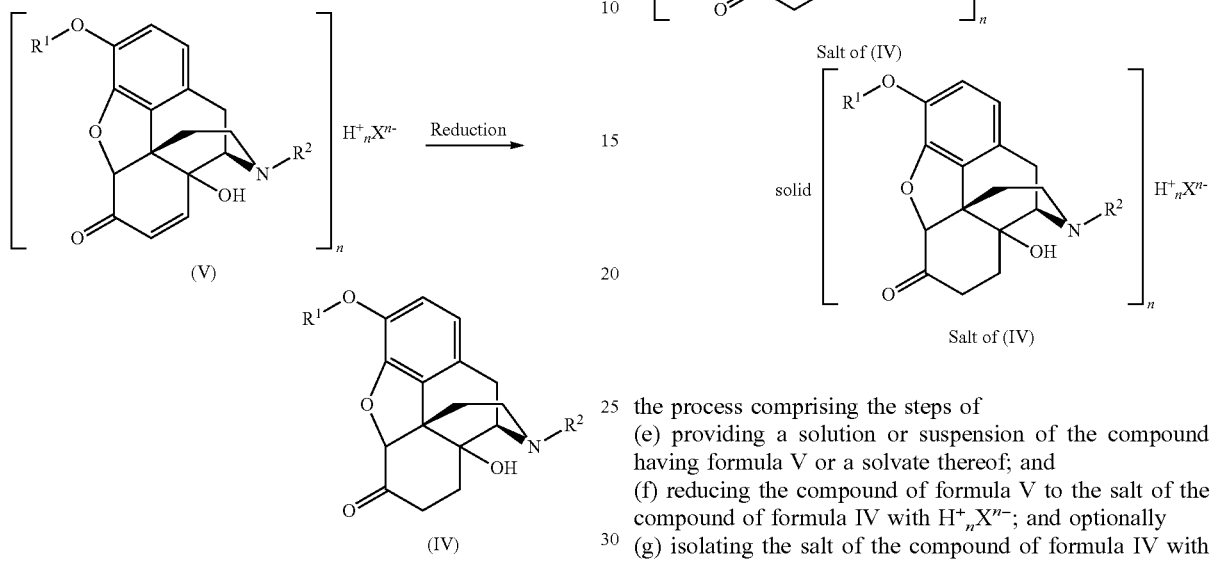

the process comprising the steps of
(e) providing a solution or suspension of the compound having formula V or a solvate thereof; and
(f) reducing the compound of formula V to the compound of formula IV,
wherein $R^1$, $R^2$, $X^{n-}$ and n are defined as above.

After the reduction reaction, the compound of formula IV may be present as its salt or solvate in the reaction mixture, e.g., as its sulfate salt. In a subsequent step, it may be converted into its free base and/or converted into a different salt or solvate, e.g., a pharmaceutically acceptable salt or solvate. It may be isolated from the reaction mixture in one or more of these forms.

In one embodiment, the compound of formula IV is present, e.g., as its sulfate salt in the reaction mixture, and this sulfate salt or a solvate thereof may be optionally isolated from the reaction mixture, e.g. by precipitation and subsequent isolation of the precipitate. In said embodiment, the process may be represented by the following reaction scheme:

the process comprising the steps of
(e) providing a solution or suspension of the compound having formula V or a solvate thereof; and
(f) reducing the compound of formula V to the salt of the compound of formula IV with $H^+_n X^{n-}$; and optionally
(g) isolating the salt of the compound of formula IV with $H^+_n X^{n-}$,
wherein $R^1$, $R^2$, $X^{n-}$ and n are defined as above, and $X^{n-}$ is preferably $SO_4^{2-}$. This reduction is performed directly from salt to salt, i.e. without intermediate isolation of the free base II. Moreover, the salt of the compound of formula IV prepared by said process is preferably oxycodone sulfate or a solvate thereof. I.e., in a preferred aspect of this process, 14-hydroxycodeinone sulfate (or a solvate thereof) is reduced to oxycodone sulfate (or a solvate thereof). A reduction of V to the salt of IV wherein $X^{n-}$ is trifluoroacetate is also specifically considered in the context of the present invention.

The present invention also provides a process wherein a compound of formula II is converted to a salt of the compound of formula IV with $H^+_n X^{n-}$, e.g. to a sulfate salt of formula IV. This conversion is achieved by reducing the compound of formula II in the presence of the acid $H^+_n X^{n-}$. The acid $H^+_n X^{n-}$ may be added before or during the reduction reaction. The resulting salt of the compound of formula IV with $H^+_n X^{n-}$ may be optionally isolated from the reaction mixture, e.g. by precipitation and subsequent isolation of the precipitate. In said embodiment, the process may be represented by the following reaction scheme:

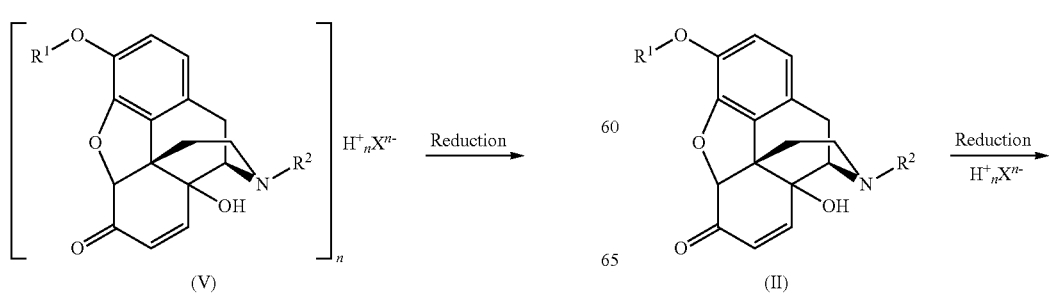

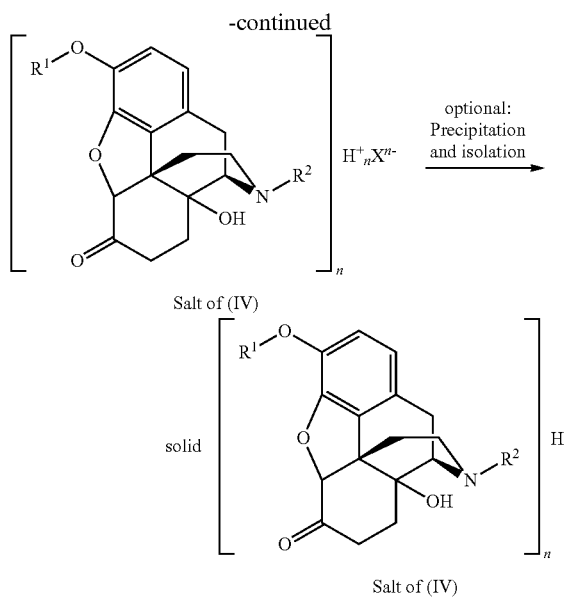

Salt of (IV)

the process comprising the steps of
(e) providing a solution or suspension of the compound having formula II or a solvate thereof; and
(f) reducing the compound of formula II in the presence of an acid $H^+_n X^{n-}$ to the salt of the compound of formula IV with $H^+_n X^{n-}$; and optionally
(g) isolating the salt of the compound of formula IV with $H^+_n X^{n-}$,
wherein $R^1$, $R^2$, $X^{n-}$ and n are defined as above, and $X^{n-}$ is preferably $SO_4^{2-}$. This reduction is performed using the free base II. Said base may be provided by isolating it as intermediate from a compound of formula V. Moreover, the salt of the compound of formula IV prepared by said process is preferably oxycodone sulfate or a solvate thereof. I.e., in a preferred aspect of this process, 14-hydroxycodeinone base is converted to oxycodone sulfate (or a solvate thereof). A process for preparing a salt of IV wherein $X^{n-}$ is trifluoroacetate is also specifically considered in the context of the present invention.

It should be apparent to a person skilled in the art that the terms "salt" and "solvate" in the present specification encompass "a pharmaceutically acceptable salt" and "a pharmaceutically acceptable solvate", respectively. The formation of a pharmaceutically acceptable salt or solvate may be achieved either directly or by the preparation of a pharmaceutically unacceptable salt or solvate and a subsequent conversion to the pharmaceutically acceptable salt or solvate. A conversion of one pharmaceutically acceptable salt or solvate to another pharmaceutically acceptable salt or solvate is also possible.

The processes of the present invention are suitable for reducing the amount of a compound of formula II and/or a compound of formula III in a compound of formula IV or a salt or solvate thereof prepared directly from the compound of formula V or via a process utilizing the compound of formula V as an intermediate, in comparison to processes using other intermediates or starting materials. In particular, using the compound of formula V allows for the reduction of the amount of compound of formula III in the compound of formula IV. This, in turn, may result in lower amounts of compound of formula II which may be formed during conversion of the compound of formula IV to a salt thereof by acid addition after step (f) of the process described above.

The product obtainable by said process encompassing steps (e) and (f), i.e., a compound of formula IV

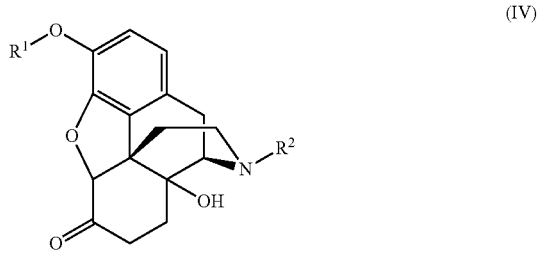

wherein $R^1$ and $R^2$ are defined as above,
or an (optionally pharmaceutically acceptable) salt or solvate thereof,
is also provided by the present invention. In one embodiment, said compound of formula IV is provided as its salt or a solvate thereof having $X^{n-}$ as anion, in particular as its sulfate salt or a solvate thereof. As already indicated above, the product of said process encompassing steps (e) and (f) is preferably oxycodone sulfate. However, in one aspect of the present invention, oxycodone sulfate as a compound itself is not encompassed by the present invention, as said compound has been known before in the art. In one aspect of the present invention, oxycodone trifluoroacetate or a solvate thereof is provided as a compound itself.

Said compound of formula IV or (optionally pharmaceutically acceptable) salt or solvate thereof, when prepared by a process according to present invention, may comprise only very low amounts of a compound of formula II. As explained above, under the conditions described in the prior art, a compound of formula II may be formed from the compound of formula III when preparing the compound of formula IV or a salt or solvate thereof. In particular, the compound of formula IV or the pharmaceutically acceptable salt or solvate thereof according to the present invention may comprise an amount of the compound of formula II which is below the threshold amount of compound of formula II mandated by the regulatory authorities for the approval of pharmaceutical compositions for use and sale to the public, and/or it comprises an amount of the compound of formula III

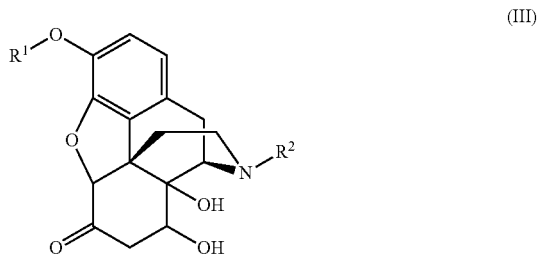

wherein $R^1$ and $R^2$ are defined as above,
or a salt or solvate thereof,
which, under the prior art conditions, is insufficient to increase the amount of a compound of formula II or a salt or solvate thereof, upon further processing of the compound of formula IV or a salt or solvate thereof, above said threshold amount.

In certain embodiments, the present invention provides a salt of a compound of formula IV, or a solvate thereof. In certain embodiments, the present invention provides a hydrochloride of a compound of formula IV, e.g., oxycodone hydrochloride, or a solvate thereof. In certain embodiments, the present invention provides a sulfate of a compound of formula IV, e.g., oxycodone sulfate, or a solvate thereof. In certain embodiments, the present invention provides a trifluoroacetate of a compound of formula IV, e.g., oxycodone trifluoroacetate, or a solvate thereof.

In yet another aspect, the invention is directed to a pharmaceutical composition comprising a salt of a compound of formula IV (e.g., an oxycodone salt), a compound of formula III (e.g., 8-hydroxyoxycodone) or a salt thereof, and a compound of formula II (e.g., 14-hydroxycodeinone) or a salt thereof, the composition having a ratio of (i) the compound of formula III (e.g., 8-hydroxyoxycodone) to (ii) the compound of formula II (e.g., 14-hydroxycodeinone) which is the same or about the same as the ratio of (i) the compound of formula III (e.g., 8-hydroxyoxycodone) to (ii) the compound of formula II (e.g., 14-hydroxycodeinone) in the composition from which it was directly prepared from (i.e., within 20% of the ratio of the composition it was prepared from). The compositions of the invention therefore allow for more efficient and cheaper preparation of pharmaceutical compositions. For example, the preparation of oxycodone hydrochloride may be more efficient because the ratio of (i) the 8-hydroxyoxycodone to (ii) the 14-hydroxycodeinone in the final product is known before the final product is manufactured and the manufacturing process may be adjusted or planned based on this ratio.

The present invention further provides pharmaceutical compositions and dosage forms, which comprise a compound of formula IV or a pharmaceutically acceptable salt or solvate thereof as defined above (e.g., oxycodone hydrochloride). In certain embodiments, these pharmaceutical compositions have a different by-product profile and may have a different efficacy than pharmaceutical compositions prepared via the free base of a compound of formula II, rather than via the compound of formula V or a solvate thereof. In certain embodiments, the content of the compound II in these pharmaceutical compositions differs from the content of the compound of formula II in pharmaceutical compositions prepared via the free base of a compound of formula II, rather than via the compound of formula V or a solvate thereof. This encompasses pharmaceutical compositions comprising a compound of formula IV or the pharmaceutically acceptable salt or solvate thereof and a compound of formula II or a salt or solvate thereof in an amount which is below the threshold amount of the compound of formula II mandated by the regulatory authorities for the approval of these compositions for use and sale to the public. It also encompasses pharmaceutical compositions comprising, in addition to the compound of formula IV or the pharmaceutically acceptable salt or solvate thereof, a compound of formula III or a salt or solvate thereof in an amount which is insufficient to increase the levels of the compound of formula II or a salt or solvate thereof, upon further processing of the pharmaceutical compositions as described in the prior art, above the threshold amount of the compound of formula II mandated by the regulatory authorities for the approval of these compositions for use and sale to the public. It also encompasses pharmaceutical compositions comprising, in addition to the compound of formula IV or the pharmaceutically acceptable salt or solvate thereof, a compound of formula II or a salt or solvate thereof, and a compound of formula III or a salt or solvate thereof, wherein the compound of formula III is present in an amount which is insufficient to increase the levels of the compound of formula II, upon further processing as described in the prior art, above the threshold amount of the compound of formula II mandated by the regulatory authorities for the approval of these compositions for use and sale to the public.

The present invention also provides pharmaceutical compositions and dosage forms comprising a compound of formula IV or a pharmaceutically acceptable salt or solvate thereof, which is selected from the group comprising or consisting of oxycodone and pharmaceutically acceptable salts and solvates thereof, wherein the amount of the compound of formula III in the pharmaceutical compositions or dosage forms is insufficient to increase the total amount of compound of formula II in the pharmaceutical compositions and dosage forms, upon further processing of the pharmaceutical compositions or dosage forms as described in the prior art, above the threshold amount of compound of formula II.

The present invention is further directed to pharmaceutical compositions and dosage forms formed as the result of carrying out the processes of the invention, as well as methods for using these pharmaceutical compositions and dosage forms in the treatment of medical conditions. The immediate products formed by carrying out the processes of the invention may be suitable as pharmaceutical compositions themselves, without further processing steps.

Compounds and compositions in accordance with the present invention, including intermediate compositions, may be used, e.g., in the manufacture of pharmaceutical compositions and dosage forms comprising at least one compound of formula IV or a pharmaceutically acceptable salt or solvate thereof, including the compounds of formula IV which are specifically indicated in the present description. These pharmaceutical compositions and dosage forms can be used to treat or prevent one or more of the following medical conditions: pain, addiction, cough, constipation, diarrhea, insomnia associated with and/or caused by pain, cough or addiction, depression associated with and/or resulting from pain, cough or addiction, or a combination of two or more of the foregoing conditions, etc. A method for treatment or prevention of one or more of these conditions by administration of a compound of formula IV or a salt or solvate thereof to a patient is also provided by the present invention.

The use of a pharmaceutical composition or dosage form according to the present invention, comprising at least one compound of formula IV or a pharmaceutically acceptable salt or solvate thereof, including the compounds of formula IV which are specifically indicated in the present description, in the manufacture of a medicament for the treatment of one or more of these medical conditions is also part of the present invention.

DEFINITIONS

Unless otherwise specified, the following abbreviations and definitions are used in the context of the present invention.

The undefined article "a" or "an" is intended to mean one or more of the species designated by the term following said article. For example, "a compound of formula II" encompasses one or more molecules of the compound of formula II.

The term "about" in the context of the present application means a value within 15% (±15%) of the value recited immediately after the term "about," including any numeric value within this range, the value equal to the upper limit (i.e., +15%) and the value equal to the lower limit (i.e., −15%) of this range. For example, the phrase "about 100" encompasses any numeric value that is between 85 and 115, including 85 and 115 (with the exception of "about 100%", which always has an upper limit of 100%). In a preferred aspect, "about" means±10%, even more preferably ±5%, even more preferably ±1% or less than ±1%.

An "opioid" in its broadest sense encompasses all compounds usually designated with said term in the art, including opioids which act as an agonist on opioid receptors and opioids which act as an antagonist on opioid receptors. Partial agonists and partial antagonists are also known and are encompassed by the term "opioid". Opioid agonists include, e.g., oxymorphone, oxycodone, noroxymorphone, nalfurafine and salts and solvates of any of the foregoing. Opioid antagonists include, e.g., naltrexone, methylnaltrexone, naloxone, nalmefene, and salts and solvates of any of the foregoing. In the context of the present application, the term "opioid" shall encompass a compound having one of the following scaffolds (which will be designated as "morphine scaffold" in the context of present invention):

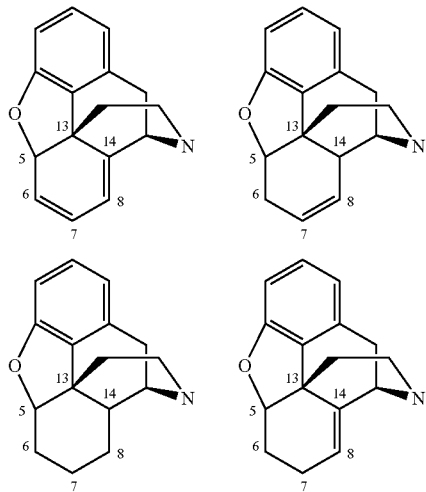

The degree of unsaturation in the ring formed by atoms 5, 6, 7, 8, 14 and 13 may vary (the ring may, e.g., just contain single bonds as in compounds of formula III, contain just one double bond as in compounds of formula II, or contain two double bonds as in compounds of formula I).

Thus, in the context of the present invention, the term "opioid" in its broadest sense encompasses compounds of formulae I, II, III, IV and V. In the processes of the present invention, opioids can serve as starting materials, intermediates, or final products. They can (for example in case of a compound having formula V) also serve as an intermediate or final product in one process and as a starting material in another process of the present invention. Whenever a "process for preparing an opioid" is mentioned herein, it will be clear from the context which opioid is prepared. In a narrower sense, the term "opioid" shall designate compounds of formula IV and (optionally pharmaceutically acceptable) salts and solvates thereof. One of the objects of the present invention is the provision of processes for ultimately preparing compounds of formula IV or pharmaceutically acceptable salts or solvates thereof which can serve as APIs (e.g., oxycodone or a pharmaceutically acceptable salt thereof), and their immediate precursors (e.g., a compound of formula V containing 14-hydroxycodeinone).

Hence, in the context of present invention the term "opioid" will also be used for referring to compounds of formula IV, whilst the term "opioid precursor" will also be used for referring to compounds of formula V.

The "threshold amount" of compound of formula II in pharmaceutical compositions and dosage forms is set by regulatory authorities such as the U.S. Food and Drug Administration (FDA) and can be learned from the latest version of the FDA guidelines ("Guidelines") or, if certain compounds of formula II are not addressed in said Guidelines, from the latest version of the ICH Guidelines. For example, for an oxycodone hydrochloride API the current threshold amount according to the FDA is 10 ppm ABUKs (which encompass 14-hydroxycodeinone) in relation to the amount of oxycodone hydrochloride. For monitored compounds of formula II (e.g., 14-hydroxycodeinone), the threshold amount refers to the amount above which the FDA will not approve the pharmaceutical composition, or dosage form thereof, for use and sale to the public. In the context of the present invention, the threshold amount may be 10 ppm or less.

The term "8-hydroxy compound" in the context of the present application means a compound containing a hydroxyl group in position 8 of the morphine scaffold. In a narrower sense, it means a compound having the structure of formula III:

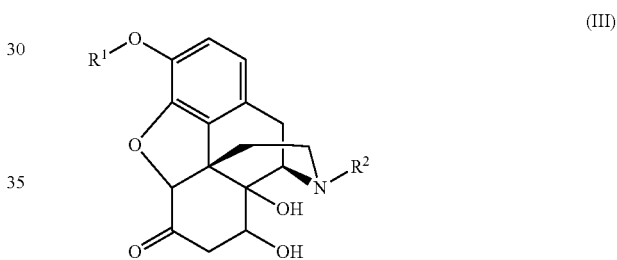

(III)

wherein
$R^1$ is —$CH_3$;
$R^2$ is —H, —$CH_3$, —($C_2$-$C_7$)alkyl, —($C_2$-$C_4$)alkenyl, benzyl, —($C_1$-$C_7$)alkyl-($C_3$-$C_7$)cycloalkyl, —CN, or an N-protecting group;
or a salt or solvate thereof. The term "8-hydroxy compound" includes the 8α-hydroxy compound of formula III and/or the 8β-hydroxy compound of formula III.

As used in connection with the compounds of formula I, II, III, IV and V of the present invention, the terms used herein having following meaning:

"—($C_1$-$C_7$)alkyl" means a straight chain or branched non-cyclic hydrocarbon having 1, 2, 3, 4, 5, 6, or 7 carbon atoms. Representative straight chain —($C_1$-$C_7$)alkyls include -methyl, -ethyl, -n-propyl, -n-butyl, -n-pentyl, -n-hexyl, and -n-heptyl. A branched alkyl means that one or more straight chain —($C_1$-$C_5$)alkyl groups, such as methyl, ethyl or propyl, replace one or both hydrogens in one or more —$CH_2$— groups of a straight chain alkyl. The total number of C atoms in a branched chain alkyl is from 3 to 7 C atoms. Representative branched —($C_1$-$C_7$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, and 1,3-dimethylpentyl.

"—$(C_2\text{-}C_7)$alkyl" means a straight chain or branched non-cyclic hydrocarbon having 2, 3, 4, 5, 6, or 7 carbon atoms. Representative straight chain —$(C_2\text{-}C_7)$alkyls include -ethyl, -n-propyl, -n-butyl, -n-pentyl, -n-hexyl, and -n-heptyl. A branched alkyl means that one or more straight chain —$(C_1\text{-}C_5)$alkyl groups, such as methyl, ethyl or propyl, replace one or both hydrogens in one or more —$CH_2$— groups of a straight chain alkyl. The total number of C atoms in a branched chain alkyl is from 3 to 7 C atoms. Representative branched —$(C_2\text{-}C_7)$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, and 1,3-dimethylpentyl.

"—$(C_1\text{-}C_5)$alkyl" means a straight chain or branched non-cyclic hydrocarbon having 1, 2, 3, 4, or 5 carbon atoms. Representative straight chain —$(C_1\text{-}C_5)$alkyls include -methyl, -ethyl, -n-propyl, -n-butyl, and -n-pentyl. Representative branched —$(C_1\text{-}C_5)$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, and 1,2-dimethylpropyl.

"—$(C_2\text{-}C_4)$alkenyl" means a straight chain or branched non-cyclic hydrocarbon having 2, 3, or 4 carbon atoms and including at least one carbon-carbon double bond. Representative straight chain and branched —$(C_2\text{-}C_4)$alkenyls include -vinyl, -allyl, -1-butenyl, -2-butenyl, -3-butenyl, -iso-butylenyl, -1,3-butadienyl, and the like.

"—$(C_3\text{-}C_7)$cycloalkyl" means a saturated monocyclic hydrocarbon having 3, 4, 5, 6, or 7 carbon atoms. Representative —$(C_3\text{-}C_7)$cycloalkyls are -cyclopropyl, -cyclobutyl, -cyclopentyl, -cyclohexyl, and -cycloheptyl.

"N-protecting groups" or "nitrogen protecting groups" include any group which may be suitable to protect the nitrogen from taking part in the reaction, and which may be removed after the reaction. Examples of such protecting groups include tert-butyloxycarbonyl (Boc), carbobenzyloxy (Cbz), 9-fluorenylmethyloxycarbonyl (Fmoc), Alloc, tosyl, benzenesulfonyl, trifluoromethylcarbonyl, and 2,2,2-trichloroethoxycarbonyl (TroC). Further examples can be found in Wuts and Greene, Greene's Protective Groups in Organic Synthesis, Wiley-Interscience, $4^{th}$ Edition (2006).

The term "solvate" in the context of the present application in its broadest sense means an association product of a compound or salt of the present invention with a solvent molecule. The molar ratio of solvent molecule(s) per compound molecule may vary. The molar ratio of solvent to compound/salt in the solvate may be 1 (e.g., in a monohydrate), more than 1 (e.g., 2, 3, 4, 5 or 6 in a polyhydrate), or less than 1 (e.g., 0.5 in a hemihydrate). The molar ratio need not be an integer ratio, it can also be, e.g., 0.5 (as in a hemihydrate) or 2.5. For example, 1 molecule water per molecule of 14-hydroxycodeinone sulfate is bound in 14-hydroxycodeinone sulfate monohydrate. Applied to the compounds of formula I, II, III, IV and V of the present invention or, where appropriate, to salts thereof, the solvate is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate is a hydrate wherein the ratio of water per molecule is within the range of from 1 to 8. In certain embodiments, the solvate is a hydrate wherein the ratio of water per molecule is within the range of from 1 to 6, i.e. a mono- to hexahydrate. In certain embodiments, it is a monohydrate or a pentahydrate.

The terms "precipitating"/"precipitate"/"precipitation" in the context of the present application shall encompass "crystallizing"/"crystallize"/"crystallization" unless stated otherwise. In certain embodiments, the precipitate described herein is amorphous. In certain embodiments, the precipitate is a mixture of amorphous and crystalline components. In certain embodiments, the precipitate described herein is crystalline. For example, 14-hydroxycodeinone sulfate may precipitate in a crystalline form during a process of the present invention.

The acronym "ppm" means parts per million. For purposes of the present application, the numeric ppm amount values of opioids contained in a composition containing more than one opioid are given in relation to the amount of the opioid ("reference opioid") constituting the majority of the opioids contained in said composition. Such reference opioid will typically be a compound of formula IV or a compound of formula II (which may be present in the composition as a structural moiety of compounds of formula V). The ppm values can be determined by performing a chromatographic resolution of the composition and subsequent calculation of the relative or absolute amounts of the opioid components based on the peak area. For purposes of the present invention, an HPLC method (e.g., as described in Example 1 for oxycodone and its precursors) can be performed. The composition components can be detected at a certain wavelength (e.g., at 206 nm for oxycodone and its precursors). The HPLC peak area ratio of a certain opioid component to the reference opioid determines the ppm value. The numeric ppm amount value of the one opioid compound constituting the majority of the opioids in the composition (i.e. of the reference opioid, which may be a compound of formula II or formula IV) can be obtained from the percent area of the peak of this compound in relation to the area sum of all opioid peaks.

Under the HPLC conditions used in the context of the present invention (e.g., the HPLC conditions as described in Example 1 for oxycodone and its precursors; or any other reverse phase HPLC conditions), any salt will not be determined in its salt form, but in a dissociated form. For example, the opioid moiety of a compound of formula V (e.g., of 14-hydroxycodeinone sulfate) will be detected and quantified in its dissolved form, i.e. as compound of formula II (e.g., 14-hydroxycodeinone). Consequently, the HPLC peak area detectable for an opioid salt of the present invention will be the HPLC peak area which is detected for the opioid moiety comprised in said salt. In case a salt contains more than one opioid moieties per anion, the HPLC method does not detect the absolute/relative amount of the salt itself, but of its opioid moiety. If in such a salt two opioid moieties per anion are present (such as in a compound of formula V wherein n is 2), the peak area detected in the HPLC is due to the presence of the two opioid moieties contained in said salt. In case of a compound of formula V wherein n is 3, the peak area detected in the HPLC is due to the presence of the three opioid moieties contained in said compound of formula V.

This has the following consequence: As defined above, the numeric ppm value for an opioid is the ratio of peak area for said opioid in relation to the peak area of the reference opioid. In case the present application refers to numeric ppm values for a ratio of a compound of formula III to a compound of formula V, in fact the ratio of the peak area for a compound of formula III to the peak area of the moieties having formula II (which are contained in the compound of formula V) is provided. A compound of formula V comprises n-times the structural unit of formula II (e.g., two times for a sulfate salt, three times for a phosphate salt, etc.). All ppm values given in the description are based on the original peak area ratio of the opioid moiety, without adjusting them by dividing them by n. For example, if a peak area ratio of 4 ppm is determined via HPLC for a compound of formula V wherein n is 2, the corresponding ppm value will also be 4 (and not 2). This way of giving compound ratios in ppm will be designated as "HPLC peak area ratio" in the following.

The opioid peaks which are typically considered in this determination method are peaks having an UV-Vis spectrum which is typical for an opioid. In embodiments wherein a compound of formula V is 14-hydroxycodeinone sulfate (or another 14-hydroxycodeinone salt or solvate thereof) or a compound of formula IV is oxycodone, typically the peaks of oxycodone, 8-hydroxyoxycodone, 14-hydroxycodeinone, oxycodone-N-oxide, 10-ketooxymorphone, 6α-oxycodol (i.e., 14-hydroxydihydrocodeine), 6β-oxycodol (i.e., 14-hydroxydihydroisocodeine), 10-hydroxyoxycodone, codeinone, codeine, hydrocodone, oxymorphone, noroxymorphone, pseudo-oxycodone (i.e., 2,2'-bisoxycodone) (see, e.g., Example 1) may be considered (if present).

A reverse phase HPLC method may be used for determination of ppm values.

The detection of the sample components may be performed using a UV/VIS detector, e.g., at a wavelength of 206 nm.

Alternatively, the detection of the sample components may be performed using a mass spectrometer. The amount of a certain component may be determined by using a tritiated internal standard. However, this method of detection does not require the "HPLC peak area ratio" described above, as it uses an internal standard.

In the preferred embodiments, the HPLC method described in USP 34-NF 29, First Supplement, Monograph on Oxycodone Hydrochloride, page 5016, Assay described in right column (official from Dec. 1, 2011) is used for determination of ppm values. In one aspect of said embodiments, the compound of formula V is 14-hydroxycodeinone sulfate and/or the compound of formula IV is oxycodone.

The acronym "ppb" means parts per billion.

The term "API" in the context of the present invention means "active pharmaceutical ingredient" (e.g., oxycodone hydrochloride) and shall be used in its broadest sense as a synonym for a pharmaceutically active compound in the context of the present invention. When an API is used in preparing a pharmaceutical composition or dosage form, the API is the pharmaceutically active component of said pharmaceutical composition or dosage form. Pharmaceutical compositions or dosage forms containing an API may be approved by a governmental agency for sale and use in a patient (e.g., a human). Examples of APIs described in the context of the present invention include, e.g., compounds of formula IV and pharmaceutically acceptable salts and solvates thereof, e.g., oxycodone or oxycodone hydrochloride.

The term "pharmaceutical composition" in the context of the present application means a composition which contains an API and is suitable for use in a patient (e.g., a human). It may be approved by a governmental agency for sale and use in a patient. Examples for pharmaceutical compositions described in the context of the present invention are among the compositions containing a compound of formula IV or a pharmaceutically acceptable salt or solvate thereof, e.g., oxycodone or oxycodone hydrochloride. Pharmaceutical compositions may be compositions prepared according to the invention if they comply with regulatory requirements for pharmaceutical compositions containing the same API.

The term "salt" in the context of the present application means a compound comprising at least one cation (e.g., one or two 14-hydroxycodeinone cations resulting from protonation of 14-hydroxycodeinone (free base) by a Bronsted acid (like sulfuric acid)) and at least one anion (e.g., a sulfate anion). A salt may be the result of the neutralization reaction between an acid and a base (e.g., a Bronsted acid and a Bronsted base, or a Lewis acid and a Lewis base). In its solid form, the salt may have a crystalline structure. The term "salt" as used in the present application includes anhydrous, solvated, or hydrated forms of the salt. Whenever a solution or mixture containing a salt is mentioned, the term "salt" shall also encompass the dissolved form of the salt. The term also encompasses pharmaceutically acceptable salts, in particular when it refers to a salt of a compound which can serve as API. In the context of present invention, whenever a 14-hydroxycodeinone salt is mentioned, this refers to a salt containing a 14-hydroxycodeinone cation, resulting, e.g., from protonation of the 14-hydroxycodeinone. The same applies to other salts containing a cation with a morphine scaffold. One example for a salt according to the present invention is a compound of formula V or a solvate thereof. An example for such compound of formula V is a salt which consists of two molecules of 14-hydroxycodeinone and one molecule of $H_2SO_4$, i.e. which comprises two 14-hydroxycodeinone cations per sulfate anion (14-hydroxycodeinone sulfate). In this salt, the cation results from the protonation of two molecules of 14-hydroxycodeinone and the anion is the resulting sulfate. In preferred embodiments of the present invention, a salt which is a compound of formula V is in its solid form. Another example for a salt according to the present invention is a salt of a compound of formula IV or a solvate thereof. An example for such salt of a compound of formula IV is a salt which consists of two molecules of oxycodone and one molecule of $H_2SO_4$, i.e. which comprises two oxycodone cations per sulfate anion (oxycodone sulfate). In this salt, the cation results from the protonation of two molecules of oxycodone and the anion is the resulting sulfate. In preferred embodiments of the present invention, a salt of a compound of formula IV is in its solid form.

Whenever a compound or formula mentioned herein contains an atom or structural element which could be a stereocenter (e.g., a chiral carbon atom or the morphine scaffold structure), it shall cover all possible stereoisomers unless indicated otherwise.

For compounds containing the morphine scaffold, the natural stereoconfiguration of the morphine scaffold as shown in the following shall be preferred:

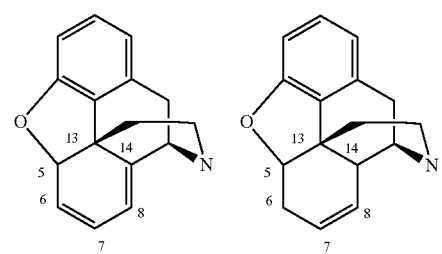

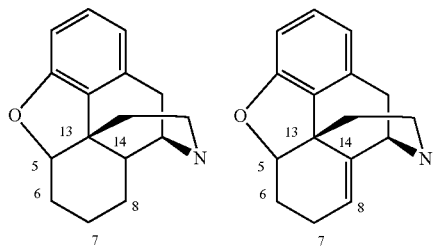

wherein the degree of unsaturation in the ring formed by atoms 5, 6, 7, 8, 14 and 13 may vary (the ring may, e.g., just contain single bonds as in compounds of formula III, or contain just one double bond as in compounds of formula II, or contain two double bonds as in compounds of formula I). At position 5, the following stereoconfiguration is preferred (exemplified for the morphine scaffold of formula I):

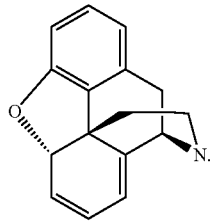

For the 8-hydroxy compounds, an α or a β configuration is possible at position 8 as illustrated in the following:

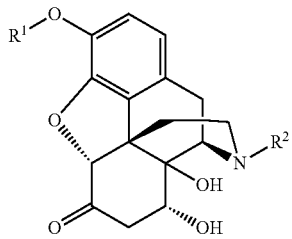

8alpha

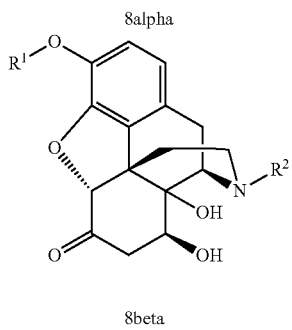

8beta

In the compounds and compositions of the present invention, either both configurations or only one configuration at position 8 may be present.

For the compounds of formula II, the following stereoconfiguration occurs at position 14 as exemplified for 14-hydroxycodeinone in the following:

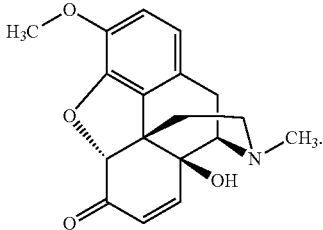 [SMILES: COc1ccc2c3c1O[C@H]1C(=O)C=C[C@@]4(O)[C@@H](C2)N(C)CCC[C@]314]

DETAILED DESCRIPTION OF THE INVENTION

I. Compounds of Formulae I, II, III, IV and V

In the context of the present invention, compounds of formulae I, II, III, IV and V, and salts and solvates thereof, and mixtures of two or more of any of the foregoing compounds are described. They may be used as starting materials, intermediates or products of the processes according to present invention, or (e.g., compounds of formula V or solvates thereof) may be themselves embodiments of the present invention. To these compounds, the following applies:

In all formulae, $R^1$ is —$CH_3$; and $R^2$ is —H, —$CH_3$, —$(C_2$-$C_7)$alkyl, —$(C_2$-$C_4)$alkenyl, benzyl, —$(C_1$-$C_7)$alkyl-$(C_3$-$C_7)$cycloalkyl, —CN, or an N-protecting group.

Preferably, $R^2$ is —H, —$(C_1$-$C_4)$alkyl, —$(C_2$-$C_4)$alkenyl, benzyl, —$(C_1$-$C_3)$alkyl-$(C_3$-$C_6)$cycloalkyl, —CN, or an N-protecting group.

More preferably, $R^2$ is —H, —$(C_1$-$C_4)$alkyl, —$(C_3)$alkenyl, benzyl, —$(C_1$-$C_3)$alkyl-$(C_3$-$C_6)$cycloalkyl, —CN, or an N-protecting group.

Even more preferably, $R^2$ is methyl, allyl, —$CH_2$-cyclopropyl, or —$CH_2$-cyclobutyl.

Most preferably, $R^2$ is methyl.

In all formulae containing stereocenters, any stereoconfiguration may be present, unless indicated otherwise. If a compound is the product of a process according to the present invention, those stereocenters of the starting material which are not taking part in the reaction will maintain their stereoconfiguration. In certain embodiments, the stereoconfiguration is as described in the Definitions section above.

In all formulae containing $X^{n-}$, $X^{n-}$ may be an inorganic or organic anion wherein n is 1, 2, or 3, preferably is 1 or 2, and more preferably is 2.

$X^{n-}$ may be any anion of a known opioid salt, including bromide, chloride, iodide, lactate, nitrate, acetate, tartrate, valerate, citrate, salicylate, meconate, barbiturate, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof.

Preferably, $X^{n-}$ is selected from the group consisting of $Cl^-$, $HSO_4^-$, $SO_4^{2-}$, methanesulfonate, tosylate, trifluoroacetate, $H_2PO_4^-$, $HPO_4^{2-}$, $PO_4^{3-}$, oxalate, perchlorate, and any mixtures thereof. More preferably, $X^{n-}$ is $HSO_4^-$, $SO_4^{2-}$, methanesulfonate, tosylate, trifluoroacetate, or a mixture thereof. Even more preferably, $X^{n-}$ is $HSO_4^-$, $SO_4^{2-}$, methanesulfonate or trifluoroacetate. Even more preferably, $X^{n-}$ is $HSO_4^-$, $SO_4^{2-}$, or trifluoroacetate. Even more preferably, $X^{n-}$ is $HSO_4^-$ or $SO_4^{2-}$. Most preferably, $X^{n-}$ is $SO_4^{2-}$.

$X^{n-}$ may be polymer-supported if n is 2 or 3.

Any combination of elements of these groups defined for $R^1$, $R^2$, $X^{n-}$ and n is also encompassed by the definitions of formulae I, II, III, IV and V.

In one embodiment of the processes of the present invention, the compound of formula I is

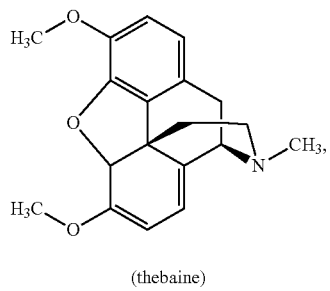

(thebaine)

or a salt or solvate thereof.

In a preferred embodiment, the compound of formula I is thebaine; the compound of formula II is 14-hydroxycodeinone; the compound of formula III is 8α-hydroxyoxycodone, 8β-hydroxyoxycodone or a mixture thereof; and the compound of formula IV is oxycodone or a salt thereof.

Thebaine may be contained in a concentrate of a poppy straw comprising thebaine as a main alkaloid (CPS-T), or it may be purified thebaine, thebaine obtained from a botanical source, synthetic thebaine, semi-synthetic thebaine, thebaine bioengineered by, e.g., bacteria or plant cell cultures, or a combination of two or more of any of the foregoing.

The compound of formula V is preferably

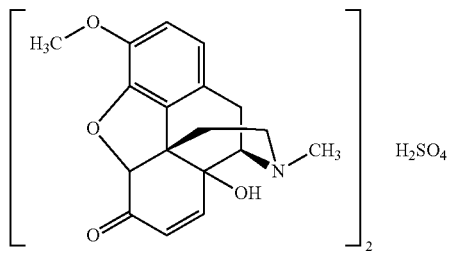

or a solvate (e.g., a hydrate) thereof, respectively. As already mentioned above, this compound will in the context of the present invention be designated as 14-hydroxycodeinone sulfate. Because of its stoichiometric composition, it may also be designated as bis(14-hydroxycodeinone)sulfate. The terms (compound of formula II)sulfate (e.g., 14-hydroxycodeinone sulfate) and bis(compound of formula II)sulfate (e.g., bis(14-hydroxycodeinone)sulfate) are used interchangeably in the context of the present invention.

When a solvate of a compound of formula V is addressed, it may be any association product of a compound of formula V with a solvent molecule. The molar ratio of solvent molecule(s) per molecule of formula V may vary. The molar ratio of solvent to compound/salt in the solvate may be 1 (e.g., in a monohydrate), more than 1 (e.g., 2, 3, 4, 5 or 6 in a polyhydrate), or less than 1 (e.g., 0.5 in a hemihydrate). The molar ratio need not be an integer ratio, it can also be, e.g., 0.5 (as in a hemihydrate) or 2.5. For example, 1 molecule water per molecule of 14-hydroxycodeinone sulfate is bound in 14-hydroxycodeinone sulfate monohydrate. The solvate of the compound of formula V is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate of the compound of formula V is a hydrate wherein the ratio of water per molecule is within the range of from 1 to 8. In certain embodiments, the solvate of the compound of formula V is a hydrate wherein the ratio of water per molecule is within the range of from 1 to 6, i.e. a mono- to hexahydrate. In certain embodiments, the solvate of the compound of formula V is a monohydrate or a pentahydrate. The same applies to other solvates in the context of the present invention, e.g. solvates of a compound of formula IV or of a salt thereof.

II. Processes for Preparing a Compound of Formula V

The present invention provides a process for preparing a compound of formula V or a solvate thereof from a compound of formula I or a salt or solvate thereof, the process comprising:
(a) oxidizing the compound of formula I;
(b) adding an acid $H^+_n X^{n-}$ to the reaction mixture before, during and/or after the oxidation reaction, thereby forming the compound of formula V.

This process is represented in the following reaction Scheme 9:

Scheme 9

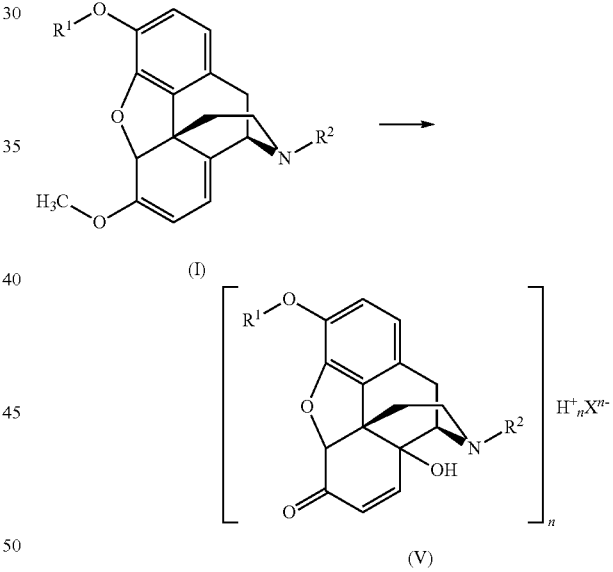

wherein $R^1$, $R^2$, $X^{n-}$ and n are defined as above.

The compound of formula V formed by this process may further contain an amount of a compound of formula III. The amount of the compound of formula III formed during this process may be less than the amount of the compound of formula III formed during an oxidation of the compound of formula I to the compound of formula II which does not involve formation of a compound of formula V.

As described above, under the conditions of the prior art, the compound of formula III may be converted to the compound of formula II during further processing of the compound of formula V to a compound of formula IV or a salt or solvate thereof. If less compound of formula III is formed according to the present invention, less compound of formula III and ultimately less compound of formula II may finally be present in a compound of formula IV or (optionally pharmaceutically acceptable) salt or solvate thereof (e.g., oxycodone or oxycodone hydrochloride) made via or from the compound of formula V or a solvate thereof, as compared to a compound of formula IV or salt or solvate thereof made via a different intermediate. Less compound of formula III and ultimately less compound of formula II may then also finally be present in a pharmaceutical composition or dosage form containing said compound of formula IV or a pharmaceutically acceptable salt or solvate thereof. Ultimately, the oxidation process of the present invention may therefore contribute to the result that the amount of the compounds of formula III and compounds of formula II formed during preparation of a compound of formula IV or salt or solvate thereof is insufficient to increase the total amount of the compound(s) of formula II in said compound of formula IV above an undesired level, e.g., above the threshold amount of the compound of formula II as defined above.

Optionally, the compound of formula III may be separated from the compound of formula V.

In certain embodiments, the oxidation step (a) is partially or completely performed in the presence of the acid $H^+_n X^{n-}$ in the reaction mixture. That is, the acid $H^+_n X^{n-}$ is added before or during the oxidation reaction, preferably before the oxidation reaction. The acid $H^+_n X^{n-}$ is preferably present in the reaction mixture during the complete oxidation reaction, i.e. it is added before the start of the oxidation reaction, or at the start of the oxidation reaction.

The compound of formula V may precipitate in certain embodiments of the present invention.

The formation of the compound of formula V or solvate thereof may occur via a salt formed from the compound of formula I, via a compound of formula II in its free base form or in its salt or solvate form, via both of said routes, or via a combination of one or both of said routes with other reaction routes known to a person skilled in the art. By way of example, the route via a compound of formula II in its free base form is shown in the following Scheme 10:

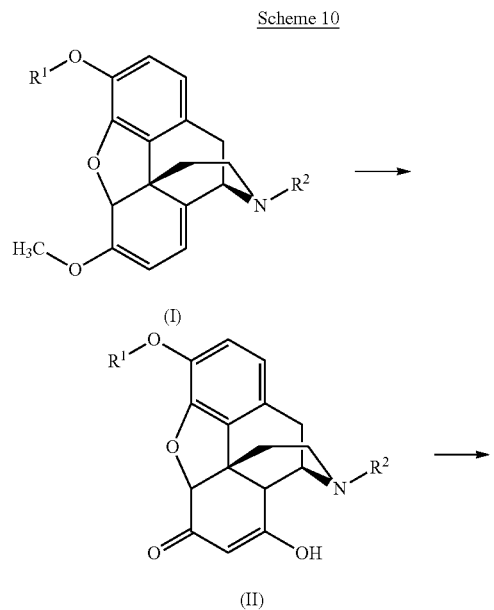

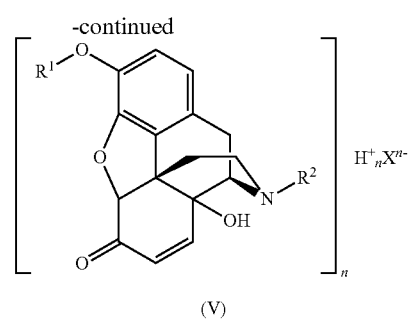

wherein $R^1$, $R^2$, $X^{n-}$ and n are defined as above.

A variation of the route shown in Scheme 10 is a route wherein at least a part or all of the compounds of formula I and/or formula II are protonated. This may happen, e.g., under acidic reaction conditions.

In certain embodiments of the present invention, the formation of the compound of formula V or a solvate thereof in this process allows for a more volume efficient oxidation of the compound of formula I in comparison to a process wherein no compound of formula V is formed.

In certain embodiments of this process, the formation of the compound of formula V results in a lower ratio of the compound of formula III to the compound of formula II in the product, as compared to a process wherein no compound of formula V or solvate thereof is formed.

In certain embodiments of this process, said result may be achieved because the formation of the compound of formula V or a solvate thereof has the effect that less 8-hydroxy compound of formula III is formed during the oxidation reaction in comparison to an oxidation reaction where no compound of formula V or solvate thereof is formed. In other words, the formation of the compound of formula V allows for an improvement of the by-product profile of the reaction product.

In these embodiments, the oxidation reaction is typically completely or partially performed in the presence of the acid $H^+_n X^{n-}$.

One example for such embodiment may be the formation of a compound of formula V, wherein n is 2 and preferably wherein $X^{n-}$ is sulfate. Another example for such embodiment may be the formation of a compound of formula V, wherein n is 1 and preferably wherein $X^{n-}$ is trifluoroacetate. Another example for such embodiment may be the formation of a compound of formula V, wherein n is 3 and preferably wherein $X^{n-}$ is phosphate.

In certain embodiments of this process said result may be achieved because the formation of formula V or a solvate thereof has the effect that compounds of formula III can be separated from the compound of formula V or the solvate thereof, e.g., by precipitation of the compound of formula V or the solvate thereof from the reaction mixture. One example for such an embodiment may be the formation of a compound of formula V wherein $X^{n-}$ is sulfate.

In certain embodiments a combination of these effects takes place, i.e., said result is achieved because both less compounds of formula III are formed during the oxidation and because said compounds of formula III can be separated from the compound of formula V or solvate thereof. One example for such an embodiment may be the formation of a compound of formula V wherein $X^{n-}$ is sulfate.

Preferably, the formation of the compound of formula V or a solvate thereof reduces the formation of 8-hydroxy compounds of formula III during the oxidation reaction and/or the presence of 8-hydroxy compounds of formula III in the oxidation product, as compared to an oxidation reaction which does not involve the step of forming the compound of formula V or a solvate thereof. The presence of a compound of formula III in the product may be reduced by precipitation of the compound of formula V. This may reduce the formation of compounds of formula II during subsequent reactions (e.g., during conversion of oxycodone made from a compound of formula V to oxycodone hydrochloride), as compared to reactions which do not involve the step of forming the compound of formula V or a solvate thereof.

The formation of the compound of formula V or a solvate thereof may also provide an opportunity to perform additional steps at this stage to further lower the amount of an 8-hydroxy compound in the compound of formula V or solvate thereof, thereby reducing the amounts of compound of formula II which may be potentially formed from the 8-hydroxy compound during a subsequent conversion of the compound of formula V, e.g., during a conversion to oxycodone hydrochloride, under the conditions of the prior art. These additional steps may comprise hydrogenation, heat treatment, (re)crystallization, washing the compound of formula V with a solvent which preferentially removes the 8-hydroxy compound rather than the compound of formula V or the solvate thereof, or any combinations of the foregoing.

The process for preparing the compound of formula V or a solvate thereof according to present invention may be performed by oxidizing a compound of formula I with an oxidizing agent in the presence of one or more acids such that the compound of formula V is formed. An 8-hydroxy compound of formula III or a salt or solvate thereof may be formed as by-product during the oxidation. At the end of the preparation of the compound of formula V or a solvate thereof, said compound of formula V or solvate thereof may be provided as a solid, a solution, or a suspension. The compound of formula V or a solvate thereof is an embodiment of the present invention, on its own right and in its function as a starting material or intermediate for further processes of the present invention, e.g., processes for preparing an opioid of formula IV or an (optionally pharmaceutically acceptable) salt or solvate thereof. The compound of formula V and the solvate thereof will be described in more detail below. However, the subsequent description of the processes of the present invention shall also apply to the compound of formula V and the solvate thereof per se where applicable (e.g., when the compound of formula V is described as a reaction product of a process according to the invention).

In one aspect, the present invention provides a process for preparing a compound of formula V or solvate thereof which is a salt of 14-hydroxycodeinone (as compound of formula II) from thebaine (as compound of formula I), the resulting salt of 14-hydroxycodeinone (i.e., the compound of formula V), and processes for further conversion of the salt to compounds of formula IV or salts or solvates thereof, in particular to oxycodone or oxycodone hydrochloride, or other opioids by one or more further chemical reactions. The process according to the present invention for preparing said compound of formula V is depicted in the following Scheme 11:

Scheme 11

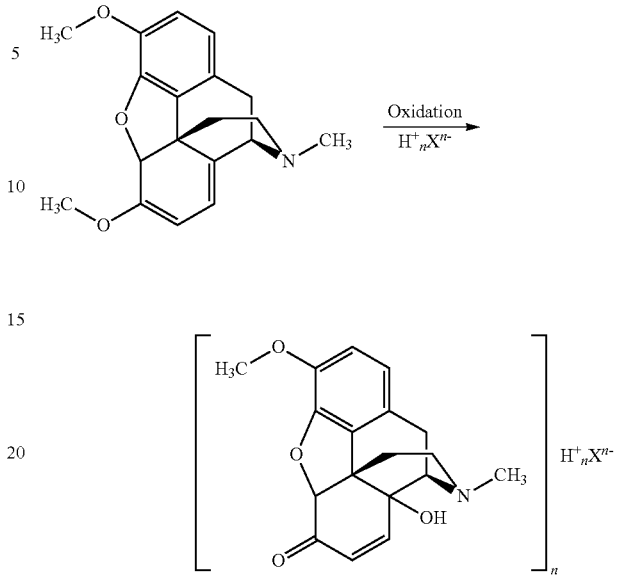

In certain embodiments of this process, the acid $H^+_n X^{n-}$ is sulfuric acid.

The process for preparing a compound of formula V may be performed as one-pot-reaction, wherein steps (a) and (b) are performed concomitantly. Such one-pot-reaction is represented in Scheme 12:

Scheme 11

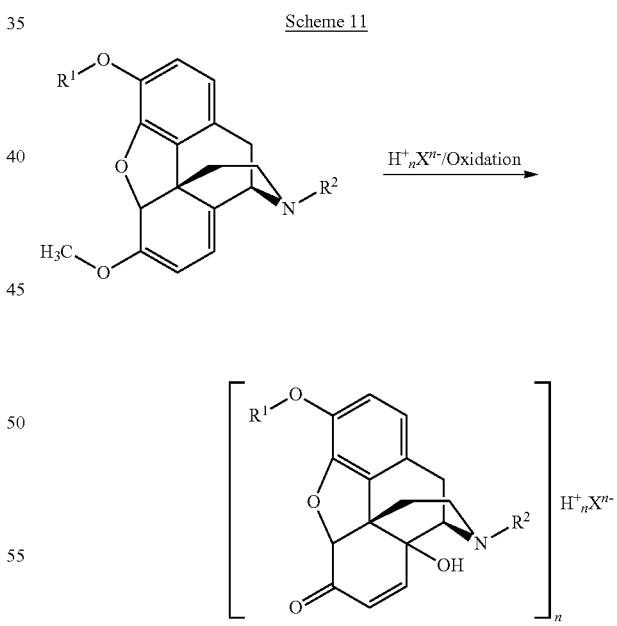

In said one-pot-reaction, at least a part of the acid $H^+_n X^{n-}$ is typically added before the oxidizing agent, or concomitantly with the oxidizing agent. In certain embodiments, all of the acid $H^+_n X^{n-}$ is added before the oxidizing agent, or concomitantly with the oxidizing agent.

An exemplary one-pot reaction for forming a compound of formula V, namely 14-hydroxycodeinone sulfate, is depicted in Scheme 13:

Scheme 13

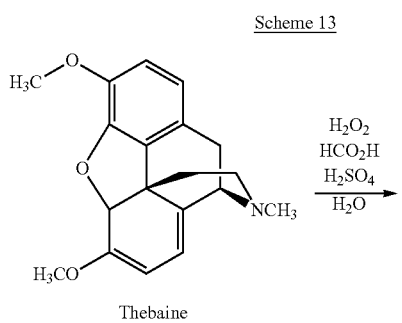

Thebaine

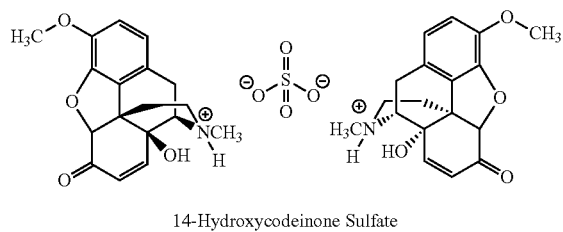

14-Hydroxycodeinone Sulfate

In the oxidation reaction depicted in this Scheme, a peracid formed from hydrogen peroxide and formic acid is used as at least one oxidizing agent, and sulfuric acid is used as the acid $H^+_n X^{n-}$. It should be noted that it is not excluded that at least part of the sulfuric acid also forms a peracid in the presence of the hydrogen peroxide, which peroxide may also take part in the oxidation reaction.

The reaction conditions of steps (a) and (b) (e.g., time, temperature, pH, relative proportions of the reagents) will be described in detail in the following. In a typical embodiment of the present invention, they are adjusted such that the resulting product containing the compound of formula V is free from, or contains about 2500 ppm or less, about 2000 ppm or less, about 1500 ppm or less, about 1000 ppm or less, about 500 ppm or less, or about 100 ppm or less of a 8-hydroxy compound of formula III.

Oxidation Reaction

The oxidation reaction of step (a) of the process according to present invention is represented in Scheme 14 and results in the formation of the structural moiety of formula II, which in turn is part of the compound of formula V (the compound of formula II is depicted in square brackets in Scheme 14):

Scheme 14

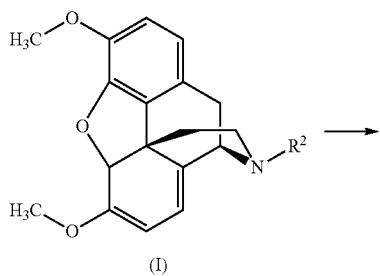

(I)

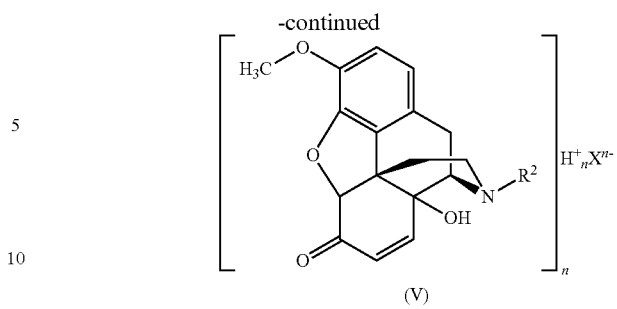

(V)

The oxidation reaction of step (a) is generally run until at least about 90%, about 92%, about 95%, about 97%, about 98%, about 99% or about 100% of the compound of formula I is consumed by the reaction. The amount of said compound remaining in the reaction may be determined by any conventional determination method, e.g., by HPLC, for example the HPLC method described in USP 34-NF 29, First Supplement, Monograph on Oxycodone Hydrochloride, page 5016, Assay described in right column (official from Dec. 1, 2011).

The oxidizing reaction time can be anywhere from about 1 minute to about 36 hours, from about 10 minutes to about 34 hours, from about 20 minutes to about 32 hours, from about 30 minutes to about 30 hours, from about 45 minutes to about 28 hours, from about 1 hour to about 24 hours, from about 3 hours to about 21 hours, from about 5 hours to about 18 hours. In certain embodiments, the reaction time is about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 15 hours, about 16 hours, or about 17 hours.

The reaction mixture may be maintained at a temperature of from about 0° C. to about 100° C., from about 10° C. to about 90° C., from about 15° C. to about 80° C., from about 20° C. to about 70° C., from about 20° C. to about 60° C., from about 20° C. to about 55° C., from about 20° C. to about 45° C., from about 20° C. to about 40° C., or from about 20° C. to about 35° C.

In certain embodiments, e.g., in a reaction conducted in a flow reactor, the reaction mixture may be maintained at a temperature as listed in the preceding sentence, or it may be maintained at a temperature exceeding some of the upper temperature limits of the preceding sentence, e.g., at a temperature of from about 40° C. to about 95° C.

In certain embodiments, the reaction mixture is maintained at from about 20° C. to about 45° C., preferably from about 25° C. to about 40° C., more preferably from about 25° C. to about 35° C., even more preferably at about 30° C.

Typically, the oxidation of the compound of formula I during step (a) is taking place in the presence of an oxidizing agent. Said oxidizing agent is either added to the reaction mixture, or it is formed in situ in the reaction mixture (e.g., performic acid may be formed in situ in a reaction mixture comprising formic acid and hydrogen peroxide). The compound of formula I is then oxidized to the compound of formula V, which will result when the acid $H^+_n X^{n-}$ is present.

The compound of formula I may be provided for step (a) in a solution or suspension comprising the compound of formula I and a suitable solvent. A suitable solvent may comprise or consist of water; an alcohol (e.g., methanol, ethanol, n-propanol, isopropanol, 1-butanol, 2-butanol, isobutanol, tert-butanol, tert-amyl alcohol, 2-ethoxyethanol, 1-methoxy-2-propanol, etc.); an aromatic hydrocarbon (e.g., benzene, toluene, xylol, etc.); an ether (e.g., 1,4-dioxane, tetrahydrofuran, 2-methyl-tetrahydrofuran, diethylether, tert-butyl methyl ether, etc.); a ($C_1$-$C_4$) alkyl ester of a ($C_1$-$C_4$) alkanoic acid (e.g., methyl formate, methyl acetate, ethyl acetate, isopropyl acetate, etc.); an amide (e.g., dimethylformamide, diethylformamide, dimethylacetamide, or other N—($C_1$-$C_4$) alkyl substituted ($C_1$-$C_4$) alkanoic acid amides); N-methylpyrrolidone; formylmorpholine; or any mixtures of any of the foregoing. In certain embodiments, the reagent providing an acid for the process (e.g., 88% formic acid in water), or the acid itself can act as solvent. In certain embodiments, the solvent comprises or consists of water, an ether, an alcohol, or a combination thereof. In certain embodiments, the solvent comprises or consists of methanol, tetrahydrofuran, n-propanol, isopropanol, acetone, ethanol, 1-methoxy-2-propanol, 2-ethoxyethanol, tert-amyl alcohol, or a mixture of water with any one of the foregoing. In certain embodiments, the solvent comprises or consists of tetrahydrofuran, isopropanol, methanol, ethanol, butanol, isobutanol, tert-amyl alcohol, n-propanol or any combination thereof. In certain embodiments, the solvent is water or a combination of water with another solvent. In certain embodiments, the solvent is isopropanol or a mixture of isopropanol and water. In certain other embodiments, the solvent is free or substantially free from water (e.g., when the reaction is performed in chloroform using MCPBA as oxidizing agent).

The ratio of the compound of formula I to the solvent is selected such that the compound of formula I is dissolved in the solvent, i.e. such that a suspension or preferably a solution of the compound of formula I is formed. If the oxidizing agent contains or is generated with an acid which acts as a solvent (e.g., formic acid), or if the acid $H^+_n X^{n-}$ acts as a solvent, said acid contributes to the total amount of solvent in the reaction mixture or is the sole solvent in the reaction mixture. The ratio of the compound of formula I (in mmol) to the solvent (in mL) may be defined as molarity by the following formula:

molarity=(mmol of compound of formula *I*)/(milliliters of solvent).

For example, when 33.7 mmol of compound I and 23.6 ml water plus formic acid are used, this results in a molarity of 1.43 (33.7/23.6). In the present invention, the molarity of the compound of formula I in relation to the solvent is preferably ≥0.8. In certain embodiments, the molarity is from 0.8 to 1.8, preferably from 1.2 to 1.6 and even more preferably from 1.3 to 1.5. In comparison, in WO 2008/130553, the molarity is 0.67 ((10 mmol compound of formula I)/(15 ml water plus formic acid)). The less solvent is used, the more volume efficient steps (a) and (b) may be if the process yield remains constant. Thus, the present invention provides a process which allows for the use of less solvent, which in turn may reduce the environmental burden and/or production costs.

Before the oxidation reaction is initiated (e.g., by adding or generating an oxidizing agent), the compound of formula I may be present in any percentage of the reaction mixture. In certain embodiments, it is present in a starting amount of from about 1% to about 60%, from about 5% to about 50%, from about 10% to about 40%, from about 15% to about 35%, or from about 20% to about 30% per weight of the complete reaction mixture. In certain preferred embodiments, the compound of formula I comprises from about 20% to about 30% of the reaction mixture by weight. As the oxidation takes place, the concentration of the compound of formula I decreases and may finally approach 0%.

The oxidizing agent may be a peracid, a peroxide (which encompasses hydrogen peroxide and peroxide salts), a periodinane, singlet oxygen or any combination thereof. For example, an oxidizing agent may be hydrogen peroxide, potassium peroxymonosulfate (e.g., OXONE®), performic acid, peracetic acid (AcOOH), persulfuric acid, m-chloroperoxybenzoic acid (MCPBA), trifluoro peracetic acid, singlet oxygen, iodosylbenzene, $K_2O_2$, $Na_2O_2$, $Li_2O_2$, $Cs_2O_2$, $Cs_2O_2$, $K_2SO_5$, $NaSO_5$, or an appropriate mixture of any two or more of the foregoing. Said oxidizing agent may be either generated in situ in the reaction mixture (e.g., performic acid from hydrogen peroxide and an acid), or it may be added to the reaction mixture (e.g., MCPBA).

In certain embodiments, the oxidizing agent is a peracid. Said peracid may either be generated in situ in the reaction mixture from hydrogen peroxide and an acid or from another combination of reagents leading to the formation of a peracid (e.g., from a peroxide salt and an acid), or it may be added to the reaction mixture (e.g., MCPBA, or a peracid generated ex situ, i.e. separately from the reaction mixture before its addition to the reaction mixture). If the peracid is generated in situ, the peroxide may be added after the acid and/or at a pH of the reaction mixture which is less than 7.

In certain embodiments, the peracid may be performic acid, peracetic acid, MCPBA, potassium peroxymonosulfate (which contains one peracid group), trifluoro peracetic acid, persulfuric acid, or a combination of any two or more thereof. When said peracid is generated in situ, the corresponding starting acid is formic acid, acetic acid, 3-chlorobenzoic acid, potassium monosulfate, trifluoroacetic acid, sulfuric acid, or a mixture of any two or more of the foregoing.

In certain embodiments, the peracid comprises or is performic acid. When the performic acid is generated in situ or ex situ, it is in one embodiment generated from formic acid and hydrogen peroxide.

In certain embodiments, the peracid comprises or is a combination of performic acid and persulfuric acid. When said combination is generated in situ or ex situ, it is in one embodiment generated from formic acid, sulfuric acid and hydrogen peroxide.

In certain embodiments, the oxidizing agent is or is generated from hydrogen peroxide (e.g., added to the reaction mixture in 5, 10, 15, 20, 25, 30, 35, 40, 45, 50, 60, or 70% aqueous solution). In certain embodiments, 35% aqueous solution of hydrogen peroxide is added to the reaction mixture. In certain embodiments, at the beginning of the reaction, hydrogen peroxide may comprise about 8-10% of the reaction mixture by volume, and, as the oxidation reaction takes place, the concentration of hydrogen peroxide decreases and may even reach 0%.

In general, the oxidizing agent, e.g., a peracid generated from an acid and hydrogen peroxide, is present in an amount of from about 0.8 to about 5 moles per mole of the compound of formula I. In certain embodiments, from about 1 to about 2 moles of the oxidizing agent per 1 mole of the compound of formula I are utilized. In certain embodiments, about 1, about 1.1, about 1.2, about 1.4, about 1.5, about 1.6, about 1.8, or about 1.9 moles of the oxidizing agent per mole of the compound of formula I are used. In certain embodiments, from about 1 to about 1.6 moles of the oxidizing agent per mole of the compound of formula I are utilized. In certain embodiments, from about 1 to about 1.25 moles of the oxidizing agent per mole of the compound of formula I are utilized. In certain embodiments, from about 1.05 to about 1.15 moles (e.g., 1.05 molar equivalents) of oxidizing agent per mole of the compound of formula I are used. In embodiments wherein a peracid is generated in situ, the molar amount of the starting component containing the peroxy group (e.g., hydrogen peroxide) is deemed to represent the molar amount of the resulting peracid in the reaction mixture.

In those embodiments wherein the oxidizing agent is a peracid generated in situ from hydrogen peroxide and an acid in the reaction mixture, preferably from about 1 to about 1.6 moles of hydrogen peroxide per mole of the compound of formula I are utilized. In certain embodiments, from about 1 to about 1.25 moles of hydrogen peroxide per mole of the compound of formula I are utilized. In certain embodiments, from about 1.05 to about 1.15 moles (e.g., 1.05 molar equivalents) of hydrogen peroxide per mole of the compound of formula I are used.

In those embodiments wherein the oxidizing agent is a peracid generated in situ from hydrogen peroxide and an acid in the reaction mixture, the acid for generating the peracid preferably is or comprises formic acid. This also encompasses processes wherein the peracid is generated from a combination of formic acid and sulfuric acid.

The molar amount of an acid used for generating a peracid in situ may be less than, equal to, or exceeding the molar amount of the compound of formula I. In certain embodiments, an excess of said acid over the amount of the compound of formula I will be utilized. In certain embodiments, said acid is used in excess over the amount of the peroxide (e.g., hydrogen peroxide) which is used to generate the peracid. In certain embodiments, the amount of the acid used for generating the peracid (e.g., of formic acid) is from about 0.5 to about 14 molar equivalents per molar equivalent of the compound of formula I, preferably from about 1 to about 12 molar equivalents, more preferably from about 1 to about 7 molar equivalents, more preferably from about 1.5 to about 6 molar equivalents, more preferably from about 2 to about 4.5 molar equivalents, even more preferably from about 2.5 to 4 molar equivalents per molar equivalent of the compound of formula I.

When an acid is used for generating the oxidizing agent in situ, two acids may be used during a process encompassing steps (a) and (b): a first acid (which is used to generate at least a part of the peracid in situ in step (a)), and a second acid (which is the acid $H^+{}_nX^{n-}$ of step (b), which in certain embodiments may also generate a part of the peracid in situ in step (a)). The second acid may be added before, simultaneously with, or after addition of the first acid. In certain embodiments, the acids are pre-mixed and the pre-mixture is added to the solution or suspension. In certain embodiments, the first acid and the second acid may each be independently added all at once or in divided portions. In certain embodiments, the first acid is formic acid and the second acid is sulfuric acid.

The acid $H^+{}_nX^{n-}$ of step (b) may be added as acid $H^+{}_nX^{n-}$ or may be generated in situ in the reaction mixture from a salt containing an anion $X^{n-}$.

The acid $H^+{}_nX^{n-}$ may be added (or generated in situ) before, during or after the oxidation reaction of step (a), or at any combination of these time points. It may be added once, in several batches or continuously over a certain period of time. It may be added at or during several points in time in relation to the oxidation reaction, e.g., before, during and after the oxidation, or before and during the oxidation reaction. If it is added (or generated) before and/or during the oxidation reaction, the process comprising steps (a) and (b) is performed as a one-pot-reaction. Said one-pot-reaction may be more cost-, time- and/or volume-efficient and may therefore be preferred. Especially preferred is a process wherein the acid $H^+{}_nX^{n-}$ is added to (or generated in) the reaction mixture before the oxidation reaction of step (a).

In certain embodiments, a portion or all of the acid $H^+{}_nX^{n-}$ is added after some or substantially all of the compound of formula I has been oxidized. In certain embodiments, $H^+{}_nX^{n-}$ is added after substantially all of the compound of formula I has been consumed, with the proviso that the acid $H^+{}_nX^{n-}$ is not hydrochloric acid in these embodiments, preferably with the proviso that the acid $H^+{}_nX^{n-}$ is not methanesulfonic acid, sulfuric acid, phosphoric acid or hydrochloric acid in these embodiments.

In certain embodiments, step (b) of the process is performed by adding $H^+{}_nX^{n-}$ (e.g., $H_2SO_4$) to the reaction mixture.

$H^+{}_nX^{n-}$ may be any acid containing an anion $X^{n-}$ as defined herein. It may, for example, be HCl, $H_2SO_4$ or its monosalt, methanesulfonic acid, tosylic acid, trifluoroacetic acid, $H_3PO_4$ or one of its mono- or disalts, oxalic acid, perchloric acid, or any mixtures thereof. In certain embodiments, it may be HCl, $H_2SO_4$, methanesulfonic acid, tosylic acid, trifluoroacetic acid, or a mixture thereof. In certain embodiments, it is $H_2SO_4$, methanesulfonic acid, or trifluoroacetic acid or a mixture thereof. In certain embodiments, it is trifluoroacetic acid. In certain embodiments, it is $H_2SO_4$. In certain embodiments, it is methanesulfonic acid.

$H^+{}_nX^{n-}$ may in certain embodiments be polymer supported if n is 2 or 3.

The molar amount of $H^+{}_nX^{n-}$ present in step (b) may be the same as or different from the molar amount of the compound of formula I provided for step (a). For example, in embodiments wherein n is 2, the salt or acid added in step (b), e.g., $H_2SO_4$ or a salt thereof, may be added in an amount of from about 0.1 to about 1.5 molar equivalents, preferably of from about 0.1 to about 1.2 molar equivalents, more preferably of from about 0.1 to about 1 molar equivalents, even more preferably of from about 0.25 to about 0.75 molar equivalents, even more preferably of from about 0.4 to about 0.6 molar equivalents, even more preferably of from about 0.45 to about 0.55 molar equivalents per molar equivalent of the compound of formula I. In certain embodiments wherein n is 2, the salt or acid added in step (b), e.g., $H_2SO_4$ or a salt thereof, is added in an amount of about 0.51 to about 0.55 molar equivalents per molar equivalent of the compound of formula I.

In certain embodiments, the amount of $H^+$ provided by $H^+{}_nX^{n-}$ in step (b) is in a slight molar excess in comparison to the compound of formula I. In certain embodiments, the molar amount of $H^+{}_nX^{n-}$ present in step (b) is within a range of about 1/n+10% to about 1/n+20% molar equivalents per one molar equivalent of the compound of formula I.

In certain embodiments, the acid $H^+{}_nX^{n-}$ is the only acid used during the process encompassing steps (a) and (b). In those embodiments where a peracid is used as oxidizing agent, said acid $H^+{}_nX^{n-}$ is capable to form a peracid and will be used for generating said peracid.

In certain other embodiments, one or more additional acids are added to the reaction mixture. In those embodiments where a peracid is used as oxidizing agent, there may be used an acid for generating the peracid which is different from the acid $H^+{}_nX^{n-}$. This acid is then an additional acid. In other embodiments, a further additional acid may be added to the reaction mixture in addition to the acid $H^+{}_nX^{n-}$ and the acid for generating the peracid. Such further acid may be any remaining acid selected from the acids defined as the acid $H^+{}_nX^{n-}$ and as the acid for generating the peracid in the present description, or any mixture of said remaining acids.

The total amount of acid used during steps (a) and (b) of the process is important, because it may influence whether or not the compound of formula V precipitates from the reaction mixture during the process. The total amount of acid includes the acid $H^+{}_nX^{n-}$ and, if present, the acid used for generating a peracid and any further acid added to the reaction mixture during steps (a) and (b). The total amount of acid may range from about 0.6 to about 14.0 molar equivalents of total acid per molar equivalent of the compound of formula I.

In certain embodiments, from about 1 to about 12 molar equivalents of total acid per molar equivalent of the compound of formula I are used. In certain embodiments, from about 1 to about 10, from about 1 to about 8, from about 1 to about 7, from about 1 to about 6.5, from about 1 to about 6, from about 1 to about 5.5, from about 1 to about 5, from about 1 to about 4.5, from about 1 to about 4, from about 1 to about 3.5, or from about 1.5 to about 3.5 molar equivalents of total acid per molar equivalent of the compound of formula I are used.

In certain embodiments, from about 1 to about 8 molar equivalents, preferably from about 1 to about 5 molar equivalents, more preferably from about 1.5 to about 4.5 molar equivalents, even more preferably from about 3 to about 4 molar equivalents of total acid per molar equivalent of the compound of formula I are used.

In certain embodiments, from about 1.2 to about 4.5 molar equivalents of total acid per molar equivalent of the compound of formula I are used.

In certain embodiments where an acid $H^+{}_nX^{n-}$ and an acid used for generating the peracid (which is different from $H^+{}_nX^{n-}$) are used, the molar ratio of the acid $H^+{}_nX^{n-}$ to the acid used for generating the peracid (e.g., of sulfuric acid to formic acid) is from about 1:20 to about 1:0.5, from about 1:17 to about 1:1, from about 1:15 to about 1:1, from about 1:14 to about 1:1, from about 1:12 to about 1:1, from about 1:10 to about 1:1, from about 1:9 to about 1:2, from about 1:8 to about 1:3, from about 1:7 to about 1:3, from about 1:7 to about 1:5, or a numeric value lying within these ranges. In certain embodiments, the molar ratio of the acid $H^+{}_nX^{n-}$ to the acid used for generating the peracid is from about 1:8 to about 1:3, preferably from about 1:7.5 to about 1:4, more preferably from about 1:7 to about 1:5, or a numeric value lying within these ranges.

In certain embodiments, from about 0.5 to about 4 molar equivalents of the acid used for generating a peracid per molar equivalent of the compound of formula I are used, and from about 0.1 to about 1.5, from about 0.1 to about 1, from about 0.2 to about 0.9, from about 0.25 to about 0.75, from about 0.4 to about 0.6, or from about 0.5 to about 0.6 molar equivalents of the acid $H^+{}_nX^{n-}$ per molar equivalent of the compound of formula I are used. In said embodiments, said first acid may be formic acid, and said second acid may be sulfuric acid.

In certain embodiments, from about 0.5 to about 3.5 molar equivalents of the acid used for generating a peracid per molar equivalent of the compound of formula I are used, and from about 0.1 to about 1.5, from about 0.1 to about 1, from about 0.2 to about 0.9, from about 0.25 to about 0.75, from about 0.4 to about 0.6, or from about 0.5 to about 0.6 molar equivalents of the acid $H^+{}_nX^{n-}$ per molar equivalent of the compound of formula I are used. In said embodiments, said first acid may be formic acid, and said second acid may be sulfuric acid.

In certain embodiments, from about 1 to about 3 molar equivalents of the acid used for generating a peracid per molar equivalent of the compound of formula I are used, and from about 0.4 to about 0.6, or from about 0.5 to about 0.6 molar equivalents of the acid $H^+{}_nX^{n-}$ per molar equivalent of the compound of formula I are used. In said embodiments, said first acid may be formic acid, and said second acid may be sulfuric acid.

In a preferred embodiment utilizing formic acid and sulfuric acid, the oxidation is performed by oxidizing the compound of formula I in the presence of about 12 molar equivalents or less, about 10 molar equivalents or less, about 8 molar equivalents or less, about 7 molar equivalents or less, about 6 molar equivalents or less, about 4 molar equivalents or less, about 3 molar equivalents or less, about 2 molar equivalents or less, or about 1 molar equivalents (e.g., 1.05 molar equivalents) or less of total acid per one molar equivalent of the compound of formula I, wherein from about 0.1 to about 1.5 molar equivalents of total acid comes from the acid $H^+{}_nX^{n-}$. In one particular embodiment, the compound of formula I is oxidized to the compound of formula V by exposing each molar equivalent of the compound of formula I to (i) from about 1.0 to about 1.6 molar equivalents of hydrogen peroxide, (ii) from about 0.3 to about 9, from about 0.5 to about 8, or from about 0.5 to about 4 molar equivalents of the acid used for generating the peracid, and (iii) from about 0.1 to about 1.5, from about 0.25 to about 0.9, or from about 0.4 to about 0.6 molar equivalents of the acid $H^+{}_nX^{n-}$. In certain embodiments, from about 2.5 to about 4 molar equivalents of the acid used for generating the peracid per one molar equivalent of the compound of formula I are used. In certain embodiments, from about 0.4 to about 0.6 molar equivalents of the acid $H^+{}_nX^{n-}$, and from about 2.5 to about 4 molar equivalents of the acid used for generating the peracid are used. In certain embodiments, from about 0.4 to about 0.6 molar equivalents of the acid $H^+{}_nX^{n-}$, and from about 1 to about 3 molar equivalents of the acid used for generating the peracid are used. In certain embodiments, conducting the oxidation reaction under these conditions may improve the volume efficiency of the reaction and may reduce the number and amounts of by-products formed during the oxidation reaction.

In certain embodiments, a portion or all of the $H^+{}_nX^{n-}$ (e.g., $H_2SO_4$) is added to the reaction mixture before the acid or the peroxide used for generating the peracid is added, or at the same point in time.

In certain embodiments, $H^+{}_nX^{n-}$ (e.g., $H_2SO_4$) is added after the acid used for generating the peracid (e.g., formic acid). In certain embodiments, the reaction mixture may already comprise formic acid, and sulfuric acid is then added.

In preferred embodiments, the compound of formula V is precipitated from the reaction mixture, either because the presence of the acid $H^+{}_nX^{n-}$ (e.g., $H_2SO_4$) induces the precipitation of the compound of formula V or a solvate thereof during the oxidation reaction, or because in addition to said presence the precipitation is started or enhanced by other measures, e.g., by adjusting the temperature of the solution and/or adding a suitable antisolvent to the solution, as described in more detail below. In certain embodiments, precipitation is achieved by adding a suitable antisolvent. In certain embodiments, precipitation is achieved by lowering the temperature below the reaction temperature of the oxidation reaction. The pH of the reaction mixture at this reaction stage is generally acidic (e.g., a pH of less than about 2). It is therefore unexpected that in the presence of the $H^+_nX^{n-}$ in the reaction mixture precipitation of the compound of formula V or solvate thereof may take place.

The reaction steps (a) and (b) are typically performed in a solvent.

In certain embodiments, the oxidizing agent is or comprises performic acid generated, e.g., from hydrogen peroxide and formic acid, and the solvent is an alcohol, a mixture of two or more alcohols, or a mixture of an alcohol and water. The solvent may be methanol or a mixture of methanol and water. The solvent may be isopropanol or a mixture of isopropanol and water. The solvent may be water.

In certain embodiments, the oxidizing agent is or comprises performic acid and persulfuric acid generated, e.g., from hydrogen peroxide and formic acid and sulfuric acid, and the solvent is an alcohol, a mixture of two or more alcohols, or a mixture of an alcohol and water. The solvent may be methanol or a mixture of methanol and water. The solvent may be isopropanol or a mixture of isopropanol and water. The solvent may be water.

In certain embodiments, the oxidizing agent is or comprises peracetic acid, and the solvent is water, an alcohol, a mixture of two or more alcohols, or a mixture of an alcohol and water.

In certain embodiments, the process is for preparing 14-hydroxycodeinone (as compound of formula II) from thebaine (as compound of formula I) and step (a) is performed with an oxidizing agent formed from an acid and hydrogen peroxide. In certain embodiments, the amount of total acid present in the reaction mixture is about 12 molar equivalents or less, about 10 molar equivalents or less, about 8 molar equivalents or less, about 7 molar equivalents or less, about 6 molar equivalents or less, about 4 molar equivalents or less, about 3 molar equivalents or less, about 2 molar equivalents or less, or about 1 molar equivalents (e.g., 1.05 molar equivalents) or less per molar equivalent of thebaine. In one particular embodiment, the thebaine is oxidized to the 14-hydroxycodeinone moiety of formula V or a solvate thereof by exposing each molar equivalent of the thebaine to from about 1.0 to about 1.6 molar equivalents of hydrogen peroxide, from about 0.3 to about 9 molar equivalents, or from about 0.5 to about 8 molar equivalents of formic acid, and from about 0.4 to about 0.6 molar equivalents of sulfuric acid. In certain embodiments, from about 0.5 to about 5 molar equivalents of formic acid per one molar equivalent of thebaine are used. In certain embodiments, from about 2.5 to about 4 molar equivalents of formic acid per one molar equivalent of thebaine are used.

In certain embodiments, the process is for preparing 14-hydroxycodeinone (as compound of formula II) from thebaine (as compound of formula I) and is performed by: (i) forming a solution or a suspension comprising thebaine and from about 1.5 to about 4 molar equivalents of a first acid (e.g., formic acid) per molar equivalent of thebaine, (ii) adding from about 0.4 to about 0.6 molar equivalents of the acid $H^+_nX^{n-}$ (e.g., sulfuric acid) per molar equivalent of thebaine to the solution or the suspension, (iii) adding from about 1 to about 1.6 molar equivalents of hydrogen peroxide to the solution or the suspension from (ii), and (iv) precipitating the 14-hydroxycodeinone salt of formula V from the solution or suspension (e.g., by adjusting the temperature of the solution and/or adding a suitable antisolvent to the solution, as described in more detail below). In certain embodiments, precipitation is achieved by adding a suitable antisolvent. In certain embodiments, precipitation is achieved by lowering the temperature below the reaction temperature of the oxidation reaction.

In certain embodiments, the amount of compounds of formula III in the reaction product containing the compound of formula V is less than about 2500 ppm, less than about 2000 ppm, less than about 1500 ppm, less than about 1000 ppm, less than about 500 ppm, less than about 100 ppm, less than about 50 ppm, less than about 10 ppm, less than about 5 ppm, or less than about 1 ppm of the compound of formula V. In certain embodiments, the amount of compounds of formula III in the reaction product containing the compound of formula V is the amount described in Section III. In certain embodiments, the reaction product is free from compounds of formula III.

In certain embodiments, thebaine is oxidized to 14-hydroxycodeinone, wherein the reaction mixture comprises more than one acid (e.g., two acids), and comprises less than about 14 molar equivalents of total acid per molar equivalent of thebaine (e.g., from about 0.5 to about 11, from about 1 to about 10.5, or from about 1.5 to about 5 molar equivalents of acid per molar equivalent of thebaine).

In certain embodiments of the process, thebaine is oxidized to 14-hydroxycodeinone in a solution or suspension containing a mixture of formic acid and sulfuric acid, the mixture comprising not more than about 14 molar equivalents of total acid per one molar equivalent of thebaine (e.g., from about 0.5 to about 11, from about 1 to about 10.5, or from about 1.5 to about 5 molar equivalents of acid per one molar equivalent of thebaine).

There are also alternative ways to perform step (b) than by adding $H^+_nX^{n-}$ to the reaction mixture. In step (b) of the process, the $H^+_nX^{n-}$ can be generated by adding a salt containing $X^{n-}$. Said salt may have the formula

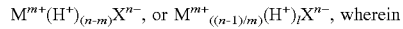

$M^{m+}$ is a monovalent or polyvalent metal cation;
m and n are independently from each other an integer selected from 1, 2, and 3, provided that m is ≤n; and
l is an integer selected from 0, 1, and 2, provided that 1<n.

The metal cation may be an alkali metal cation, an alkaline earth metal cation or a Group III cation. Exemplary cations are $Na^+$, $K^+$, $Ca^{2+}$. Exemplary salts are $NaHSO_4$, $KHSO_4$, $Na_2SO_4$, $K_2SO_4$, $NaH_2PO_4$, $Na_2HPO_4$, $Na_3PO_4$, $KH_2PO_4$, $K_2HPO_4$, $K_3PO_4$.

As a further alternative to adding an acid $H^+_nX^{n-}$ in step (b), step (b) may be performed by adding a Lewis acid to the reaction mixture instead of the acid $H^+_nX^{n-}$. Such Lewis acid may be aluminum chloride ($AlCl_3$), aluminum bromide ($AlBr_3$), boron trifluoride ($BF_3$), boron trifluoride diethyl etherate ($BF_3.Et_2O$), iron(III) chloride ($FeCl_3$) or the like.

The oxidation reaction may be prepared in any suitable reaction vessel. In certain embodiments, the reaction vessel is a flow reactor. In certain other embodiments, the reaction vessel is not a flow reactor. In certain embodiments, the reaction vessel is a continuous flow reactor. In certain other embodiments, the reaction vessel is not a continuous flow reactor.

Precipitation and/or Isolation of the Compound of Formula V

The compound of formula V according to present invention or the solvate thereof may be provided as a solid, or in solution or suspension as a result of the process encompassing steps (a) and (b). In certain preferred embodiments, the process is performed under conditions wherein the compound of formula V or a solvate thereof is insoluble in the reaction mixture. In these embodiments, the process may comprise an additional step (c) of precipitating the compound of formula V or the solvate thereof from the reaction mixture.

As already pointed out in the Definitions section, "precipitating" encompasses "crystallizing" unless stated otherwise.

The precipitation of the compound of formula V or the solvate thereof is considered to be surprising because of the acidic pH of the reaction mixture.

The precipitation may start as soon as $H^+{}_n X^{n-}$ is present in the reaction mixture (e.g., after addition of an acid $H^+{}_n X^{n-}$), or it may start at a later point in time. In other words, it may take place during and/or after the oxidation reaction.

The precipitation of the compound of formula V or the solvate thereof may be caused by the presence of the acid $H^+{}_n X^{n-}$ in the reaction mixture. It may be enhanced by adding an additional amount of the acid $H^+{}_n X^{n-}$ or the salt containing $X^{n-}$ to the reaction mixture during step (b).

In certain embodiments, the precipitation of the compound of formula V or the solvate thereof may require the cooling of the reaction mixture and/or the addition of an antisolvent.

In certain embodiments wherein the compound of formula V or a solvate thereof precipitates from the reaction mixture, the acid $H+{}_n X^{n-}$ is $H_2SO_4$ or its monosalt, methanesulfonic acid, tosylic acid, trifluoroacetic acid, $H_3PO_4$ or one of its mono- or disalts, oxalic acid, perchloric acid, or any mixtures thereof. In certain embodiments, it may be $H_2SO_4$, methanesulfonic acid, tosylic acid, trifluoroacetic acid, or a mixture thereof. In certain embodiments, it is $H_2SO_4$, methanesulfonic acid, or trifluoroacetic acid or a mixture thereof. In certain embodiments, it is trifluoroacetic acid. In certain embodiments, it is $H_2SO_4$. In certain embodiments, it is methanesulfonic acid.

The compound of formula V or the solvate thereof, once precipitated, may either be isolated (i.e. separated from the reaction mixture), or it may be converted without preceding isolation to further compounds, e.g., to a compound of formula IV or a salt or solvate thereof.

Once precipitated and isolated, the precipitate containing the compound of formula V may, optionally, be subject to one or more further steps to reduce the amount of any residual compound of formula III therein (e.g., (re)crystallization or heat treatment) which are described in the subsequent section.

Precipitation of the compound of formula V may be influenced by the molar ratio of the anion $X^{n-}$ to the compound of formula I (see above), by the amount of total acid present during the oxidation reaction (as compared to molar equivalents of the compound of formula I), by the temperature before, during or after the oxidation reaction, by the amount of solvent (e.g., water) present in the reaction mixture, by the presence of an antisolvent added to the reaction mixture, by the rate at which the reactants are added during the process to the reaction mixture, or by a combination of any of the foregoing.

In certain embodiments, the precipitation of the compound of formula V or a solvate thereof is initiated and/or enhanced by one or more of the following:
(i) adjusting (e.g., lowering) the temperature of the reaction mixture to the precipitation temperature;
(ii) addition of an antisolvent;
(iii) addition of a seed crystal;
(iv) lowering the pH;
(v) changing the ionic strength of the reaction mixture (e.g., by addition of a salt);
(vi) concentrating the reaction mixture;
(vii) reducing or stopping agitation of the reaction mixture; or any other conventional method for initiating or enhancing precipitation or crystallization.

When the temperature is adjusted to the precipitation temperature, this means that the precipitation of the compound of formula V or the solvate thereof is initiated and/or enhanced by adjusting the temperature of the reaction mixture to or beyond a temperature at which said compound precipitates ("precipitation temperature"). The temperature is either adjusted by performing the reaction at the precipitation temperature, or by lowering the temperature of the reaction mixture during the reaction or after completion of the reaction.

In certain embodiments, the reaction mixture is adjusted to a temperature of ≤40° C. to initiate precipitation, i.e. the precipitation temperature is ≤40° C. In certain embodiments, the precipitation is initiated at a precipitation temperature of about −20° C., about −15° C., about −10° C., about −5° C., about 0° C., about 5° C., about 10° C., about 15° C., about 17° C., about 19° C., about 21° C., about 23° C., about 25° C., about 27° C., about 29° C., about 31° C., about 33° C., about 35° C., about 37° C., or about 40° C.

In certain embodiments, the precipitation temperature is in a range of from about −20° C. to about 40° C., preferably from about 0° C. to about 40° C., more preferably from about 5° C. to about 35° C., more preferably from about 5° C. to about 30° C., even more preferably from about 5° C. to about 20° C.

In certain embodiments, the precipitation temperature is in a range of from about 5° C. to about 22° C., preferably from 5° C. to about 18° C., more preferably from about 8° C. to about 15° C.

In certain embodiments, the precipitation temperature is in a range of from about 5° C. to about 18° C.; or from about 8° C. to about 15° C.

In certain embodiments, e.g., in certain embodiments wherein the compound of formula V is 14-hydroxycodeinone sulfate, an antisolvent is used in addition to adjusting the temperature to the precipitation temperature.

If an antisolvent is used for initiating precipitation, the precipitation temperature may be in a range of from about −20° C. to about 40° C., from about 0° C. to about 40° C., from about 5° C. to about 35° C., from about 5° C. to about 22° C., from about 5° C. to about 18° C.; or from about 8° C. to about 15° C.

In certain embodiments, the reaction mixture is cooled at a controlled rate during precipitation. In certain embodiments, the cooling rate is about 1° C., about 2° C., about 3° C., about 4° C., or about 5° C. per hour.

An important factor influencing the precipitation of a compound of formula V or a solvate thereof in a process according to present invention may be the temperature of the reaction mixture. A further factor influencing the precipitation appears to be the total amount of acid in the reaction mixture. Another factor influencing the precipitation appears to be the molarity of the reaction mixture. The addition of an antisolvent also appears to be a factor that can influence precipitation of a compound of formula V or a solvate thereof, e.g., the precipitation of 14-hydroxycodeinone sulfate. It is presently believed that the precipitation temperature will rise when the total amount of acid is lowered.

Hence, in a process wherein the compound of formula V or the solvate thereof is precipitated and wherein the total amount of acid present in the reaction mixture is from about 0.6 to about 14.0 molar equivalents of total acid per molar equivalent of the compound of formula I, the precipitation temperature may be ≤40° C. (i.e. 40° C. or less). In a process wherein the total amount of acid present in the reaction mixture is from about 1 to about 8 molar equivalents, preferably from about 1 to about 5 molar equivalents of total acid per molar equivalent of the compound of formula I, the precipitation temperature may be in a range of from about 0° C. to about 40° C., preferably from about 0° C. to about 35° C. In a process wherein the total amount of acid present in the reaction mixture is from about 1 to about 4 molar equivalents, preferably from about 1 to about 3 molar equivalents of total acid per molar equivalent of the compound of formula I, the precipitation temperature may be in a range of from about 5° C. to about 22° C.; preferably from about 8° C. to about 20° C.

In certain embodiments, an antisolvent is added to precipitate a compound of formula V or a solvate thereof, e.g., 14-hydroxycodeinone sulfate or a solvate thereof. When an antisolvent is added to the reaction mixture, it is added either during or after step (b) and in an effective amount to initiate and/or enhance precipitation. In certain embodiments, addition of a suitable antisolvent increases the yield of the reaction. A suitable antisolvent may comprise or consist of tert-butyl methyl ether, diethyl ether, hexane(s), tert-amyl alcohol, methanol, ethanol, isopropanol, 2-butanol, heptanes, xylenes, toluene, acetone, 2-butanone, ethyl acetate, tetrahydrofuran, 1,2-dichloroethane, chloroform, dichloromethane, 1-methoxy-2-propanol, 2-ethoxyethanol, n-propanol, I-butanol, tert-butanol, isobutanol, isopropyl acetate, 1,4-dioxane, 2-methyl-tetrahydrofuran, methyl formate, methyl acetate, or a mixture of two or more of any of the foregoing. 14-Hydroxycodeinone sulfate has very low/no solubility in these solvents at room temperature. The listed alcohols and ethers are the preferred antisolvents. In some embodiments, said antisolvent is an alcohol, e.g., methanol. In some embodiments, said antisolvent is an ether, e.g., tert-butyl methyl ether and/or tetrahydrofuran. In some embodiments, said antisolvent is a mixture of an alcohol (e.g., methanol) and an ether (e.g., tert-butyl methyl ether and/or tetrahydrofuran), for example a mixture of methanol and tert-butyl methyl ether, or a mixture of methanol and tetrahydrofuran, or a mixture of tert-butyl methyl ether and tetrahydrofuran, or a mixture of methanol, tert-butyl methyl ether, and tetrahydrofuran. When two or more antisolvents are used (e.g., in a mixture), they can be added as a mixture or separately.

When a seed crystal is added, said seed crystal is a crystal of the compound of formula V or a solvate thereof. This seed crystal may act as crystallization nucleus if the solution of the compound of formula V resulting from step (b) is metastable. It may be made metastable by concentrating the reaction mixture.

In certain embodiments, the precipitate may be isolated from the reaction mixture (isolation step (d)).

In said isolation step (d), the precipitate may be separated from the supernatant in any conventional manner, e.g., by filtration, centrifugation, decanting, or any other conventional method for separating a solid phase from a liquid phase. In certain embodiments, the ratio of compounds of formula III (e.g., of 8-hydroxyoxycodone) (either in its free base form or bound in a salt or solvate) to that of formula II (which may be bound in the compound of formula V) in the precipitate is less than the ratio of compounds of formula III (e.g., of 8-hydroxyoxycodone) to that of formula II in the supernatant.

In cases where the compound of formula V or a solvate thereof is not precipitated, it may be isolated by concentrating the reaction mixture, e.g., by drying, vacuum distillation, spray drying or lyophilization.

Further Processing of the Compound of Formula V or the Solvate Thereof

In certain embodiments, the precipitate containing the compound of formula V or the solvate thereof can be further processed.

In certain embodiments, the isolated precipitate containing the compound of formula V or the solvate thereof is treated with a substance that converts a portion or all or substantially all of the compound of formula III contained in said precipitate into a compound of formula II, a salt of a compound of formula II (e.g., into the compound of formula V), or a compound which will not be converted into the compound of formula II during further processing of the composition.

In certain embodiments, the isolated precipitate containing the compound of formula V or the solvate thereof is hydrogenated. Generally, the hydrogenation is conducted under conditions which are less severe than the hydrogenation conditions described below for the preparation of a compound of formula IV or a salt or solvate thereof. For example, less acid may be required for the hydrogenation of the compound of formula V or the solvate thereof.

In certain embodiments, the isolated precipitate containing the compound of formula V or the solvate thereof is heated to further reduce the amount of a compound of formula III or salt or solvate thereof in the composition.

In certain embodiments, the isolated precipitate containing the compound of formula V or solvate thereof may be washed with and/or (re)crystallized in an organic solvent or aqueous solvent in which a compound of formula III or a salt or solvate thereof is more soluble than the compound of formula V or solvate thereof and/or the corresponding compound of formula II. The washing and/or (re)crystallization may further reduce the amount of a compound of formula III in the isolated precipitate containing the compound of formula V or solvate thereof. The washing and/or the (re)crystallization may be performed more than once, or they may also be combined sequentially.

In certain embodiments, the isolated precipitate containing the compound of formula V or solvate thereof is washed with and/or is (re)crystallized in a solvent containing or consisting of an ether, a ketone, an ester, an alcohol, water, an (optionally halogenated) alkane, an (optionally halogenated) aromatic solvent or any mixtures thereof. The solvent may contain or consist of one or more of the following solvents: methanol, ethanol, isopropanol, acetone, tetrahydrofuran, ethyl acetate, heptane, tert-butyl methyl ether, 1,2-dichloroethane, toluene, 2-butanone (MEK), tert-amyl alcohol, chloroform, xylene, and water.

In certain embodiments, the isolated precipitate containing the compound of formula V or solvate thereof is washed and/or (re)crystallized in a solvent consisting of an ether, an alcohol, water, chloroform, or any mixture thereof. In certain embodiments, said solvent may be methanol, ethanol, n-propanol, isopropanol, butanol, isobutanol, tert-butanol, acetone, tetrahydrofuran, chloroform, or a mixture of water with any of the foregoing.

In certain embodiments, the isolated precipitate containing the compound of formula V or solvate thereof is washed and/or (re)crystallized with a solvent which is tert-butyl methyl ether, tetrahydrofuran, methanol, ethanol, acetone, isopropanol, or a mixture of methanol:water, THF:water, acetone:water, isopropanol:water, or ethanol:water. In certain embodiments, the isolated precipitate containing the compound of formula V or solvate thereof is washed and/or (re)crystallized with a solvent which is tert-butyl methyl ether, tetrahydrofuran, methanol, or a methanol:water mixture.

In certain embodiments, preferably wherein the compound of formula V is 14-hydroxycodeinone sulfate and the compound of formula III is 8-hydroxyoxycodone, the isolated precipitate containing the compound of formula V or solvate thereof is washed with and/or (re)crystallized in a 90:10 methanol:water mixture; 80:20 methanol:water mixture, 70:30 methanol:water or 60:40 methanol:water mixture. In certain embodiments, the isolated precipitate containing the compound of formula V or solvate thereof is washed with and/or (re)crystallized in a 80:20 or 70:30 methanol:water mixture. 8-Hydroxyoxycodone (and its corresponding protonated species) is more soluble in these mixtures than 14-hydroxycodeinone sulfate and therefore it is assumed that a compound of formula III may be removed from the isolated compound of formula V or solvate thereof by the washing and/or (re)crystallization.

In certain embodiments, preferably wherein the compound of formula V is 14-hydroxycodeinone sulfate and the compound of formula III is 8-hydroxyoxycodone, the isolated precipitate containing the compound of formula V or solvate thereof is washed with and/or (re)crystallized in a 90:10 ethanol:water mixture, 80:20 ethanol:water mixture or 70:30 ethanol:water mixture. In certain embodiments, the isolated precipitate containing the compound of formula V or solvate thereof is washed with and/or (re)crystallized in 90:10 ethanol/water mixture. 8-Hydroxyoxycodone (and its corresponding protonated species) is more soluble in these mixtures than 14-hydroxycodeinone sulfate and therefore it is assumed that a compound of formula III may be removed from the isolated compound of formula V or solvate thereof by the washing and/or (re)crystallization.

In certain embodiments, preferably wherein the compound of formula V is 14-hydroxycodeinone sulfate and the compound of formula III is 8-hydroxyoxycodone, the isolated precipitate containing the compound of formula V or solvate thereof is washed with and/or (re)crystallized in tetrahydrofuran or in 90:10 tetrahydrofuran:water mixture. 8-Hydroxyoxycodone (and its corresponding protonated species) is more soluble in these mixtures than 14-hydroxycodeinone sulfate and therefore it is assumed that a compound of formula III may be removed from the isolated compound of formula V or solvate thereof by the washing and/or (re)crystallization.

In certain embodiments, preferably wherein the compound of formula V is 14-hydroxycodeinone sulfate and the compound of formula III is 8-hydroxyoxycodone, the isolated precipitate containing the compound of formula V or solvate thereof is washed with and/or (re)crystallized in a 90:10 isopropanol:water mixture, 80:20 isopropanol:water mixture or 70:30 isopropanol mixture. In certain embodiments, the isolated precipitate containing the compound of formula V or solvate thereof is washed with and/or (re)crystallized in a 90:10 isopropanol:water mixture. 8-Hydroxyoxycodone (and its corresponding protonated species) is more soluble in these mixtures than 14-hydroxycodeinone sulfate and therefore it is assumed that a compound of formula III may be removed from the isolated compound of formula V or solvate thereof by the washing and/or (re)crystallization.

In certain embodiments, preferably wherein the compound of formula V is 14-hydroxycodeinone sulfate and the compound of formula III is 8-hydroxyoxycodone, the isolated precipitate containing the compound of formula V or solvate thereof is washed with and/or (re)crystallized in a 70:30 acetone:water mixture or 80:20 acetone:water mixture. 8-Hydroxyoxycodone (and its corresponding protonated species) is more soluble in these mixtures than 14-hydroxycodeinone sulfate and therefore it is assumed that a compound of formula III may be removed from the isolated compound of formula V or solvate thereof by the washing and/or (re)crystallization.

The washing of the isolated precipitate containing the compound of formula V or solvate thereof may be performed in any way conventional in the art, e.g., by forming a slurry of the compound.

The precipitate containing the compound of formula V or solvate thereof, whether isolated or not isolated, may be treated with a suitable acid to effect conversion of a compound of formula III or salt thereof, if present, to ultimately a compound of formula V. In general, any acid known to be capable of converting a β-hydroxy-ketone to an α,β-unsaturated ketone, under the conditions of the prior art, may be used. A suitable Lewis acid may be, e.g., aluminum chloride ($AlCl_3$), aluminum bromide ($AlBr_3$), boron trifluoride ($BF_3$), boron trifluoride diethyl etherate ($BF_3.Et_2O$), iron(III) chloride ($FeCl_3$) or the like. A suitable Bronsted acid may be, e.g., the acid $H^+_n X^{n-}$, ethanedioic acid, acetic acid, paratoluene sulfonic acid, a mineral acid or the like.

The precipitate containing the compound of formula V or solvate thereof, whether isolated or not, may also be treated with a dehydrating reagent(s), e.g., oxalic acid ($H_2C_2O_4$) or oxalyl chloride $(COCl)_2$, phosphorous trichloride ($PCl_3$), phosphoryl trichloride ($POCl_3$), thionyl chloride ($SOCl_2$), sulfuryl chloride ($SO_2Cl_2$), or the like, under suitable conditions to effect conversion of a compound of formula III or salt thereof, if present, to ultimately a compound of formula V.

The precipitate containing the compound of formula V or solvate thereof may also be treated with an oxidizing agent, e.g., potassium permanganate ($KMnO_4$), chromium(VI) oxide ($CrO_3$), DMF-Cl, $(CH_3)_2SCl$, or the like, under suitable conditions to effect oxidation of any compound of formula III or salt thereof, if present.

In certain embodiments, the amount of any compound of formula III or salt thereof in a product containing the compound of formula V or solvate thereof prepared by a process comprising the step of precipitating and isolating the compound of formula V or solvate thereof as described herein is less than the corresponding amount of the compound of formula III or salt thereof in a product containing the corresponding compound of formula II prepared by a processes which does not include the formation and isolation of a compound of formula V or solvate thereof.

In certain embodiments, the ratio of compound of formula III to compound of formula V in the supernatant after the precipitation of the compound of formula V or solvate thereof is higher than the ratio of compound of formula III to compound of formula V in the precipitate.

III. Levels of the Compound of Formula III in the Product Containing Compound of Formula V Resulting from the Process According to Section II Thus, the present invention provides a process for preparing a compound of formula V or a solvate thereof as represented in Scheme 15:

Scheme 15

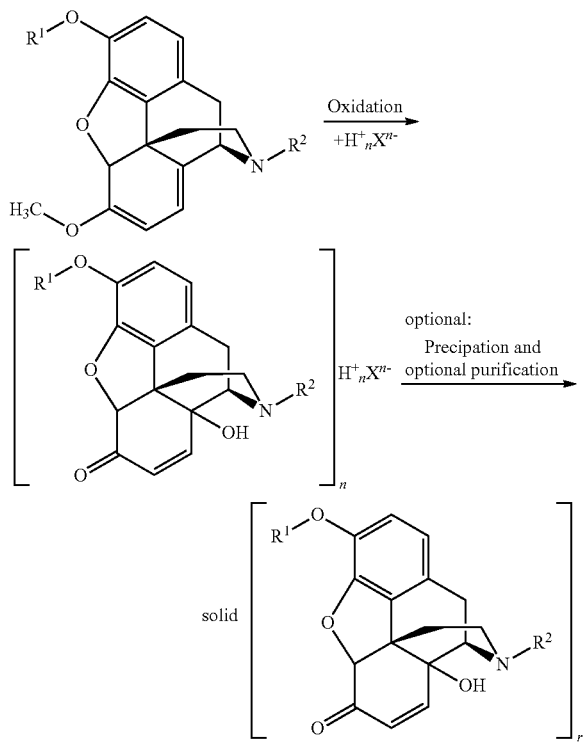

The product of the process is the compound of formula V or a solvate thereof in its dissolved (unprecipitated) or solid (precipitated (e.g., crystallized)), and optionally further processed form.

The product of the process may contain a compound of formula III or salt thereof as a by-product of the oxidation reaction, as illustrated in the following reaction Scheme 16:

Scheme 16

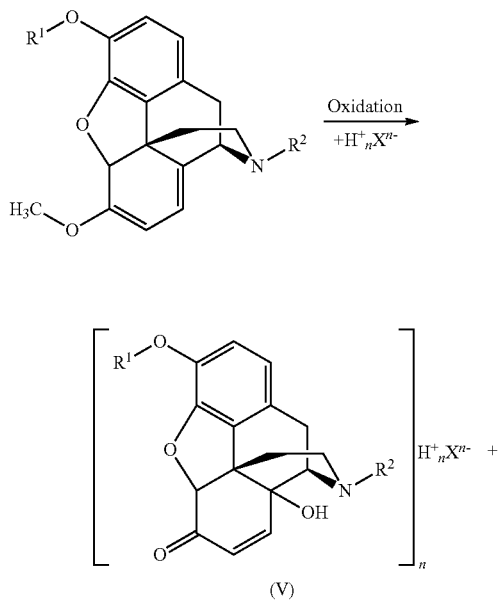

-continued

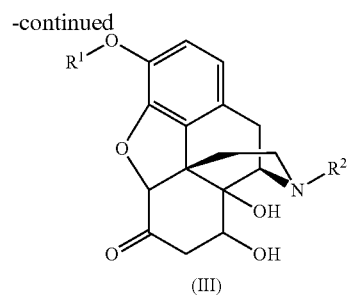

Said compound of formula III may be present in the product in the form of its free base, or in the form of its salt or solvate. Under the acid conditions of the oxidation reaction according to the present invention, it is typically present in its protonated form and will therefore form a salt or a solvate thereof.

Said compound of formula III may be present in the reaction mixture at the end of the process in dissolved or precipitated form. In embodiments where the compound of formula V is precipitated, said compound of formula III may be present in the precipitate, in the mother liquor, or in both.

Hence, the present invention also provides a process for preparing a composition comprising a compound of formula V or a solvate thereof, and a compound of formula III or a salt or solvate thereof as a by-product. The embodiments for performing said process are described in Section II.

Whenever compound of formula III is comprised in the process product (which is a composition as defined in the preceding paragraph), it is present in a certain amount which shall be specified in the following.

In certain embodiments, the amount of the compound of formula III or salt or solvate thereof which is present in the process product is less than the amount of the compound of formula III or salt or solvate thereof which is present in a product of the same process performed in the absence of the acid $H^+{}_nX^{n-}$.

In certain embodiments, the process product containing the compound of formula V or a solvate thereof contains an amount of formula III or a salt or solvate thereof which is less than the amount of the compound of formula III or salt or solvate thereof which would be present in a process product containing the corresponding compound of formula II or salt or solvate thereof prepared by the process in the absence of the acid $H^+{}_nX^{n-}$.

In certain embodiments, the compound of formula V or solvate thereof is precipitated during the process and the precipitate contains less compound of formula III or salt or solvate thereof in relation to compound of formula V or solvate thereof than the mother liquor.

In certain embodiments, the amount of the compound of formula III or salt or solvate thereof in the process product containing the compound of formula V or solvate thereof is less than about 2500 ppm, less than about 2250 ppm, less than about 2000 ppm, less than about 1750 ppm, less than about 1500 ppm, or less than about 1250 ppm of the compound of formula V (HPLC peak area ratio).

In certain embodiments, the amount of the compound of formula III or salt or solvate thereof in the process product containing the compound of formula V or solvate thereof is less than about 1000 ppm, less than about 750 ppm, less than about 500 ppm, or less than about 400 ppm of the compound of formula V or solvate thereof (HPLC peak area ratio).

In certain embodiments, the amount of the compound of formula III or salt or solvate thereof in the process product containing the compound of formula V or solvate thereof is less than about 300 ppm, less than about 275 ppm, less than about 250 ppm, less than about 225 ppm, less than about 200 ppm, less than about 175 ppm, less than about 150 ppm, or less than about 125 ppm of the compound of formula V or solvate thereof (HPLC peak area ratio).

In certain embodiments, the amount of the compound of formula III or salt or solvate thereof in the process product containing the compound of formula V or solvate thereof is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm of the compound of formula V or solvate thereof (HPLC peak area ratio).

In certain embodiments, the amount of the compound of formula III or salt or solvate thereof in the process product containing the compound of formula V or solvate thereof is less than about 10 ppm, less than about 8 ppm, less than about 6 ppm, less than about 4 ppm, or less than about 2 ppm of the compound of formula V or solvate thereof (HPLC peak area ratio).

In certain embodiments, the amount of the compound of formula III or salt or solvate thereof in the process product containing the compound of formula V or solvate thereof is less than about 1 ppm, less than about 0.8 ppm, less than about 0.6 ppm, less than about 0.4 ppm, less than about 0.3 ppm, less than about 0.2 ppm, or less than about 0.1 ppm of the compound of formula V or solvate thereof (e.g., the amount of 8-hydroxyoxycodone is from about 0.05 ppm to about 0.7 ppm of the 14-hydroxycodeinone sulfate) (HPLC peak area ratio).

The amount of the compound of formula III or salt or solvate thereof in the process product containing the compound of formula V or solvate thereof may have a lower limit of about 0.01 ppm of the compound of formula V or solvate thereof (HPLC peak area ratio). The lower limit may also be about 0.05 ppm, about 0.1 ppm, about 0.3 ppm, about 0.5 ppm, about 0.7 ppm, about 1 ppm, about 1.5 ppm, about 2 ppm, or about 3 ppm. For example, the amount of the compound of formula III or salt or solvate thereof in the compound of formula V or salt or solvate thereof may range from about 0.05 ppm to 1 ppm in a certain embodiment, and from about 1 ppm to about 10 ppm in a certain other embodiment.

The process product containing the compound of formula V or solvate thereof in certain embodiments comprises from about 0.01 ppm to about 2500 ppm, from about 0.05 to about 2250 ppm, from about 0.1 ppm to about 2000 ppm, from about 0.3 to about 1750 ppm, from about 0.5 ppm to about 1500 ppm, or from about 1 ppm to about 1250 ppm compound of formula III or a salt or solvate thereof in relation to the compound of formula V (HPLC peak area ratio).

The process product containing the compound of formula V or solvate thereof in certain embodiments comprises from about 0.05 ppm to about 1000 ppm, from about 0.1 ppm to about 800 ppm, from about 0.1 ppm to about 700 ppm, from about 0.2 ppm to about 600 ppm, from about 0.3 ppm to about 500 ppm, or from about 0.5 ppm to about 400 ppm compound of formula III or salt or solvate thereof in relation to the compound of formula V.

The process product containing the compound of formula V or solvate thereof in certain embodiments comprises from about 0.05 ppm to about 350 ppm, from about 0.1 ppm to about 300 ppm, from about 0.2 ppm to about 275 ppm, from about 0.3 ppm to about 250 ppm, from about 0.4 ppm to about 225 ppm, or from about 0.5 ppm to about 200 ppm compound of formula III or salt or solvate thereof in relation to compound V.

In certain embodiments, the process product containing the compound of formula V comprises the 8α stereoisomer, the 8β stereoisomer, or a mixture of these two stereoisomers of a compound of formula III. In said embodiments, less 8α and/or less 8β stereoisomer may be present than in a process product which has been formed in the absence of the acid $H^+{}_nX^{n-}$. In one embodiment, the compound of formula V is a (14-hydroxycodeinone)salt (e.g., 14-hydroxycodeinone sulfate), and the compound of formula III may be 8-hydroxyoxycodone having 8α and/or 8β stereoconfiguration.

As already indicated in Section II, in certain embodiments of the oxidation process according to the present invention said result may be achieved because the formation of the compound of formula V or a solvate thereof has the effect that less 8-hydroxy compound of formula III is formed during the oxidation reaction in comparison to an oxidation reaction where no compound of formula V or solvate thereof is formed. In other words, the formation of the compound of formula V allows for an improvement of the by-product profile of the reaction product. One example for such embodiment may be the formation of a compound of formula V wherein n is 2 and preferably wherein $X^{n-}$ is sulfate. Another example for such embodiment may be the formation of a compound of formula V wherein n is 1 and preferably wherein $X^{n-}$ is trifluoroacetate.

In certain other embodiments of the oxidation process according to the present invention said result may be achieved because the formation of formula V or a solvate thereof has the effect that compounds of formula III can be separated from the compound of formula V or the solvate thereof, e.g., by precipitation of the compound of formula V or the solvate thereof from the reaction mixture. One example for such an embodiment may be the formation of a compound of formula V wherein $X^{n-}$ is sulfate.

In certain embodiments a combination of these effects takes place. That is, said result is achieved because both less compounds of formula II are formed during the oxidation and because said compounds of formula III can be separated from the compound of formula V or solvate thereof. One example for such an embodiment may be the formation of a compound of formula V wherein $X^{n-}$ is sulfate.

IV. Compound Having the Formula V

The present invention further provides a compound having the formula V or a solvate thereof

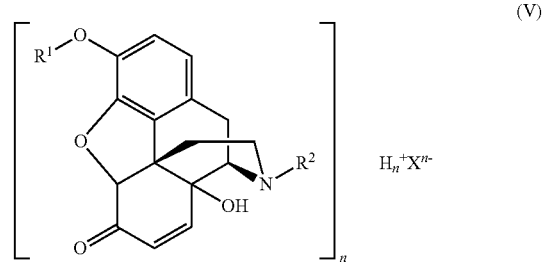

(V)

wherein $R^1$, $R^2$, $X^{n-}$ and n are defined as above, in particular in section I. Present invention provides said compound of formula V or solvate thereof as a solid, in solution or as a suspension.

The compound of formula V or solvate thereof comprises one or more protonated molecules of formula II and at least one anion X$^{n-}$. The anion may be an organic or inorganic anion. The anion may be mono- or polyvalent (e.g., divalent or trivalent). In its solid form, the components of the compound of formula V are present in stoichiometric amounts. However, other molecular ratios may also be present either in micro- or macrostructures of the salt, depending e.g., on the type of the anion and valency thereof, the solvent (which might also form part of the salt) and the ambient pH.

In certain embodiments, said compound of formula V or solvate thereof is provided in its isolated, solid form, which in certain embodiments is its crystalline form.

Said compound of formula V or solvate thereof may be obtainable or obtained by the process described in section II. In these embodiments, the process product may have the properties as described in section III.

Said compound of formula V or solvate thereof is an embodiment of the present invention, on its own right, and in its function as a starting material or as intermediate for the synthesis of compounds of formula IV or (pharmaceutically acceptable) salts or solvates thereof. A composition comprising said product of formula V or solvate thereof, as described in more detail in Section IV-A, is also an embodiment of the present invention on its own right, and in its function as a starting material or as intermediate for the synthesis of compounds of formula IV or (pharmaceutically acceptable) salts or solvates thereof.

In certain embodiments of the compound of formula V or solvate thereof, n is 1 or 2, and is preferably 2.

In certain embodiments, X$^{n-}$ is SO$_4^{2-}$ or trifluoroacetate, and is preferably SO$_4^{2-}$.

In certain embodiments, the compound of formula V is provided as its solvate. Said solvate may be any association product of a compound of formula V with a solvent molecule. The molar ratio of solvent molecule(s) per molecule of formula V may vary. The molar ratio of solvent to compound/salt in the solvate may be 1 (e.g., in a monohydrate), more than 1 (e.g., 2, 3, 4, 5 or 6 in a polyhydrate), or less than 1 (e.g., in a hemihydrate). The molar ratio need not be an integer ratio, it can also be, e.g., 0.5 (as in a hemihydrate) or 2.5. For example, 1 molecule water per molecule of 14-hydroxycodeinone sulfate is bound in 14-hydroxycodeinone sulfate monohydrate. The solvate of the compound of formula V is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate of the compound of formula V is a hydrate wherein the ratio of water per molecule is within the range of from 1 to 8. In certain embodiments, the solvate of the compound of formula V is a hydrate wherein the ratio of water per molecule is within the range of from 1 to 6, i.e. a mono- to hexahydrate. In certain embodiments, the solvate of the compound of formula V is a monohydrate or a pentahydrate.

In certain embodiments, R$^2$ is —CH$_3$. In other words, in these embodiments the compound of formula V is a 14-hydroxycodeinone salt or solvate thereof.

In certain embodiments, R$^2$ is —H. In other words, in these embodiments the compound of formula V is a 14-hydroxy-norcodeinone salt or solvate thereof.

In certain embodiments, the compound of formula V is

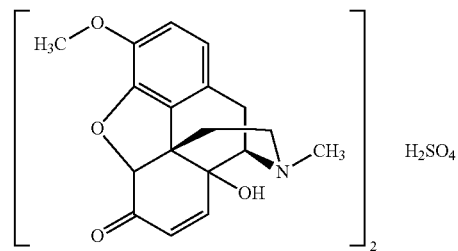

or a solvate thereof. The solvate may be a hydrate. The molar ratio of solvent to compound/salt in the solvate may be 1 (e.g., in a monohydrate), more than 1 (e.g., 2, 3, 4, 5 or 6 in a polyhydrate), or less than 1 (e.g., in a hemihydrate). The molar ratio need not be an integer ratio, it can also be, e.g., 0.5 (as in a hemihydrate) or 2.5. For example, 1 molecule water per molecule of 14-hydroxycodeinone sulfate is bound in 14-hydroxycodeinone sulfate monohydrate. The solvate is in certain embodiments a hydrate, for example a monohydrate, dihydrate, trihydrate, tetrahydrate, pentahydrate or hexahydrate, or a hydrate wherein the ratio of water per molecule is not necessarily an integer, but within the range of from 0.5 to 10.0. In certain embodiments, the solvate is a hydrate wherein the ratio of water per molecule is within the range of from 1 to 8. In certain embodiments, the solvate is a hydrate wherein the ratio of water per molecule is within the range of from 1 to 6, i.e. a mono- to hexahydrate. In certain embodiments, the solvate is a monohydrate or a pentahydrate.

In certain embodiments, the compound of formula V is not 14-hydroxycodeinone triflate, 14-hydroxycodeinone chloride, or 14-hydroxycodeinone perchlorate.

In certain embodiments, in the compound of formula V the anion X$^{n-}$ is not SO$_4^{2-}$ when R$^2$ is selected from —H, —CH$_3$, optionally unsaturated —(C$_2$-C$_6$)alkyl, and —(C$_1$-C$_4$)alkyl substituted with at least one cycloalkyl group.

The compound of formula V or solvate thereof may be used as an intermediate or starting material for preparing another opioid or salt or solvate thereof, and for preparing an API which is an opioid or a pharmaceutically acceptable salt or solvate thereof, and/or a pharmaceutical composition or dosage form containing such API.

Pharmaceutical compositions and dosage forms produced from said compound of formula V or solvate thereof, preferably, contain less compound of formula III and/or formula II than pharmaceutical compositions prepared via a different intermediate, i.e. without the compound of formula V.

Compounds and compositions which may be prepared from the compound of formula V or a solvate thereof will be described in the subsequent sections.

IV-A. Compositions Comprising Compound of Formula V

The present invention further provides a composition comprising a compound of formula V or a solvate thereof.

Said composition may be the product of the process described in Section II.

Said composition may be solid, or a suspension, or a solution. In certain embodiments, it is a solid. In certain embodiments, it is the precipitate containing the compound of formula V as described in Section IV.

In certain embodiments, the composition comprising the compound of formula V or solvate thereof additionally comprises a compound of formula III:

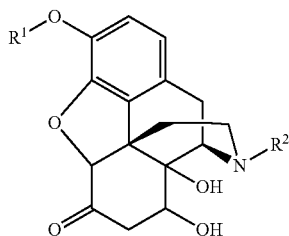

(III)

wherein R¹ and R² are defined as in the compound of formula V,
or a salt or solvate thereof.

In certain embodiments, the amount of the compound of formula III or salt or solvate thereof in the composition is the amount as described in Section III.

In certain embodiments, the amount of the compound of formula III or salt or solvate thereof in the composition is less than about 2500 ppm, less than about 2250 ppm, less than about 2000 ppm, less than about 1750 ppm, less than about 1500 ppm, or less than about 1250 ppm of the compound of formula V (HPLC peak area ratio).

In certain embodiments, the amount of the compound of formula III or salt or solvate thereof in the composition is less than about 1000 ppm, less than about 750 ppm, less than about 500 ppm, or less than about 400 ppm of the compound of formula V or solvate thereof (HPLC peak area ratio).

In certain embodiments, the amount of the compound of formula III or salt or solvate thereof in the composition is less than about 300 ppm, less than about 275 ppm, less than about 250 ppm, less than about 225 ppm, less than about 200 ppm, less than about 175 ppm, less than about 150 ppm, or less than about 125 ppm of the compound of formula V or solvate thereof (HPLC peak area ratio).

In certain embodiments, the amount of the compound of formula III or salt or solvate thereof in the composition is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm of the compound of formula V or solvate thereof (HPLC peak area ratio).

In certain embodiments, the amount of the compound of formula III or salt or solvate thereof in the composition is less than about 10 ppm, less than about 8 ppm, less than about 6 ppm, less than about 4 ppm, or less than about 2 ppm of the compound of formula V or solvate thereof (HPLC peak area ratio).

In certain embodiments, the amount of the compound of formula III or salt or solvate thereof in the composition is less than about 1 ppm, less than about 0.8 ppm, less than about 0.6 ppm, less than about 0.4 ppm, less than about 0.3 ppm, less than about 0.2 ppm, or less than about 0.1 ppm of the compound of formula V or solvate thereof (e.g., the amount of 8-hydroxyoxycodone is from about 0.05 ppm to about 0.7 ppm of the 14-hydroxycodeinone sulfate) (HPLC peak area ratio).

In certain embodiments, the compound of formula V is 14-hydroxycodeinone, and the amount of 8-hydroxyoxycodone in the composition is less than about 2500 ppm, less than about 2250 ppm, less than about 2000 ppm, less than about 1750 ppm, less than about 1500 ppm, less than about 1250 ppm, less than about 1000 ppm, less than about 750 ppm, less than about 500 ppm, less than about 400 ppm, less than about 300 ppm, or less than about 200 ppm of the 14-hydroxycodeinone sulfate (HPLC peak area ratio).

In certain embodiments, the amount of the compound of formula III or salt or solvate thereof in the composition has a lower limit of about 0.05 ppm of the compound of formula V or solvate thereof (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm. For example, the amount of the compound of formula III or salt or solvate thereof in the composition may range from about 0.05 ppm to 1 ppm in a certain embodiment, and from about 1 ppm to about 10 ppm in a certain other embodiment.

The composition in certain embodiments comprises from about 0.01 ppm to about 2500 ppm, from about 0.05 to about 2250 ppm, from about 0.1 ppm to about 2000 ppm, from about 0.3 to about 1750 ppm, from about 0.5 ppm to about 1500 ppm, or from about 1 ppm to about 1250 ppm compound of formula III or a salt or solvate thereof in relation to the compound of formula V (HPLC peak area ratio).

The composition in certain embodiments comprises from about 0.05 ppm to about 1000 ppm, from about 0.1 ppm to about 800 ppm, from about 0.1 ppm to about 700 ppm, from about 0.2 ppm to about 600 ppm, from about 0.3 ppm to about 500 ppm, or from about 0.5 ppm to about 400 ppm compound of formula III or salt or solvate thereof in relation to the compound of formula V.

The composition in certain embodiments comprises from about 0.05 ppm to about 350 ppm, from about 0.1 ppm to about 300 ppm, from about 0.2 ppm to about 275 ppm, from about 0.3 ppm to about 250 ppm, from about 0.4 ppm to about 225 ppm, or from about 0.5 ppm to about 200 ppm compound of formula III or salt or solvate thereof in relation to compound V.

The composition comprising the compound of formula V and additionally the compound of formula III may comprise the compound of formula III as (i) 8α isomer, (ii) 8β isomer or (iii) a combination of 8α and 8β isomer. In said embodiments, the compound of formula II (which is contained in the compound of formula V) may be 14-hydroxycodeinone, and the compound of formula III may be 8-hydroxyoxycodone. In said embodiments, the compound of formula V may be 14-hydroxycodeinone sulfate and the compound of formula III may be 8-hydroxyoxycodone.

The composition comprising the compound of formula V or solvate thereof may be used as an intermediate or starting material for preparing another opioid or salt or solvate thereof, and for preparing an API which is an opioid or a pharmaceutically acceptable salt or solvate thereof, and/or a pharmaceutical composition or dosage form containing such API.

Pharmaceutical compositions and dosage forms produced from said composition comprising the compound of formula V or solvate thereof, preferably, contain less compound of formula III and/or formula II than pharmaceutical compositions prepared via a different intermediate.

Compounds and compositions which may be prepared from the composition comprising the compound of formula V or a solvate thereof will be described in the subsequent sections.

V. Processes for Preparation of Compounds of Formula IV or (Pharmaceutically Acceptable) Salts or Solvates Thereof Present invention further provides a process for preparing a compound of formula IV or an (optionally pharmaceutically acceptable) salt or solvate thereof from a compound having formula V or a solvate thereof as represented in the following Scheme 17:

Scheme 17

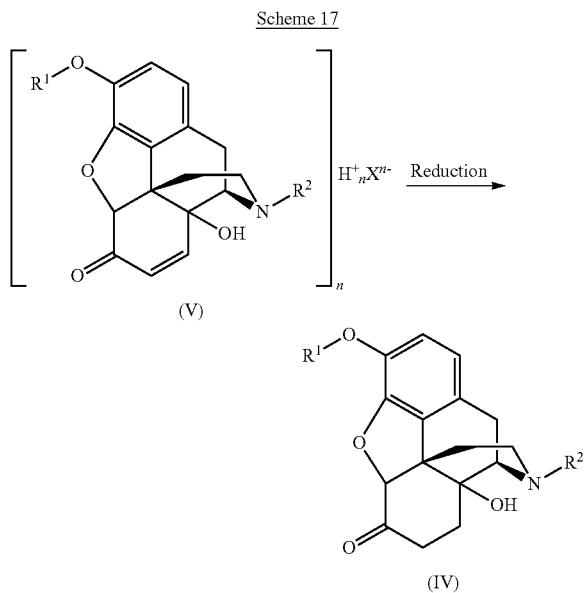

the process comprising the steps of (e) providing a solution or suspension comprising the compound of formula V or a solvate thereof as defined above; and (f) reducing the compound of formula V to the compound of formula IV or a salt or solvate thereof, wherein $R^1$, $R^2$, $X^{n-}$ and n are defined as above.

In certain embodiments, the solution or suspension comprising the compound of formula V or the solvate thereof is provided in step (e) by performing steps (a) to (b) of the process described in section II, steps (a) to (c) of the process described in section II, or steps (a) to (d) of the process described in section II. When steps (a) to (d) are performed, the compound of formula V or solvate thereof isolated in step (d) is dissolved or suspended to provide the solution or suspension of said compound in step (e).

In certain embodiments, the solution or suspension comprising the compound of formula V or the solvate thereof is the composition described in Section IV-A.

In certain embodiments, the reduction reaction in step (f) is performed by hydrogenation. Said hydrogenation may be hydrogenation with $H_2$ or transfer hydrogenation. Typically, the hydrogenation is performed in the presence of a hydrogenation catalyst.

An exemplary hydrogenation reaction is depicted in Scheme 18:

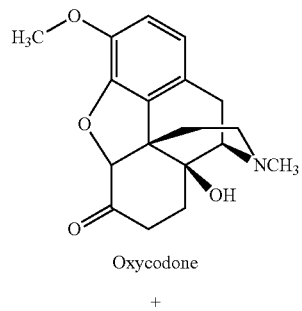

Oxycodone

+

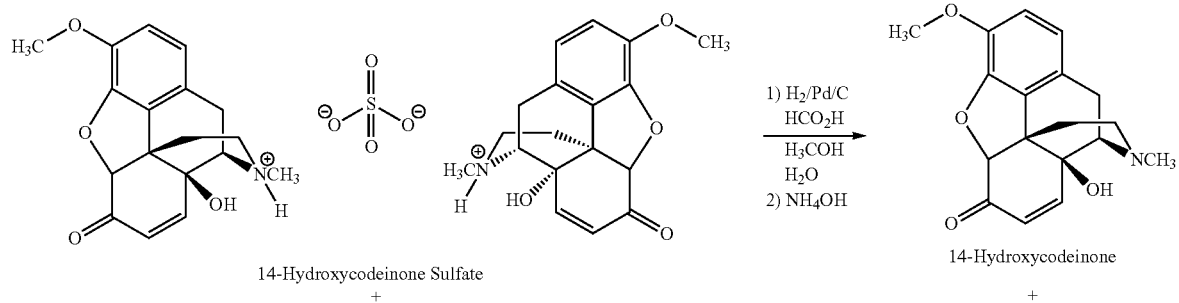

14-Hydroxycodeinone Sulfate          14-Hydroxycodeinone

+                                     +

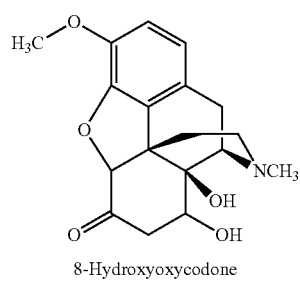
8-Hydroxyoxycodone

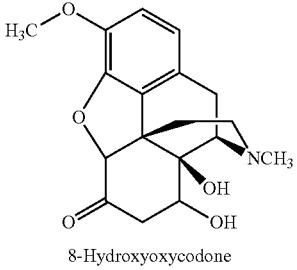
8-Hydroxyoxycodone

Scheme 18 takes into account that 8-hydroxyoxycodone (or, in general, an 8-hydroxy compound of formula III) or a salt thereof may be present in the starting material in addition to 14-hydroxycodeinone sulfate (or any other compound of formula V). Said 8-hydroxy compound may carry over during the reduction reaction. Or, as discussed above with respect to the prior art, if the reduction is performed under acidic conditions, said 8-hydroxy compound may be converted partially or completely to the corresponding 14-hydroxy compound of formula II (in Scheme 18: 14-hydroxycodeinone) during the reduction reaction. Thus, compound of formula II (in Scheme 18: 14-hydroxycodeinone) and compound of formula III (in Scheme 18: 8-hydroxyoxycodone) may be present in the reaction product which contains compound of formula IV (in Scheme 18: oxycodone) as main reduction product.

A further exemplary hydrogenation reaction is depicted in Scheme 18A:

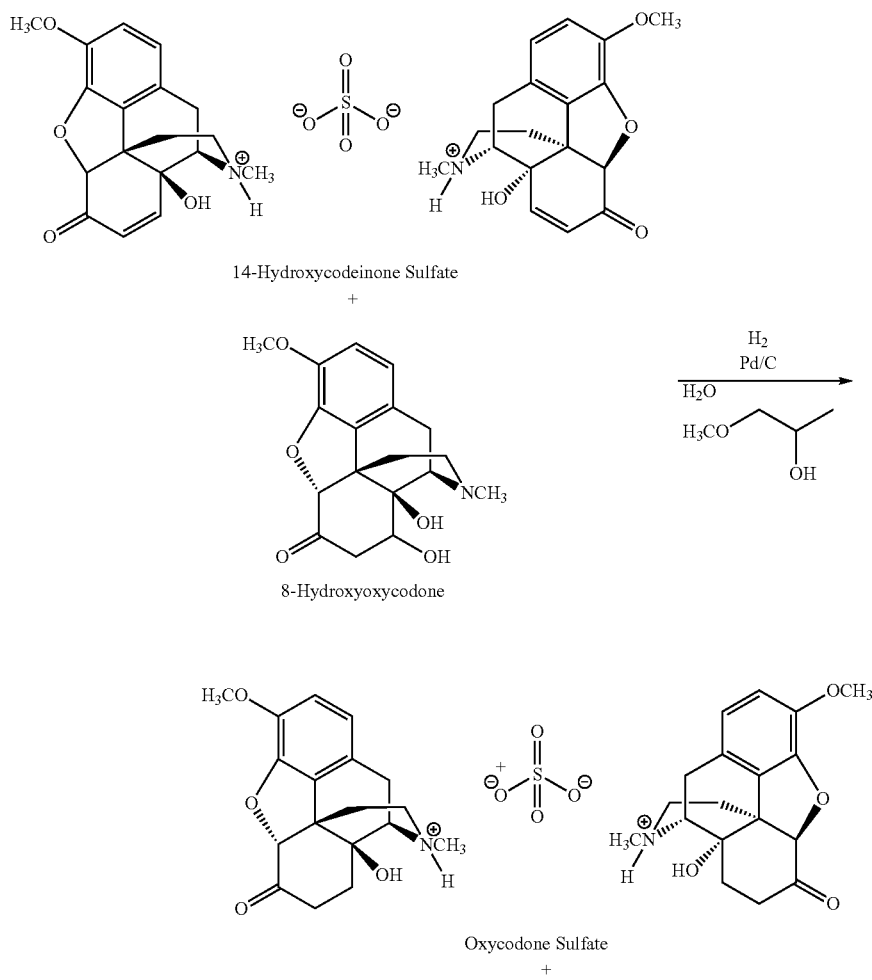

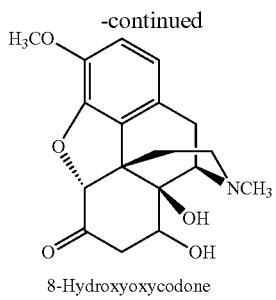
8-Hydroxyoxycodone

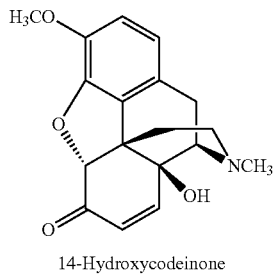
14-Hydroxycodeinone

Scheme 18A, like Scheme 18, takes into account the presence of 8-hydroxyoxycodone and the consequences of said presence. Deviating from Scheme 18, the reaction in Scheme 18A does not require step (2), i.e. the addition of a base like $NH_4OH$ after the reduction reaction. Thus, the products of the reduction reaction may be present in their protonated form or as a salt or solvate thereof. In one embodiment of the present invention, the compound of formula IV (represented by oxycodone in Scheme 18A) is present as a salt or solvate thereof, wherein the salt has the same anion $X^{n-}$ as the anion $X^{n-}$ of the starting material compound V. Said anion $X^{n-}$ is represented by sulfate in Scheme 18A. In a preferred aspect, the compound of formula IV is present as its sulfate salt or solvate thereof, and it is preferably precipitated during or after the reduction reaction and then isolated in its solid form. In another preferred aspect, the compound of formula IV is present as its trifluoroacetate salt or solvate thereof, and it is preferably precipitated during or after the reduction reaction and then isolated in its solid form.

Thus, in one embodiment, the compound of formula IV is present as its salt with anion $X^{n-}$ (e.g., as its sulfate salt) in the reaction mixture during and after the reduction reaction, and this salt or a solvate thereof may be optionally isolated from the reaction mixture, e.g. by precipitation and subsequent isolation of the precipitate. In said embodiment, the process may be represented by the following reaction scheme:

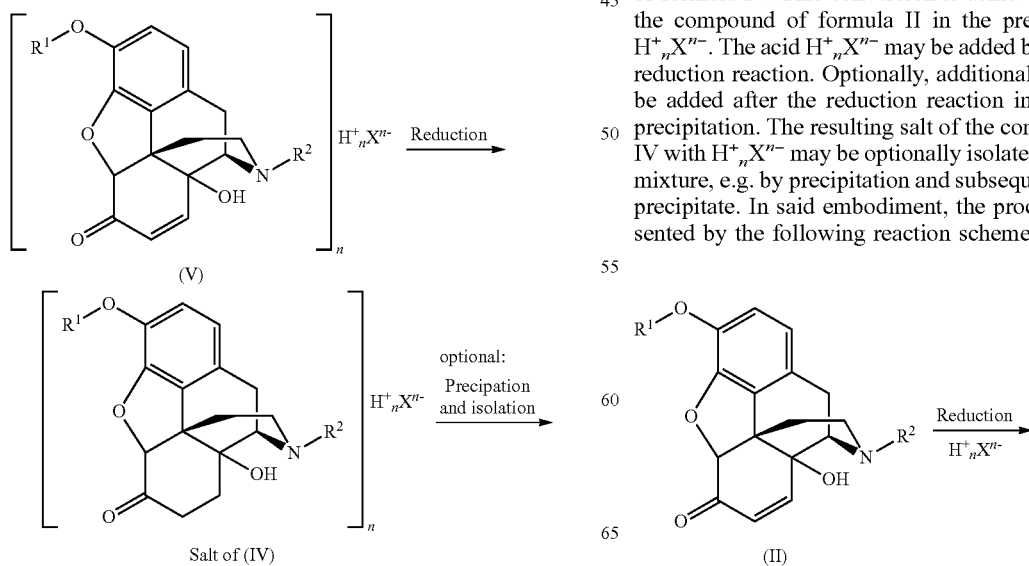

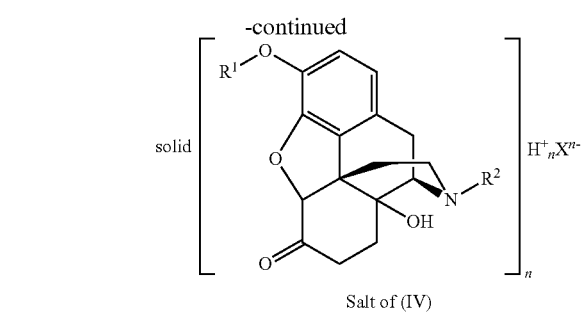

the process comprising the steps of (e) providing a solution or suspension of the compound having formula V or a solvate thereof; and (f) reducing the compound of formula V to the salt of the compound of formula IV with $H^+_n X^{n-}$; and optionally (g) isolating the salt of the compound of formula IV with $H^+_n X^{n-}$, wherein $R^1$, $R^2$, $X^{n-}$ and n are defined as above, and $X^{n-}$ is preferably $SO_4^{2-}$.

The present invention also provides a process wherein a compound of formula II is converted to a salt of the compound of formula IV with $H^+_n X^{n-}$, e.g. to a sulfate salt of formula IV. This conversion is achieved by reduction of the compound of formula II in the presence of the acid $H^+_n X^{n-}$. The acid $H^+_n X^{n-}$ may be added before or during the reduction reaction. Optionally, additional acid $H^+_n X^{n-}$ may be added after the reduction reaction in order to enhance precipitation. The resulting salt of the compound of formula IV with $H^+_n X^{n-}$ may be optionally isolated from the reaction mixture, e.g. by precipitation and subsequent isolation of the precipitate. In said embodiment, the process may be represented by the following reaction scheme:

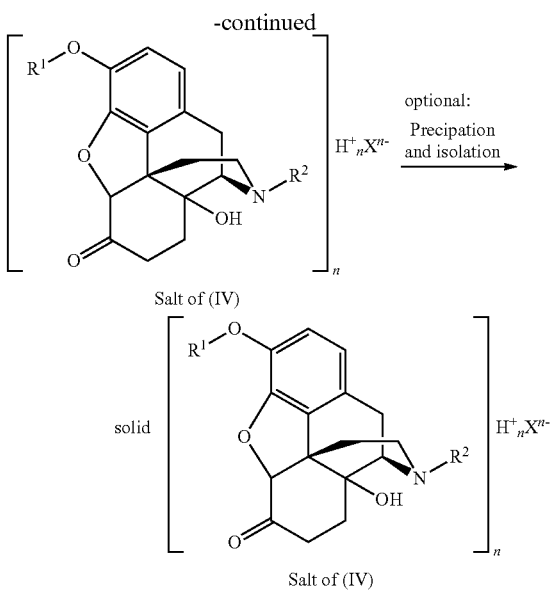

Salt of (IV)

Salt of (IV)

the process comprising the steps of
(e) providing a solution or suspension of the compound having formula II or a solvate thereof; and
(f) reducing the compound of formula II in the presence of an acid $H^+{}_nX^{n-}$ to the salt of the compound of formula IV with $H^+{}_nX^{n-}$; and optionally
(g) isolating the salt of the compound of formula IV with $H^+{}_nX^{n-}$,
wherein $R^1$, $R^2$, $X^{n-}$ and n are defined as above, and $X^{n-}$ is preferably $SO_4^{2-}$. This reduction is performed using the free base II. Said base may be provided by isolating it as intermediate from a compound of formula V. Moreover, the salt of the compound of formula IV prepared by said process is preferably oxycodone sulfate or a solvate thereof. I.e., in a preferred aspect of this process, 14-hydroxycodeinone base is converted to oxycodone sulfate (or a solvate thereof). A process for preparing a salt of IV wherein $X^{n-}$ is trifluoroacetate is also specifically considered in the context of the present invention.

In the context of the present invention, it is also considered to precipitate and isolate the compound of formula IV as its salt with $H^+{}_nX^{n-}$ from a solution containing the compound of formula IV as starting material.

The precipitation and isolation of the salt of the compound of formula IV with $H^+{}_nX^{n-}$ can result in a further purification effect, as the precipitated salt may contain less compound of formula III and/or of formula II than the mother liquor.

If the hydrogenation is performed under acidic conditions, the by-products present in the starting material and in the product may be present in their protonated form, or as a salt or solvate thereof.

The hydrogenation is generally performed at a temperature of from about 35° C. to about 85° C., from about 40° C. to about 60° C., or from about 40° C. to about 50° C.

In certain embodiments, the hydrogenation is performed with hydrogen gas.

The hydrogenation using hydrogen gas is performed at a suitable pressure. In certain embodiments, the hydrogenation is performed at a pressure of from about 17 psia (117.21 kPa) to about 100 psia (689.48 kPa). In certain embodiments, it is performed at a pressure of from about 35 psia (241.32 kPa) to about 80 psia (551.58 kPa), e.g., at about 60 psia (413.69 kPa).

The hydrogenation reaction may be run from about 0.5 minute to about 48 hours, from about 1 minute to about 24 hours, from about 3 minutes to about 22 hours, from about 5 minutes to about 18 hours, from about 7 minutes to about 16 hours, from about 10 minutes to about 12 hours, from about 12 minutes to about 12 hours, from about 20 minutes to about 12 hours, from about 30 minutes to about 4 hours, from about 2 hours to about 6 hours, or from about 3 hours to about 6 hours. In certain embodiments, the hydrogenation reaction is run from about 1 hour to about 48 hours.

In certain embodiments, the hydrogenation reaction is run for about 10 minutes, about 15 minutes, about 20 minutes, about 25 minutes, about 30 minutes, about 1 hour, about 1.5 hours, about 2 hours, about 2.5 hours, about 3 hours, about 3.5 hours, about 4 hours, about 4.5 hours, about 5 hours, about 5.5 hours, or about 6 hours.

In certain embodiments, the hydrogenation reaction is run for about 8 hours, about 12 hours, about 16 hours, about 20 hours, or about 24 hours.

In certain embodiments, the compound of formula IV or its salt or solvate resulting from the hydrogenation will be precipitated and optionally isolated from the reaction. Said precipitation may take place within about 30 minutes, about 1 hour, about 1.5 hours, about 2 hours, about 2.5 hours, about 3 hours, about 3.5 hours, about 4 hours, about 4.5 hours, about 5 hours, about 5.5 hours, or about 6 hours after the start of the reaction. It may also take place within a longer period of time, including within the complete reaction time. It may also alternatively or additionally take place during the period immediately following the reaction period, e.g. during the venting period after a hydrogenation reaction using hydrogen gas.

An exemplary non-limiting list of hydrogenation catalysts includes, e.g., Pd/C, palladium-charcoal, a combination of diphenylsilane and Pd/C, Pd(Ph$_3$P)/ZnCl$_2$, a combination of Pd/C with sodium hypophosphite (e.g., in aqueous acetic acid), Pt/C, Ru/C, Rh/C, PdO$_2$, PtO$_2$, zinc, magnesium. In certain embodiments, the catalyst is a palladium catalyst (e.g., Pd/C). In certain embodiments, the hydrogenation catalyst is not a metal, e.g., when the hydrogenation is a metal-free transfer hydrogenation as described in Yang, J. W. et al., Angew. Chem. Int. Ed. (2004) 43:6660-6662.

In certain embodiments, a solid support catalyst is used, e.g., to ensure reaction completion upon contact and/or potentially prevent or minimize the formation of any new compound of formula II from a compound of formula III (e.g., formation of 14-hydroxycodeinone from 8-hydroxyoxycodone).

Transfer hydrogenation involves the use of a hydrogen transfer reagent.

Suitable hydrogen transfer reagents include HCO$_2$H, HCO$_2$H/HCO$_2$Na, HCO$_2$H/NEt$_3$, HCHO, H$_2$SO$_4$, HCO$_2$Na/NEt$_3$, H$_2$SO$_4$/NEt$_3$, H$_3$CSO$_2$NHNH$_2$/NEt$_3$, a combination thereof, and the like. Other hydrogen donors, like isopropanol, indoline, cyclohexene, sodium borohydride, tetrahydroquinoline, 2,5-dihydrofuran, phosphoric acid, sodium dithionite, and combinations thereof, might also be useful. In certain embodiments, the hydrogen transfer reagent is a dihydropyridine, e.g., as described in Yang, J. W. et al., Angew. Chem. Int. Ed. (2004) 43:6660-6662.

The hydrogenation may be done by a batch method or in a continuously flowing stream.

In certain embodiments, the hydrogenation is done by a batch method. In an exemplary batch method, a catalyst (e.g., palladium on carbon) is charged into a batch reactor. A solution or suspension of the compound of formula V or the solvate thereof is added. If necessary, deionized water and acid are also added to the batch reactor. The batch reactor is then sealed and hydrogenated (e.g., at 60 psia (413.69 kPa), and 40° C. or 55° C.) for a time period sufficient to complete hydrogenation (e.g., for 24 hours). The catalyst is then removed by filtration.

The resulting compound of formula IV or salt or solvate thereof may then be precipitated by, e.g., addition of ammonium hydroxide. Alternatively, a precipitation can be achieved by adding an antisolvent to the filtrate, or by preparing a supersaturated solution from which the resulting compound of formula IV or salt or solvate thereof is precipitated, e.g. by cooling. The precipitated solids are then optionally washed and dried.

In certain embodiments, the hydrogenation reaction is conducted in a continuously flowing stream. A reaction in a continuously flowing stream of the reactants allows for the transport of matter into and out of the reaction mixture as the reaction is taking place. Running the reaction in a continuously flowing stream allows, e.g., better control over reaction conditions (including, e.g., time, temperature, equivalents of reagents, pressure, temperature, time of exposure of reactants to catalysts, pH, etc.), and isolation and/or removal of the product having formula IV from the reaction mixture as it is being formed and/or before any undesired compound is formed. In certain embodiments, the compound of formula IV is removed from the reaction mixture as it is being formed.

In certain embodiments, conducting the reaction in a continuously flowing stream allows for conducting the reaction at a temperature which exceeds the boiling point of the solvent, because the pressure can be safely maintained.

In certain embodiments, conducting the reduction in a continuously flowing stream increases the yield of the reaction, increases the volume efficiency of the reaction and/or decreases the number and amounts of by-products formed during the reduction reaction, as the compound of formula IV is removed before it reacts with and/or is degraded by the remaining reactants.

In certain embodiments, the compound of formula V or solvate thereof is dissolved in a suitable solvent before and/or during the hydrogenation reaction. A suitable solvent may include or consist of, e.g., methanol, tetrahydrofuran, isopropanol, acetone, ethanol, 1-methoxy-2-propanol, 2-ethoxyethanol, tert-amyl alcohol, isobutanol, 2-methyltetrahydrofuran, n-propanol, 1-butanol, 2-butanol, tert-butanol, isopropyl acetate, and di(ethylene glycol) or a mixture of water with any one of the foregoing. In certain embodiments, the suitable solvent includes or consists of methanol, tetrahydrofuran, isopropanol, acetone, ethanol, 1-methoxy-2-propanol, 2-ethoxyethanol, tert-amyl alcohol, or a mixture of water with any one of the foregoing.

In certain embodiments wherein preferably the compound of formula III is an 8-hydroxyoxycodone and the compound of formula IV is oxycodone, the suitable solvent is a 50:50 methanol:water mixture, 60:40 methanol:water mixture, 70:30 methanol:water mixture, 80:20 methanol:water mixture, 90:10 methanol:water mixture, 100:0 methanol:water mixture, 50:50 ethanol:water mixture, 60:40 ethanol:water mixture, 70:30 ethanol:water mixture, 80:20 ethanol:water mixture, 90:10 ethanol:water mixture, 100:0 ethanol:water mixture, 90:10 tetrahydrofuran:water mixture, 100:0 tetrahydrofuran:water mixture, 90:10 isopropanol:water mixture, 70:30 acetone:water mixture, 80:20 acetone:water, or 90:10 acetone:water mixture. 8-Hydroxyoxycodone is more soluble in these mixtures than oxycodone base and therefore may remain in solution while the oxycodone free base may be precipitated by addition of a base at the end of the hydrogenation.

In certain embodiments, the suitable solvent comprises or consists of a mixture of n-butanol and water.

In certain embodiments, the suitable solvent comprises or consists of a mixture of 1-methoxy-2-propanol and water.

In certain embodiments, the suitable solvent is a mixture of 1-methoxy-2-propanol and water, wherein the volume ratio of these two components is preferably from 40:60 to 90:10 1-methoxy-2-propanol:water, e.g. 50:50 or 80:20. Preferably, the mixture contains more 1-methoxy-2-propanol than water. In these mixtures, the salt of the compound of formula IV with $X^{n-}$ advantageously precipitates during or after the reduction reaction.

In certain embodiments, the solvent may contain an effective amount of acid to solubilize the compound of formula V or solvate thereof and to reduce conversion of the compound of formula V and/or compound of formula II to a compound of formula III during the reduction reaction. In certain embodiments, no acids are added to the reaction mixture.

In certain embodiments, the solvent used during the reduction reaction is different from the solvent used during the oxidation of a compound of formula I to the compound of formula V as described in Section II. In certain other embodiments, the same solvents are used for reduction and oxidation.

Once the hydrogenation is completed, the compound of formula IV, salt or solvate thereof may be precipitated. In certain embodiments, the precipitation of the compound of formula IV, salt or solvate thereof is initiated and/or enhanced by one or more of the following:
(i) adjusting (e.g., lowering) the temperature of the reaction mixture to the precipitation temperature;
(ii) addition of an antisolvent;
(iii) addition of a seed crystal;
(iv) changing the ionic strength of the reaction mixture (e.g., by addition of a salt);
(v) concentrating the reaction mixture;
(vi) reducing or stopping agitation of the reaction mixture; or any other conventional method for initiating or enhancing precipitation or crystallization.

When the temperature is adjusted to the precipitation temperature, this means that the precipitation of the compound of formula IV or the salt or solvate thereof is initiated and/or enhanced by adjusting the temperature of the reaction mixture to or beyond a temperature at which said compound precipitates ("precipitation temperature"). The temperature is either adjusted by performing the reaction at the precipitation temperature, or by lowering the temperature of the reaction mixture during the reaction or after completion of the reaction.

In certain embodiments, the reaction mixture is adjusted to a temperature of ≤40° C. to initiate precipitation, i.e. the precipitation temperature is ≤40° C. In certain embodiments, the precipitation is initiated at a precipitation temperature of about −20° C., about −15° C., about −10° C., about −5° C., about 0° C., about 5° C., about 10° C., about 15° C., about 17° C., about 19° C., about 21° C., about 23° C., about 25° C., about 27° C., about 29° C., about 31° C., about 33° C., about 35° C., about 37° C., or about 40° C.

In certain embodiments, the precipitation temperature is in a range of from about −20° C. to about 40° C., preferably from about −10° C. to about 40° C., more preferably from about −5° C. to about 35° C.

In certain embodiments, the precipitation temperature of the salt of the compound of formula IV or a solvate of said salt is in a range of from about −10° C. to about 30° C., preferably from about −5° C. to about 25° C., more preferably from about 0° C. to about 22° C., more preferably from about 5° C. to about 22° C.

In certain embodiments, an antisolvent is used in addition to adjusting the temperature to the precipitation temperature. In certain embodiments, e.g., when the compound of formula IV is oxymorphone sulfate or a solvate thereof, precipitation will also occur without adding an antisolvent.

In certain embodiments, precipitation is achieved by addition of a suitable organic or inorganic base until a suitable pH is reached. A suitable pH may be a pH of ≥3, ≥4, ≥5, ≥6, or ≥7. A suitable base may comprise or consist of NaOH, KOH, $Na_2CO_3$, $K_2CO_3$, $NaHCO_3$, $KHCO_3$, $HCO_2Na$, $CH_3CO_2Na$, $NEt_3$, $NH_4OH$ or any mixtures thereof.

In certain embodiments, the compound of formula IV is precipitated as its salt or a solvate thereof. In said salt, the anion is preferably the same $X^{n-}$ as in the starting material compound V. This precipitation may be achieved by adding an antisolvent to a solution of the compound of formula IV and its counter ion, or by preparing a supersaturated solution (e.g. by cooling or concentrating a reaction mixture) from which the resulting salt of the compound of formula IV or solvate thereof is precipitated, e.g. by cooling or by adding a seed crystal. The precipitated solids are then optionally washed and dried. In one aspect, this precipitation may be achieved by adding one or more of acetone, 1-methoxy-2-propanol, and tert-butyl methyl ether to a reaction mixture. E.g., acetone and/or 1-methoxy-2-propanol may be added to a reaction mixture which already may comprise water. In one aspect, this precipitation may be achieved by using a mixture of water and an antisolvent, in particular a mixture of water and 1-methoxy-2-propanol as described above. Said mixture may be present as reaction solvent during the reduction reaction, or it may replace the reaction solvent after completion of the reduction reaction. The mixture can also be prepared by adding antisolvent after completion of the reaction.

Further suitable antisolvents may be the antisolvents described in section II, and the antisolvents described in Examples 5 and 6. I.e., a suitable antisolvent may comprise or consist of tert-butyl methyl ether, diethyl ether, hexane(s), tert-amyl alcohol, methanol, ethanol, n-propanol, isopropanol, 1-butanol, 2-butanol, tert-butanol, isobutanol, heptanes, xylenes, toluene, acetone, 2-butanone, ethyl acetate, isopropyl acetate, tetrahydrofuran, 2-methyl-tetrahydrofuran, 1,2-dichloroethane, chloroform, dichloromethane, 1-methoxy-2-propanol, 2-ethoxyethanol, 1,4-dioxane, methyl formate, methyl acetate, or a mixture of two or more of any of the foregoing. The listed alcohols and ethers are the preferred antisolvents.

The resulting precipitate may then be isolated, thus removing it from the mother liquor and advantageously further purifying the salt from compound of formula III and/or II which remains in the mother liquor.

Preferably, the resulting compound of formula IV, salt or solvate thereof comprises lower amounts of a compound of formula III and/or formula II (or salt or solvate thereof) as compared to compound of formula IV made by a process which does not involve the use of a compound of formula V as a starting material or intermediate material.

Compounds of formula IV and compositions comprising said compounds of formula IV which can be prepared via the process of present invention are described, e.g., in Section VII below. The amounts of compounds of formula III and II which may be present in the compositions comprising the compounds of formula IV are described in Section VII below. In certain embodiments, these compounds of formula IV or compositions comprising the compounds of formula IV are the product of the process described in the present section or in the subsequent Section VI.

In certain embodiments, the compositions comprising the compounds of formula IV which are the product of the process described in the present section or in the subsequent Section VI can be used as pharmaceutical compositions without further processing or purification steps, in particular without further reduction (e.g., hydrogenation) steps.

In certain embodiments of this process starting from the compound of formula V or a solvate thereof, the compound of formula V is 14-hydroxycodeinone sulfate or a solvate thereof, and the compound of formula IV is oxycodone or a salt or solvate thereof.

In certain embodiments of this process starting from the compound of formula V or a solvate thereof, the compound of formula V is 14-hydroxycodeinone sulfate or a solvate thereof, and the compound of formula IV is oxycodone sulfate or a solvate thereof.

In certain embodiments of this process starting from the compound of formula V or a solvate thereof, the compound of formula V is 14-hydroxycodeinone trifluoroacetate or a solvate thereof, and the compound of formula IV is oxycodone trifluoroacetate or a solvate thereof.

VI. Processes for Preparing a Compound of Formula IV Starting from a Compound of Formula I Present invention further provides a process for preparing a compound of formula IV from a compound of formula I via a compound of formula V or a solvate thereof. In this process, the compound of formula V or solvate thereof serves as an intermediate. Said intermediate compound of formula V or the solvate thereof may either be isolated or converted to a compound of formula IV or a salt or solvate thereof without further isolation. In certain preferred embodiments, said intermediate compound of formula V or the solvate thereof is isolated before its conversion to the compound of formula IV or a salt or solvate thereof.

Thus, present invention provides a process for preparing a compound of formula IV or a salt or solvate thereof from a compound of formula I or a salt or solvate thereof, the process comprising (Scheme 19):

Scheme 19

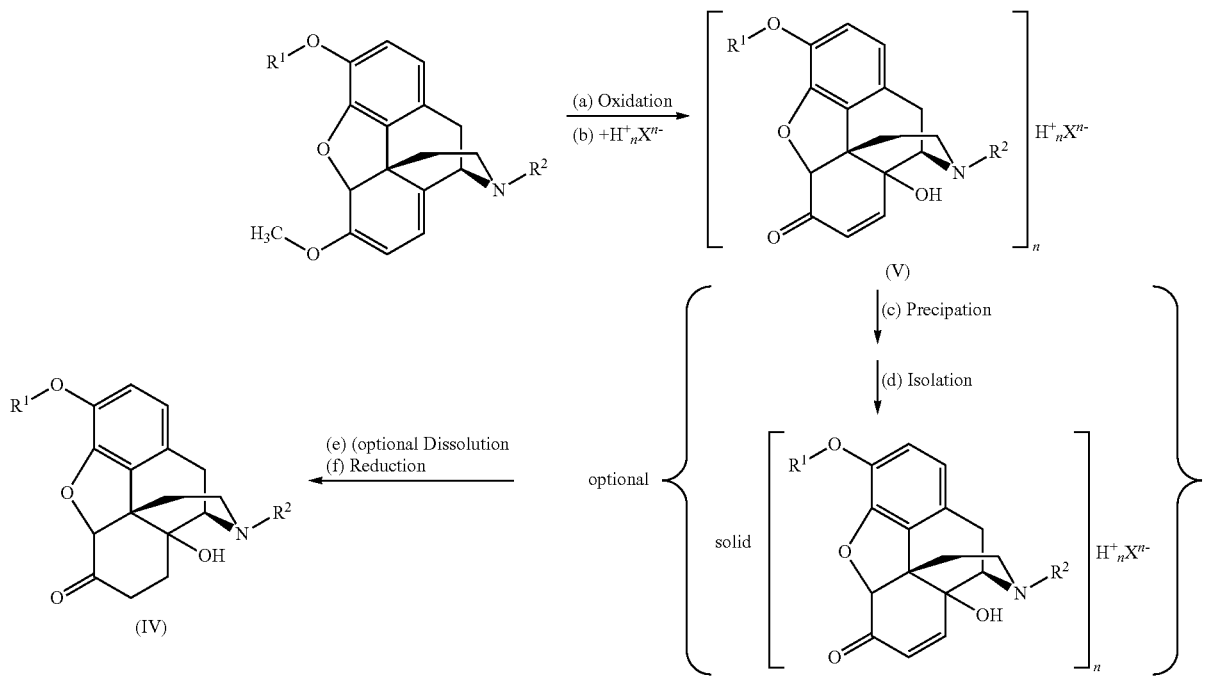

(a) oxidizing the compound of formula I;
(b) adding an acid $H^+_n X^{n-}$ to the reaction mixture before, during and/or after the oxidation reaction;
(c) optionally precipitating the compound of formula V or a solvate thereof;
(d) optionally isolating the precipitated compound of formula V or solvate thereof;
(e) optionally providing a solution or suspension of the compound of formula V or solvate thereof; and
(f) reducing the compound of formula V or solvate thereof to the compound of formula IV or a salt or solvate thereof, wherein $R^1$, $R^2$, $X^{n-}$ and n are defined as above.

In certain embodiments, the compound of formula V or solvate thereof is precipitated and/or isolated in steps (c) and/or (d) before the reduction via steps (e) and (f).

In certain embodiments, said process will contain a further step, namely (g) isolating the compound of formula IV as its salt with $H^+_n X^{n-}$ or as a solvate of said salt.

In certain embodiments, said process will contain a further step, namely the liberation of the compound of formula II as a base from the compound of formula V before the reduction step (f). In these embodiments, the compound of formula II in its free base form is subsequently reduced in step (f) instead of the compound of formula V.

In certain embodiments, step (f) of the process results in a pharmaceutically acceptable salt or solvate of the compound of formula IV. In certain embodiments, step (f) of the process results not only in such pharmaceutically acceptable salt or solvate of the compound of formula IV, but the complete resulting composition can be used as pharmaceutical composition without requiring further processing (e.g., purification). In particular, it may be used without an additional hydrogenation to remove by-products, e.g., compounds of formula II. For example, the process may result in an oxycodone salt composition which is suitable for incorporation into a dosage form, the oxycodone salt composition being directly prepared from the reduction product of step (f) by a conversion which does not include a further/additional hydrogenation step.

In certain embodiments, the salt or solvate of compound of formula IV which results from step (f) is not a pharmaceutically acceptable salt or solvate.

In certain embodiments, the compound of formula IV or salt or solvate thereof resulting from step (f) may be converted into a pharmaceutically acceptable salt or solvate thereof in an additional step at the end of the process. Methods for such conversion are known in the art (e.g., anion exchange).

In certain embodiments, the compound of formula V or solvate thereof which is an intermediate of the process will have the properties as described in Section IV.

All elements of said process and the embodiments of said elements have already been described above. Compounds of formula IV which can be prepared via the process, and the amounts of compounds of formula III and formula II which may be present in compositions comprising said compounds of formula IV are described in Section VII below. In certain embodiments, these compounds are the product of the process described in the present section.

In the following, an exemplary embodiment of said process will be described. Therein the compound of formula (I) is thebaine or a salt or solvate thereof, the oxidation agent comprises or is performic acid formed in situ from hydrogen peroxide and formic acid, the acid $H^+_n X^{n-}$ in step (b) is sulfuric acid which is added to the reaction mixture, the compound having formula V is 14-hydroxycodeinone sulfate or a solvate thereof, and the compound of formula IV is oxycodone or a salt or solvate thereof.

In another exemplary embodiment, the compound of formula (I) is thebaine or a salt or solvate thereof, the oxidation agent comprises or is performic acid formed in situ from hydrogen peroxide and formic acid, the acid H+nX n− in step (b) is sulfuric acid which is added to the reaction mixture, the compound having formula V is 14-hydroxycodeinone sulfate or a solvate thereof, and the compound of formula IV is oxycodone sulfate or a solvate thereof.

VII. Compounds of Formula IV

Present invention further provides a compound of formula IV:

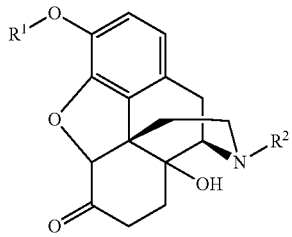

(IV)

wherein R¹ and R² are defined as above,
or a salt or solvate thereof.

In certain embodiments, the compound of formula IV has one of the following stereoconfigurations:

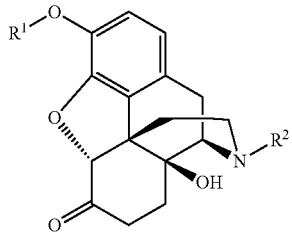

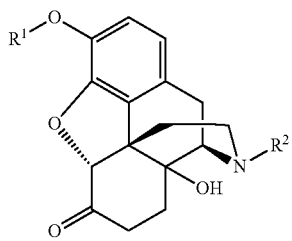

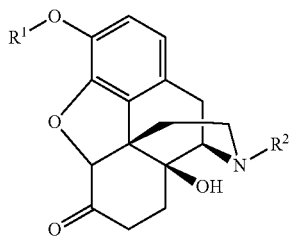

In preferred embodiments, the compound of formula IV has the stereoconfiguration represented below:

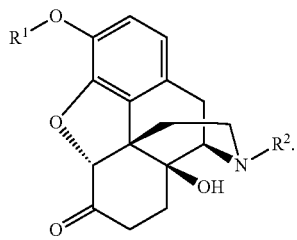

The compound of formula IV or salt or solvate thereof of present invention is obtainable or has been obtained by the processes described in the preceding sections.

The salt or solvate of the compound of formula IV may be a pharmaceutically acceptable salt or solvate. Such salts or solvates are known in the art.

In preferred embodiments, the compound of formula IV is selected from the group consisting of oxycodone, noroxycodone, salts thereof and solvates thereof. In more preferred embodiments, it is selected from the group consisting of oxycodone, salts thereof and solvates thereof. In even more preferred embodiments, it is an oxycodone salt. In even more preferred embodiments, it is oxycodone hydrochloride.

In certain preferred embodiments, the compound of formula IV is provided as its salt with $X'''^{-}$ as anion. In more preferred embodiments, it is provided as its sulfate salt or trifluoroacetate salt. In even more preferred embodiments, it is provided as its sulfate salt. In a specific aspect, it is oxycodone trifluoroacetate or a solvate thereof.

As already indicated above, the product of the process encompassing steps (e) and (f) is preferably oxycodone sulfate. However, in one aspect of the present invention, oxycodone sulfate as a compound itself is not encompassed by the present invention, as said compound has been known before in the art.

VII-A. Compositions Comprising Compound of Formula IV

The present invention further provides a composition comprising a compound of formula IV or an (optionally pharmaceutically acceptable) salt or solvate thereof.

Said composition may be the product of the process described in Section VI.

Said composition may be a solid or a liquid. In certain embodiments, it is a solid. In certain embodiments, it is the precipitate containing the compound of formula IV as described in Section VI.

In certain embodiments, the composition comprising the compound of formula IV or the (optionally pharmaceutically acceptable) salt or solvate thereof additionally comprises a compound having the formula III:

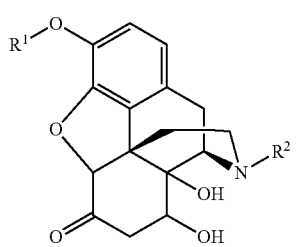

(III)

wherein R¹ and R² are defined as in the compound of formula IV,
or a salt or solvate thereof.

In certain embodiments, the amount of the compound of formula III or salt or solvate thereof in the composition is less than about 2500 ppm, less than about 2250 ppm, less than about 2000 ppm, less than about 1750 ppm, less than about 1500 ppm, or less than about 1250 ppm of the compound of formula IV or salt or solvate thereof (HPLC peak area ratio).

In certain embodiments, the amount of the compound of formula III or salt or solvate thereof in the composition is less than about 1000 ppm, less than about 750 ppm, less than about 500 ppm, or less than about 400 ppm of the compound of formula IV or salt or solvate thereof (HPLC peak area ratio).

In certain embodiments, the amount of the compound of formula III or salt or solvate thereof in the composition is less than about 300 ppm, less than about 275 ppm, less than about 250 ppm, less than about 225 ppm, less than about 200 ppm, less than about 175 ppm, less than about 150 ppm, or less than about 125 ppm of the compound of formula IV or salt or solvate thereof (HPLC peak area ratio).

In certain embodiments, the amount of the compound of formula III or salt or solvate thereof in the composition is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm of the compound of formula IV or salt or solvate thereof (HPLC peak area ratio).

In certain embodiments, the amount of the compound of formula III or salt or solvate thereof in the composition is less than about 10 ppm, less than about 8 ppm, less than about 6 ppm, less than about 4 ppm, or less than about 2 ppm of the compound of formula IV or salt or solvate thereof (HPLC peak area ratio).

In certain embodiments, the amount of the compound of formula III or salt or solvate thereof in the composition is less than about 1 ppm, less than about 0.8 ppm, less than about 0.6 ppm, less than about 0.4 ppm, less than about 0.3 ppm, less than about 0.2 ppm, or less than about 0.1 ppm of the compound of formula IV or salt or solvate thereof (e.g., the amount of 8-hydroxyoxycodone is from about 0.1 ppm to about 0.7 ppm of the 14-hydroxycodeinone sulfate) (HPLC peak area ratio).

In certain embodiments, the amount of the compound of formula III or salt or solvate thereof in the composition has a lower limit of about 0.05 ppm of the compound of formula IV or salt or solvate thereof (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm. For example, the amount of the compound of formula III or salt or solvate thereof in the composition may range from about 0.05 ppm to 1 ppm in a certain embodiment, and from about 1 ppm to about 10 ppm in a certain other embodiment.

In certain embodiments, the compound of formula IV is oxycodone or a salt or solvate thereof, and the amount of 8-hydroxyoxycodone or salt or solvate thereof in the composition is less than about 2500 ppm, less than about 2250 ppm, less than about 2000 ppm, less than about 1750 ppm, less than about 1500 ppm, less than about 1250 ppm, less than about 1000 ppm, less than about 750 ppm, less than about 500 ppm, less than about 400 ppm, less than about 300 ppm, or less than about 200 ppm of the oxycodone (HPLC peak area ratio).

In certain embodiments, the composition comprises from about 0.05 ppm to about 2500 ppm, from about 0.05 to about 2250 ppm, from about 0.1 ppm to about 2000 ppm, from about 0.3 to about 1750 ppm, from about 0.5 ppm to about 1500 ppm, or from about 1 ppm to about 1250 ppm compound of formula III or a salt or solvate thereof in relation to the compound of formula IV or salt or solvate thereof (HPLC peak area ratio).

In certain embodiments, the composition comprises from about 0.05 ppm to about 1000 ppm, from about 0.1 ppm to about 800 ppm, from about 0.1 ppm to about 700 ppm, from about 0.2 ppm to about 600 ppm, from about 0.3 ppm to about 500 ppm, or from about 0.5 ppm to about 400 ppm compound of formula II or salt or solvate thereof in relation to the compound of formula IV or salt or solvate thereof.

In certain embodiments, the composition comprises from about 0.05 ppm to about 350 ppm, from about 0.1 ppm to about 300 ppm, from about 0.2 ppm to about 275 ppm, from about 0.3 ppm to about 250 ppm, from about 0.4 ppm to about 225 ppm, or from about 0.5 ppm to about 200 ppm compound of formula III or salt or solvate thereof in relation to compound IV or salt or solvate thereof.

In certain embodiments, the composition comprising the compound of formula IV or the (optionally pharmaceutically acceptable) salt or solvate thereof additionally comprises a compound having the formula II

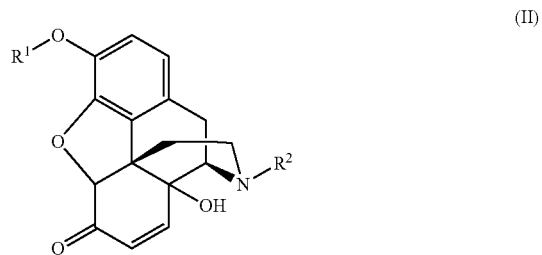

(II)

wherein $R^1$ and $R^2$ are defined as in the compound of formula IV,
or a salt or solvate thereof.

The amount of the compound having the formula II or salt or solvate thereof in relation to the amount of the compound having the formula IV or salt or solvate thereof in the composition may in certain embodiments be less than about 500 ppm, less than about 250 ppm, less than about 200 ppm, less than about 100 ppm, less than about 50 ppm or less than about 40 ppm (HPLC peak area ratio). In certain embodiments, it may be less than about 30 ppm, less than about 25 ppm, less than about 20 ppm, less than about 15 ppm, less than about 10 ppm, less than about 5 ppm, or less than about 2.5 ppm (HPLC peak area ratio). In certain embodiments, it may be less than about 1 ppm, less than about 0.8 ppm, less than about 0.6 ppm, less than about 0.6 ppm, less than about 0.4 ppm, less than about 0.2 ppm, or less than about 0.1 ppm (HPLC peak area ratio).

In certain embodiments, the amount of the compound of formula II or salt or solvate thereof in the composition has a lower limit of about 0.05 ppm of the compound of formula IV or salt or solvate thereof (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm. For example, the amount of the compound of formula II or salt or solvate thereof in the composition may range from about 0.05 ppm to 1 ppm in a certain embodiment, and from about 1 ppm to about 10 ppm in a certain other embodiment.

The composition in certain embodiments comprises from about 0.05 ppm to about 500 ppm, from about 0.05 ppm to about 250 ppm, from about 0.05 ppm to about 200 ppm, from about 0.05 ppm to about 100 ppm, from about 0.05 ppm to about 50 ppm, from about 0.05 ppm to about 25 ppm, from about 0.05 ppm to about 10 ppm, from about 0.05 ppm to about 5 ppm, or from about 0.05 ppm to about 1 ppm compound of formula II or salt or solvate thereof in relation to compound IV or salt or solvate thereof.

In certain embodiments wherein the compound of formula IV is oxycodone or a salt or solvate thereof and wherein the compound of formula II is 14-hydroxycodeinone or a salt or solvate thereof, the amount of the compound having the formula II in relation to the amount of the compound having the formula IV in the composition is less than about 100 ppm, less than about 50 ppm, less than about 40 ppm, less than about 30 ppm, less than about 25 ppm, less than about 20 ppm, less than about 15 ppm, less than about 10 ppm, less than about 5 ppm, less than about 2.5 ppm, less than about 1 ppm, less than about 0.8 ppm, less than about 0.6 ppm, less than about 0.6 ppm, less than about 0.4 ppm, less than about 0.2 ppm, or less than about 0.1 ppm of the compound of formula IV (HPLC peak area ratio).

The composition comprising the compound of formula IV or salt or solvate thereof may also additionally comprise a combination of a compound of formula III with a compound of formula II, preferably within the limits for the single compounds II and III as described in the preceding paragraphs.

In one embodiment, said compound of formula IV is oxycodone or a salt or solvate thereof, said compound having the formula III is 8-hydroxyoxycodone or a salt or solvate thereof, and said compound having the formula II is 14-hydroxycodeinone or a salt or solvate thereof. The compound of formula IV may be an oxycodone salt. In one embodiment, it may be oxycodone hydrochloride.

In another embodiment, said compound of formula IV is noroxycodone or a salt or solvate thereof, said compound having the formula III is 8-hydroxynoroxycodone or a salt or solvate thereof, and said compound having the formula II is 14-hydroxynoroxycodeinone or a salt or solvate thereof.

In certain embodiments, the composition comprising the compound of formula IV or the (optionally pharmaceutically acceptable) salt or solvate thereof additionally comprises both a compound of formula II and a compound of formula III. In certain embodiments, the composition comprises a combined amount of compound of formula II and compound of formula III which is less than about 3000 ppm, less than about 2750 ppm, less than about 2500 ppm, less than about 2250 ppm, less than about 2000 ppm, less than about 1750 ppm, less than about 1500 ppm, or less than about 1250 in relation to the amount of the compound of formula IV (HPLC peak area ratio).

In certain embodiments, the combined amount of the compound of formula II and III in the composition is less than about 1000 ppm, less than about 750 ppm, less than about 500 ppm, less than about 400 ppm, less than about 300 ppm, or less than about 275 ppm in relation to the amount of the compound of formula IV (HPLC peak area ratio).

In certain embodiments, the combined amount of the compound of formula II and III in the composition is less than about 250 ppm, less than about 225 ppm, less than about 200 ppm, less than about 175 ppm, less than about 150 ppm, or less than about 125 ppm in relation to the amount of the compound of formula IV (HPLC peak area ratio).

In certain embodiments, the combined amount of the compound of formula II and III in the composition is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm in relation to the amount of the compound of formula IV (HPLC peak area ratio).

In certain embodiments, the combined amount of the compound of formula II and III in the composition is less than about 10 ppm, less than about 8 ppm, less than about 6 ppm, less than about 4 ppm, or less than about 2 ppm in relation to the amount of the compound of formula IV (HPLC peak area ratio).

In certain embodiments, the combined amount of the compound of formula II and III in the composition is less than about 1 ppm, less than about 0.8 ppm, less than about 0.6 ppm, less than about 0.4 ppm, less than about 0.3 ppm, less than about 0.2 ppm, or less than about 0.1 ppm in relation to the amount of the compound of formula IV (HPLC peak area ratio).

In certain embodiments, the combined amount of the compound of formula II and III in the composition has a lower limit of about 0.05 ppm of the compound of formula IV (HPLC peak area ratio). In certain embodiments, the lower limit is about 0.1 ppm, about 0.3 ppm, about 0.5 ppm, about 0.7 ppm, about 1 ppm, about 1.5 ppm, about 2 ppm, or about 3 ppm in relation to the amount of the compound of formula IV (HPLC peak area ratio).

In certain embodiments, the composition comprises less than about 200 ppm, less than about 150 ppm, less than about 100 ppm, or less than about 50 ppm of a compound of formula II or a salt or solvate thereof, and/or less than about 1000 ppm, less than about 750 ppm, less than about 500 ppm, less than about 300 ppm, less than about 200 ppm, or less than about 100 ppm of a compound of formula III or a salt or solvate thereof.

In certain embodiments, the composition comprises less than about 100 ppm, less than about 50 ppm, less than about 25 ppm, less than about 20 ppm, less than about 15 ppm, or less than about 10 ppm of a compound of formula II or a salt or solvate thereof, and/or less than about 300 ppm, less than about 200 ppm, less than about 100 ppm, less than about 50 ppm, less than about 25 ppm, or less than about 10 ppm of a compound of formula III or a salt or solvate thereof.

In certain embodiments, the composition comprises less than about 25 ppm, less than about 20 ppm, less than about 15 ppm, less than about 10 ppm, less than about 5 ppm, or less than about 1 ppm of a compound of formula II or a salt or solvate thereof, and/or less than about 100 ppm, less than about 50 ppm, less than about 25 ppm, less than about 10 ppm, or less than about 5 ppm of a compound of formula III or a salt or solvate thereof.

In certain embodiments, the composition comprises less than about 10 ppm, less than about 5 ppm, less than about 4 ppm, less than about 3 ppm, less than about 2 ppm, less than about 1 ppm, or less than about 0.5 ppm of a compound of formula II or a salt or solvate thereof, and/or less than about 10 ppm, less than about 5 ppm, less than about 3 ppm, less than about 2 ppm, less than about 1 ppm, or less than about 0.5 ppm of a compound of formula III or a salt or solvate thereof.

In certain embodiments, the compound of formula IV in the composition is oxycodone or a salt or solvate thereof, and the composition additionally comprises (i) 8-hydroxyoxycodone or a salt or solvate thereof and/or (ii) 14-hydroxycodeinone or a salt or solvate thereof, wherein the amount of the 8-hydroxyoxycodone is less than about 2500 ppm, less than about 2250 ppm, less than about 2000 ppm, less than about 1750 ppm, less than about 1500 ppm, less than about 1250 ppm, less than about 1000 ppm, less than about 750 ppm, less than about 500 ppm, less than about 400 ppm, less than about 300 ppm, less than about 200 ppm, or less than about 100 ppm of the oxycodone (HPLC peak area ratio; e.g., from about 0.2 ppm to about 1000 ppm of the oxycodone), and the amount of the 14-hydroxycodeinone is less than about 100 ppm, less than about 50 ppm, less than about 40 ppm, less than about 30 ppm, less than about 25 ppm, less than about 20 ppm, less than about 15 ppm, less than about 10 ppm, less than about 5 ppm, less than about 2.5 ppm, or less than about 1 ppm of the oxycodone (HPLC peak area ratio; e.g., from about 0.1 ppm to about 5 ppm, or from about 0.2 ppm to about 2 ppm of the oxycodone). In certain embodiments, the compound of formula IV is oxycodone free base.

In certain embodiments, the compound of formula IV in the composition is an oxycodone salt, and the composition additionally comprises (i) 8-hydroxyoxycodone or a salt or solvate thereof, and/or (ii) 14-hydroxycodeinone or a salt or solvate thereof, wherein the amount of the 8-hydroxyoxycodone is less than about 600 ppm, less than about 500 ppm, less than about 400 ppm, less than about 300 ppm, less than about 200 ppm, less than about 100 ppm, less than about 50 ppm, less than about 25 ppm, or less than about 10 ppm of the oxycodone salt (HPLC peak area ratio; e.g., from about 25 ppm to about 400 ppm of the oxycodone salt), and the amount of the 14-hydroxycodeinone is less than about 25 ppm, less than about 20 ppm, less than about 15 ppm, less than about 10 ppm, less than about 5 ppm, less than about 2 ppm, less than about 1 ppm, or less than about 0.5 ppm of the oxycodone salt (HPLC peak area ratio; e.g., from about 0.05 to about 1 ppm of the oxycodone salt). In certain preferred embodiments, the oxycodone salt is oxycodone hydrochloride.

In certain embodiments, other opioids are contained in the composition comprising the compound of formula IV or salt or solvate thereof, which are contained instead of or in addition to a compound of formula II and/or a compound of formula III or respective salts or solvates thereof:

In certain embodiments, the compound of formula IV in the composition is oxycodone or a salt or solvate thereof, and the composition may not only contain 8-hydroxyoxycodone and/or 14-hydroxycodeinone as described above, but also in addition one or more of the following compounds: oxycodone-N-oxide, 10-ketooxymorphone, 6α-oxycodol (14-hydroxydihydrocodeine), 6β-oxycodol (14-hydroxydihydroisocodeine), 10-hydroxyoxycodone, codeinone, codeine, hydrocodone, oxymorphone, noroxymorphone, pseudo-oxycodone (i.e., 2,2'-bisoxycodone).

The oxycodone-N-oxide, if present, is preferably present in an amount of not more than about 1000 ppm of the oxycodone or salt thereof. The 10-ketooxymorphone, if present, is preferably present in an amount of not more than about 1000 ppm of the oxycodone or salt thereof. The 6α-oxycodol (14-hydroxydihydrocodeine), if present, is preferably present in an amount of not more than about 2500 ppm of the oxycodone or salt thereof. The 6β-oxycodol (14-hydroxydihydroisocodeine), if present, is preferably present in an amount of not more than about 1000 ppm of the oxycodone or salt thereof. The 10-hydroxyoxycodone, if present, is preferably present in an amount of not more than about 1500 ppm of the oxycodone or salt thereof. The codeinone, if present, is preferably present in an amount of not more than about 10 ppm of the oxycodone or salt thereof. The codeine, if present, is preferably present in an amount of not more than about 1000 ppm of the oxycodone or salt thereof. The hydrocodone, if present, is preferably present in an amount of not more than about 1500 ppm of the oxycodone or salt thereof. The oxymorphone, if present, is preferably present in an amount of not more than about 1500 ppm of the oxycodone or salt thereof. The noroxymorphone, if present, is preferably present in an amount of not more than about 1500 ppm of the oxycodone or salt thereof. The pseudo-oxycodone (i.e., 2,2'-bisoxycodone), if present, is preferably present in an amount of not more than about 1000 ppm of the oxycodone or salt thereof.

Compositions comprising a compound of formula IV or salt or solvate thereof, or comprising a mixture or combination of said compound of formula IV or salt or solvate thereof with another opioid, or comprising a mixture or combination of two or more of said compounds of formula IV or salts or solvates thereof are also considered as embodiments of the present invention. Such compositions may be pharmaceutical compositions or dosage forms as described below. For example, such composition may be a pharmaceutical composition or dosage form comprising a mixture or combination of oxycodone and naloxone, wherein both of said compounds or one of said compounds are/is a compound of formula IV or a (pharmaceutically acceptable) salt or solvate thereof.

VIII. Use of the Compound of Formula IV and the Composition Comprising the Compound of Formula IV VIII-A. Use in a Medicament The present invention further provides the use of a compound of formula IV or a pharmaceutically acceptable salt or solvate thereof as API of a medicament.

For this use, the compound of formula IV or the pharmaceutically acceptable salt or solvate thereof may be the compound as described in Section VII.

For this use, the compound of formula IV or the pharmaceutically acceptable salt or solvate thereof may be used in the form of the composition as described in Section VII-A.

For this use, the compound of formula IV or the pharmaceutically acceptable salt or solvate thereof may be used in a dosage form as described in Section IX.

For this use, the medicament may be for treating a medical condition selected from the group consisting of pain, addiction, cough, constipation, diarrhea, insomnia associated with and/or caused by pain, cough or addiction, depression associated with and/or resulting from pain, cough or addiction, or a combination of two or more of the foregoing conditions. In particular, said condition may be pain.

The present invention also provides a method for treating an animal, preferably a mammal (e.g., a human), (in the following: "a patient") using the compound of formula IV or a pharmaceutically acceptable salt or solvate thereof. Said treatment may be of any medical condition which is conventionally treated by administration of the compound of formula IV or a pharmaceutically acceptable salt or solvate thereof to a patient.

Said medical condition may be pain, addiction, cough, constipation, diarrhea, insomnia associated with and/or caused by pain, cough or addiction, depression associated with and/or resulting from pain, cough or addiction, or a combination of two or more of the foregoing conditions. In particular, said condition may be pain.

For this method of treatment, the compound of formula IV or the pharmaceutically acceptable salt or solvate thereof may be the compound as described in Section VII.

For this method of treatment, the compound of formula IV or the pharmaceutically acceptable salt or solvate thereof may be used in the form of the composition as described in Section VII-A.

For this method of treatment, the compound of formula IV or the pharmaceutically acceptable salt or solvate thereof may be used in a dosage form as described in Section IX.

VIII-B. Other Uses

The compound of formula IV or an (optionally pharmaceutically acceptable) salt or solvate thereof, and the composition comprising said compound according to the present invention, may also be used as follows:

In certain embodiments, the compound of formula IV or (optionally pharmaceutically acceptable) salt or solvate thereof, or the composition comprising said compound, is used as an intermediate or starting material for preparing the compound IV in its free form or for preparing another salt or solvate of said compound of formula IV, e.g., for preparing a(nother) pharmaceutically acceptable salt or solvate of said compound of formula IV. For example, when the compound of formula IV is oxycodone, it may be used for preparing oxycodone hydrochloride. For example, when the compound of formula IV is provided as oxycodone sulfate, it may be used for preparing oxycodone hydrochloride or for preparing oxycodone in its free form. Processes for preparing said other salt or solvate which involve a process or compound as described above in the detailed description are also embodiments of the present invention.

In certain embodiments, the compound of formula IV or (optionally pharmaceutically acceptable) salt or solvate thereof, or the composition comprising said compound, is used as an intermediate or starting material for preparing another opioid or a pharmaceutically acceptable salt or solvate thereof or a prodrug thereof, and/or for preparing a medicament containing the compound of formula IV or a pharmaceutically acceptable salt or solvate thereof, or containing another opioid or a pharmaceutically acceptable salt or solvate thereof. For example, when the compound of formula IV is oxycodone, it may be used as starting material for preparing oxymorphone. Processes for preparing said other opioids which involve a process or compound as described above in the detailed description are also embodiments of the present invention.

IX. Dosage Forms

Dosage forms in accordance with the present invention comprise one or more of the compounds or compositions described above and one or more pharmaceutically acceptable excipients. The dosage forms may or may not be abuse-resistant.

Those compounds, compositions, salts or solvates according to the present invention which are or contain an active pharmaceutical ingredient, in particular the opioids and compounds of formula IV which are described in Section VII, the pharmaceutically acceptable salts and solvates thereof (e.g., oxycodone and pharmaceutically acceptable salts and solvates thereof), and the compositions which are described in Section VII-A which contain a compound of formula IV or a pharmaceutically acceptable salt or solvate thereof, can be comprised in a pharmaceutical dosage form or medicament. Other opioids made from compounds, salts or solvates according to the present invention can also be comprised in a pharmaceutical dosage form or medicament. Prodrugs of the opioids described herein can also be comprised in a pharmaceutical dosage form or medicament. Such dosage forms and medicaments are also an embodiment of the present invention.

In addition to said active pharmaceutical ingredient, said dosage forms comprise one or more pharmaceutically acceptable excipients.

A pharmaceutical dosage form of the present invention may comprise (i) an opioid according to present invention or a pharmaceutically acceptable salt or solvate thereof, and (ii) one or more pharmaceutically acceptable excipients. In particular, a pharmaceutical dosage form of the present invention may comprise (i) oxycodone or an oxycodone salt or solvate, all as described above, and (ii) one or more pharmaceutically acceptable excipients.

In certain embodiments, the dosage form comprises oxycodone or a pharmaceutically acceptable salt or solvate thereof, wherein said compound has the properties as described in Section VII, and/or are contained in a composition as described in Section VII-A, and/or has been prepared according to a process of the present invention. In one embodiment, the oxycodone salt is oxycodone hydrochloride.

In certain embodiments, the dosage form comprises a combination of oxycodone or a salt or solvate thereof which has the properties as described in Section VII, and/or is contained in a composition as described in Section VII-A, and/or has been prepared according to a process of the present invention, with another opioid. In certain embodiments, the dosage form comprises a combination of oxycodone or a salt or solvate thereof which has the properties as described in Section VII, and/or is contained in a composition as described in Section VII-A, and/or has been prepared according to a process of the present invention, with an opioid receptor antagonist. For example, a dosage form of the present invention may comprise a combination of oxycodone or a pharmaceutically acceptable salt or solvate thereof (such as oxycodone hydrochloride) and naloxone or a pharmaceutically acceptable salt or solvate thereof (such as naloxone hydrochloride).

In certain embodiments, the dosage form is selected from the group consisting of oral dosage forms (e.g., tablets, capsules, suspensions, solutions, etc.), injectable dosage forms, rectal dosage forms (e.g., suppositories), and transdermal dosage forms (e.g., patches).

In certain embodiments, a pharmaceutical composition or dosage form comprising at least one or a combination of the active pharmaceutical ingredients according to the present invention additionally comprises a compound of formula II and/or a compound of formula III.

In certain embodiments, a pharmaceutical composition or dosage form comprises at least one or a combination of the active pharmaceutical ingredients according to the present invention and additionally comprises a compound of formula II and/or a compound of formula III, wherein the combined amount of compound of formula II and compound of formula III is less than about 3000 ppm, less than about 2750 ppm, less than about 2500 ppm, less than about 2250 ppm, less than about 2000 ppm, less than about 1750 ppm, less than about 1500 ppm, or less than about 1250 in relation to the amount of the active pharmaceutical ingredient.

In certain embodiments, the combined amount of the compound of formula II and III in the pharmaceutical composition or dosage form is less than about 1000 ppm, less than about 750 ppm, less than about 500 ppm, less than about 400 ppm, less than about 300 ppm, or less than about 275 ppm in relation to the amount of the active pharmaceutical ingredient.

In certain embodiments, the combined amount of the compound of formula II and III in the pharmaceutical composition or dosage form is less than about 250 ppm, less than about 225 ppm, less than about 200 ppm, less than about 175 ppm, less than about 150 ppm, or less than about 125 ppm in relation to the amount of the active pharmaceutical ingredient.

In certain embodiments, the combined amount of the compound of formula II and III in the pharmaceutical composition or dosage form is less than about 100 ppm, less than about 90 ppm, less than about 80 ppm, less than about 70 ppm, less than about 60 ppm, less than about 50 ppm, less than about 40 ppm, less than about 30 ppm, or less than about 20 ppm in relation to the amount of the active pharmaceutical ingredient.

In certain embodiments, the combined amount of the compound of formula II and III in the pharmaceutical composition or dosage form is less than about 10 ppm, less than about 8 ppm, less than about 6 ppm, less than about 4 ppm, or less than about 2 ppm in relation to the amount of the active pharmaceutical ingredient.

In certain embodiments, the combined amount of the compound of formula II and III in the pharmaceutical composition or dosage form is less than about 1 ppm, less than about 0.8 ppm, less than about 0.6 ppm, less than about 0.4 ppm, less than about 0.3 ppm, less than about 0.2 ppm, or less than about 0.1 ppm in relation to the amount of the active pharmaceutical ingredient.

In certain embodiments, the combined amount of the compound of formula II and III in the pharmaceutical composition or dosage form has a lower limit of about 0.05 ppm of the active pharmaceutical ingredient. In certain embodiments, the lower limit is about 0.1 ppm, about 0.3 ppm, about 0.5 ppm, about 0.7 ppm, about 1 ppm, about 1.5 ppm, about 2 ppm, or about 3 ppm in relation to the amount of the active pharmaceutical ingredient.

In certain embodiments wherein the API is a compound which is not a compound of formula II or a salt or solvate thereof, a pharmaceutical composition or dosage form comprising at least one or a combination of the active pharmaceutical ingredients according to present invention comprises less than 500 ppm, less than about 250 ppm, less than about 200 ppm, less than about 100 ppm, less than about 50 ppm or less than about 40 ppm of a compound of formula II (HPLC peak area ratio). In certain embodiments, it may be less than about 30 ppm, less than about 25 ppm, less than about 20 ppm, less than about 15 ppm, less than about 10 ppm, less than about 5 ppm, or less than about 2.5 ppm (HPLC peak area ratio). In certain embodiments, it may be less than about 1 ppm, less than about 0.8 ppm, less than about 0.6 ppm, less than about 0.6 ppm, less than about 0.4 ppm, less than about 0.2 ppm, or less than about 0.1 ppm (HPLC peak area ratio).

In certain embodiments, a pharmaceutical composition or dosage form comprising at least one or a combination of the active pharmaceutical ingredients according to present invention comprises less than about 200 ppm, less than about 150 ppm, less than about 100 ppm, or less than about 50 ppm of a compound of formula II or a salt or solvate thereof, and/or less than about 1000 ppm, less than about 750 ppm, less than about 500 ppm, less than about 300 ppm, less than about 200 ppm, or less than about 100 ppm of a compound of formula III or a salt or solvate thereof.

In certain embodiments, a pharmaceutical composition or dosage form comprising at least one or a combination of the active pharmaceutical ingredients according to present invention comprises less than about 100 ppm, less than about 50 ppm, less than about 25 ppm, less than about 20 ppm, less than about 15 ppm, or less than about 10 ppm of a compound of formula II or a salt or solvate thereof, and/or less than about 300 ppm, less than about 200 ppm, less than about 100 ppm, less than about 50 ppm, less than about 25 ppm, or less than about 10 ppm of a compound of formula III or a salt or solvate thereof.

In certain embodiments, a pharmaceutical composition or dosage form comprising at least one or a combination of the active pharmaceutical ingredients according to present invention comprises less than about 25 ppm, less than about 20 ppm, less than about 15 ppm, less than about 10 ppm, less than about 5 ppm, or less than about 1 ppm of a compound of formula II or a salt or solvate thereof, and/or less than about 100 ppm, less than about 50 ppm, less than about 25 ppm, less than about 10 ppm, or less than about 5 ppm of a compound of formula III or a salt or solvate thereof.

In certain embodiments, a pharmaceutical composition or dosage form comprising at least one or a combination of the active pharmaceutical ingredients according to present invention comprises less than about 10 ppm, less than about 5 ppm, less than about 4 ppm, less than about 3 ppm, less than about 2 ppm, less than about 1 ppm, or less than about 0.5 ppm of a compound of formula II or a salt or solvate thereof, and/or less than about 10 ppm, less than about 5 ppm, less than about 3 ppm, less than about 2 ppm, less than about 1 ppm, or less than about 0.5 ppm of a compound of formula III or a salt or solvate thereof.

In certain embodiments, the dosage form comprises as an API oxycodone or a pharmaceutically acceptable salt or solvate thereof, wherein said compound has the properties as described in Section VII and/or has been prepared according to a process of the present invention. In certain preferred embodiments, the dosage form comprises oxycodone or a pharmaceutically acceptable oxycodone salt, e.g., oxycodone hydrochloride, as an active pharmaceutical ingredient.

In said embodiments, the dosage form may be selected from the group consisting of oral dosage forms (e.g., tablets, capsules, suspensions, solutions, etc.), injectable dosage forms, rectal dosage forms (e.g., suppositories), and transdermal dosage forms (e.g., patches). Dosage forms for oral administration may be presented as tablets, capsules, liquid formulations, troches, lozenges, powders, granules, microparticles (e.g., microcapsules, microspheres and the like), or buccal tablets.

In certain embodiments, oral dosage forms of the present invention may be in the form of tablets (sustained release and/or immediate release), solutions, suspensions, etc.

Oral dosage forms can provide a controlled release (sustained release or delayed release) or an immediate release of the active pharmaceutical ingredient. One of the conventional excipients may be a pharmaceutically acceptable carrier. Suitable pharmaceutically acceptable carriers include but are not limited to, e.g., alcohols, gum arabic, vegetable oils, benzyl alcohols, polyethylene glycols, gelate, carbohydrates such as lactose, amylose or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, etc. The dosage form may further comprise an inert diluent such as lactose; granulating and disintegrating agents such as cornstarch; binding agents such as starch; and lubricating agents such as magnesium stearate. The tablets may be uncoated or they may be coated by known techniques for elegance or to provide a controlled release of the drug (a sustained release, a delayed release or a pulsatile release) of the pharmaceutical composition.

The pharmaceutical preparations can be sterilized and if desired mixed with auxiliary agents, e.g., lubricants, disintegrants, preservatives, stabilizers, wetting agents, emulsifiers, salts for influencing osmotic pressure buffers, coloring, flavoring and/or aromatic substances and the like.

The compositions intended for oral use may be prepared according to any method known in the art and such compositions may contain one or more agents selected from the group consisting of inert, non-toxic pharmaceutically acceptable excipients which are suitable for the manufacture of the pharmaceutically acceptable dosage forms.

In certain embodiments, the sustained release dosage form may optionally comprise particles containing an opioid pharmaceutical composition described above. In certain embodiments, the particles have a diameter from about 0.1 mm to about 2.5 mm, preferably from about 0.5 mm to about 2 mm. The particles may be film coated with a material that permits release of the active at a sustained rate in an aqueous medium. The film coat may be chosen so as to achieve, in combination with the other ingredients of the dosage form, desired release properties. The sustained release coating formulations of the present invention should be capable of producing a strong, continuous film that is smooth and elegant, capable of supporting pigments and other coating additives, non-toxic, inert, and tack-free.

Coated Beads

In certain embodiments of the present invention a hydrophobic material is used to coat inert pharmaceutical beads such as nu pariel 18/20 beads, and a plurality of the resultant solid sustained release beads may thereafter be placed in a gelatin capsule in an amount sufficient to provide an effective sustained release dose of the opioid pharmaceutical composition when ingested and contacted by an environmental fluid, e.g., gastric fluid or dissolution media.

The sustained release bead formulations of the present invention slowly release the active of the present invention, e.g., when ingested and exposed to gastric fluids, and then to intestinal fluids.

The sustained release profile of the formulations of the invention can be altered, for example, by varying the amount of overcoating with the hydrophobic material, altering the manner in which a plasticizer is added to the hydrophobic material, by varying the amount of plasticizer relative to hydrophobic material, by the inclusion of additional ingredients or excipients, by altering the method of manufacture, etc.

The dissolution profile of the ultimate product may also be modified, for example, by increasing or decreasing the thickness of the retardant coating.

Spheroids or beads coated with the agent(s) of the present invention are prepared, e.g., by dissolving the pharmaceutical compositions in water and then spraying the solution onto a substrate, for example, nu pariel 18/20 beads, using a Wurster insert. Optionally, additional ingredients may be added prior to coating the beads in order to assist the binding of the pharmaceutical compositions to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the active(s) from the hydrophobic sustained release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g., triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the agent(s) by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined sustained release of the pharmaceutical composition when the coated substrate is exposed to aqueous solutions, e.g., gastric fluid, may be applied. After coating with the hydrophobic material, a further overcoat of a film-former, such as, e.g., Opadry®, may be optionally applied to the beads. This overcoat is provided, if at all, e.g., in order to substantially reduce agglomeration of the beads.

The release of the pharmaceutical composition(s) from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in an environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,899; 4,063,064; and 4,088,864.

Matrix Formulations

In other embodiments of the present invention, the sustained release formulation is achieved via a sustained release matrix optionally having a sustained release coating as set forth herein. The materials suitable for inclusion in the sustained release matrix may depend on the method used to form the matrix.

For example, a matrix in addition to the pharmaceutical compositions described above may include hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting sustained release of the pharmaceutical composition(s) and which melts (or softens to the extent necessary to be extruded) may be used in accordance with the present invention.

The oral dosage form may contain between 1% and 80% (by weight) of one or more hydrophilic or hydrophobic material(s).

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing. Of these materials, acrylic polymers, e.g., Eudragit® RSPO, the cellulose ethers, e.g., hydroxyalkylcelluloses and carboxyalkylcelluloses are preferred.

Preferred hydrophobic materials are water-insoluble with more or less pronounced hydrophilic and/or hydrophobic trends. Preferably, the hydrophobic materials useful in the invention have a melting point from about 40° C. to about 200° C., preferably from about 45° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes are waxes as defined in Fette, Seifen, Anstrichmittel 76, 135 (1974) and include, for example, beeswax, glycowax, castor wax and carnauba wax.

Suitable hydrophobic materials which may be used in accordance with the present invention include long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° C. and 90° C. are preferred. Of the long chain hydrocarbon materials, fatty (aliphatic) alcohols are pre-ferred in certain embodiments. The oral dosage form may contain up to 60% of at least one long chain hydrocarbon.

In certain embodiments, a combination of two or more hydrophobic materials is included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of API release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by weight) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by weight) of the total dosage.

In one embodiment, the ratio of, e.g., the at least one hydroxyalkyl cellulose or acrylic resin to the at least one aliphatic alcohol/polyalkylene glycol determines, to a (w/w) of the at least one hydroxyalkyl cellulose to the at least one aliphatic alcohol/polyalkylene glycol of between 1:2 and 1:4 is preferred, with a ratio of between 1:3 and 1:4 being particularly preferred.

In certain embodiments, the oral dosage form contains at least one polyalkylene glycol. The amount of the at least one polyalkylene glycol in the oral dosage form may be up to 60%. The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

In certain embodiments, the sustained release matrix may comprise polyethylene oxide. In certain embodiments polyethylene oxide comprises from about 40% to about 95% of the dosage form. In certain embodiments polyethylene oxide comprises from about 50% to about 95% of the dosage form. In certain embodiments polyethylene oxide comprises from about 55% to about 90% of the dosage form. In certain embodiments polyethylene oxide comprises from about 60% to about 90% of the dosage form.

Another suitable sustained release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a sustained release matrix may also contain suitable quantities of other materials, e.g., diluents, lubricants, binders, granulating aids, colorants, flavorants and glidants that are conventional in the pharmaceutical art.

Matrix-Particulates

In order to facilitate the preparation of a solid, sustained release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, and an opioid according to present invention; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose granules with water.

In yet other alternative embodiments, a spheronizing agent, together with the active can be spheronized to form spheroids. Microcrystalline cellulose is a preferred spheronizing agent. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, is preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g., a wax, and incorporating a powdered drug therein. To obtain a sustained release dosage form, it may be necessary to incorporate an additional hydrophobic substance, e.g., ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w). For purposes of the present invention, a wax-like substance is defined as any material which is normally solid at room temperature and has a melting point of from about 25° to about 100° C.

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g., diluents, lubricants, binders, granulating aids, colorants, flavorants and glidants that are conventional in the pharmaceutical art in amounts up to about 50% of the particulate if desired.

Specific examples of pharmaceutically acceptable carriers and excipients that may be used to formulate oral dosage forms are described in the Handbook of Pharmaceutical Excipients, American Pharmaceutical Association (1986).

Melt Extrusion Multiparticulates

The preparation of a suitable melt-extruded matrix according to the present invention may, for example, include the steps of blending the API together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the API for a time period of from about 8 to about 24 hours.

An optional process for preparing the melt extrusions of the present invention includes directly metering into an extruder a hydrophobic material, the opioid API, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980).

In yet another preferred embodiment, the extrudate can be shaped into tablets as set forth in U.S. Pat. No. 4,957,681 (Klimesch, et. al.), described in additional detail above.

Optionally, the sustained release melt-extruded multiparticulate systems or tablets can be coated, or the gelatin capsule containing the multiparticulates can be further coated, with a sustained release coating such as the sustained release coatings described above. Such coatings preferably include a sufficient amount of hydrophobic material to obtain a weight gain level from about 2 to about 30 percent, although the overcoat may be greater depending upon the desired release rate, among other things.

The melt-extruded unit dosage forms of the present invention may further include combinations of melt-extruded particles before being encapsulated. Furthermore, the unit dosage forms can also include an amount of an immediate release agent for prompt release. The immediate release agent may be incorporated, e.g., as separate pellets within a gelatin capsule, or may be coated on the surface of the multiparticulates after preparation of the dosage forms (e.g., sustained release coating or matrix-based). The unit dosage forms of the present invention may also contain a combination of sustained release beads and matrix multiparticulates to achieve a desired effect.

The sustained release formulations of the present invention preferably slowly release the agent(s), e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the API, which can be added thereafter to the extrudate. Such formulations typically will have the agents blended together with the extruded matrix material, and then the mixture would be tableted in order to provide a slow release formulation.

Coatings

The dosage forms of the present invention may optionally be coated with one or more materials suitable for the regulation of release or for the protection of the formulation. In one embodiment, coatings are provided to permit either pH-dependent or pH-independent release. A pH-dependent coating serves to release the active in desired areas of the gastrointestinal (GI) tract, e.g., the stomach or small intestine, such that an absorption profile is provided which is capable of providing at least about eight hours and preferably about twelve hours to up to about twenty-four hours of the therapeutic effect (such as analgesia) to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the API is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493.

Other examples of sustained release formulations and coatings which may be used in accordance with the present invention include those described in U.S. Pat. Nos. 5,324,351; 5,356,467, and 5,472,712.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

Acrylic Polymers

In other preferred embodiments of the present invention, the hydrophobic material comprising the sustained release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly (methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Evonik. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Evonik under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL and 90% Eudragit® RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethyl-cellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Sustained Release Osmotic Dosage Form

Sustained release dosage forms according to the present invention may also be prepared as osmotic dosage formulations. The osmotic dosage forms preferably include a bilayer core comprising a drug layer (e.g., containing oxycodone as described above) and a delivery or push layer, wherein the bilayer core is surrounded by a semipermeable wall and optionally having at least one passageway disposed therein.

The expression "passageway" as used for the purpose of the present description, includes aperture, orifice, bore, pore, porous element through which an API (e.g., oxycodone hydrochloride) may be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The dosage form can be manufactured with one or more passageways in spaced-apart relation on one or more surfaces of the dosage form. A passageway and equipment for forming a passageway are disclosed in U.S. Pat. Nos. 3,845,770; 3,916,899; 4,063,064 and 4,088,864. Passageways comprising sustained-release dimensions sized, shaped and adapted as a releasing-pore formed by aqueous leaching to provide a releasing-pore of a sustained-release rate are disclosed in U.S. Pat. Nos. 4,200,098 and 4,285,987.

In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of the osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the active pharmaceutical ingredient (e.g., oxycodone hydrochloride) from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropyl isopropyl cellulose, hydroxypropylbutylcellulose, and hydroxypropylpentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tert-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-di-tert butyl-phenol, α-tocopherol, and propylgallate.

In certain alternative embodiments, the dosage form comprises a homogenous core comprising an active pharmaceutical ingredient (e.g., oxycodone), a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the opioid API.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ ($cm^2$/hr atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of from 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

Suppositories

The sustained release formulations of the present invention may be formulated as a pharmaceutical suppository for rectal administration comprising a suitable suppository base, and a pharmaceutical opioid composition. Preparation of sustained release suppository formulations is described in, e.g., U.S. Pat. No. 5,215,758.

Prior to absorption, the drug must be in solution. In the case of suppositories, solution must be preceded by dissolution of the suppository base, or the melting of the base and subsequent partition of the drug from the suppository base into the rectal fluid. The absorption of the drug into the body may be altered by the suppository base. Thus, the particular suppository base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factors affecting the absorption of drugs from suppositories administered rectally include suppository vehicle, absorption site pH, drug pKa, degree of ionization, and lipid solubility.

The suppository base chosen should be compatible with the active of the present invention. Further, the suppository base is preferably non-toxic and nonirritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20 percent to about 90 percent of the total weight of the suppository. Preferably, the amount of suppository base in the suppository is from about 65 percent to about 80 percent, of the total weight of the suppository.

The following examples are meant to illustrate, but in no way to limit, the present invention.

EXAMPLES

Comparative Example 1: Preparation of Oxycodone Free Base According to US 2010/0048905

Example 1 from US 2010/0048905 was repeated as follows.

1. Thebaine (3.22 g, 10.3 mmol) was charged into a 100 mL reaction vessel equipped with a temperature probe, an overhead stirrer and a reflux condenser as a slurry in deionized water (9 mL).

2. The reaction mixture was stirred at 300 rpm, while maintaining an internal temperature of 20° C.

3. Formic acid (88%, 6 mL, 139.9 mmol) was added to the reaction mixture. During the formic acid addition, the solids readily dissolved, and the temperature of the reaction mixture increased to 30° C.

4. After the temperature of the reaction mixture had cooled to 20° C., 35% hydrogen peroxide (1.36 mL, 15.8 mmol) and sulfuric acid (0.165 mL, 2.99 mmol) were added to the reaction mixture.

5. The reaction was stirred (300 rpm) at 20° C. for 16 hours, until greater than 95% of thebaine was consumed by the reaction.

6. 0.30 g of 5% palladium on carbon was added to the reaction mixture. The reaction mixture was heated to 45° C. and stirred at 45° C. for 2 hours.

7. The reaction mixture was then heated to 60° C. and stirred at 60° C. for 2 additional hours.

8. The reaction mixture was then cooled to 20° C. and stirred at 20° C. for 16 hours. Nothing precipitated out of the reaction mixture at this temperature.

9. The reaction mixture was then filtered through a plug of celite.

10. The filtrate was basified to a pH of about 9.5 with concentrated ammonium hydroxide, to precipitate a solid.

11. The composition containing the precipitate was allowed to stir at room temperature for 1 hour.

12. The composition was then filtered, the solid was washed with water (3×15 mL) and dried on the filter under vacuum for 1 hour. The solid was further dried in a vacuum oven at 80° C. for 16 hours to yield 2.33 g of the solid.

Analysis of the solid by the HPLC method described in USP 34-NF 29, First Supplement, Monograph on Oxycodone Hydrochloride, page 5016, Assay described in right column (official from Dec. 1, 2011) showed that the composition had an HPLC peak area ratio of oxycodone:14-hydroxycodeinone:8α-hydroxyoxycodone:8β-hydroxyoxycodone of 30,971,454:1,892,286:362,475:58,023. In other words, oxycodone base comprised 90.4% of the composition, 14-hydroxycodeinone comprised 61,098 ppm of the composition, 8α-hydroxyoxycodone comprised 11,704 ppm of the composition, 8β-hydroxyoxycodone comprised 1,873 ppm of the composition.

Example 1: Preparation of 14-Hydroxycodeinone Sulfate

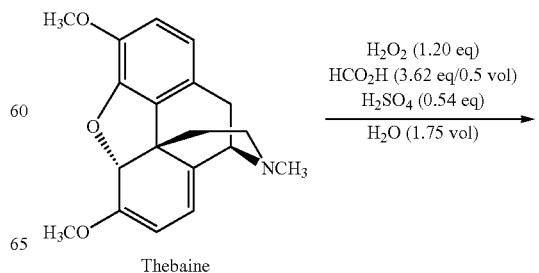

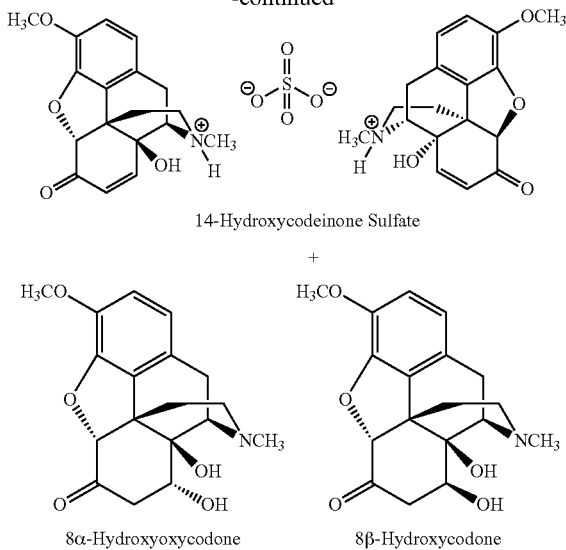

14-Hydroxycodeinone Sulfate

+

8α-Hydroxyoxycodone    8β-Hydroxycodone 14-hydroxycodeinone sulfate was prepared as follows:

1. Into a 100 mL jacketed vessel equipped with a temperature probe, overhead stirrer and an addition funnel, thebaine (12.0 g, 38.6 mmol) was charged as a slurry in deionized water (18 mL).
2. The jacket temperature for the vessel was set to 20° C. and the slurry was stirred at 300 rpm.
3. 88% formic acid (6 mL, 140 mmol) was added into the reaction mixture. The solids readily dissolved into solution upon this addition. During the formic acid addition, the temperature of the reaction mixture increased to 29° C.
4. Sulfuric acid (1.15 mL, 21 mmol) was added to the solution, and the solution was stirred at 300 rpm.
5. After the solution temperature had cooled below 22° C., 35% hydrogen peroxide (4.00 mL, 46.5 mmol) was added to the reaction over 15 minutes, using the addition funnel.
6. After the peroxide addition was complete, an additional 3 mL of deionized water was added to the reaction through the addition funnel.
7. The reaction solution was allowed to stir (300 rpm) at 20° C. for 30 minutes.
8. The reaction was then heated to 30° C. and held at 30° C., while stirring at 300 rpm for 8 hours.
9. The reaction mixture was then cooled to 20° C. over 2 hours and stirred (300 rpm) for an additional 8 hours at this temperature.
10. The resulting solution was cooled to 0° C. After stirring for 1 hour at 0° C., no solids had precipitated out of solution.
11. While stirring at 300 rpm, the resulting solution was warmed to 20° C. and treated with 12 mL of methanol, followed by 12 mL of tetrahydrofuran and 24 mL of tert-butyl methyl ether (addition of antisolvents). The solution became visually cloudy, but no precipitation occurred.
12. The mixture was then treated with an additional 12 mL of methanol, followed by 24 mL of tert-butyl methyl ether. Precipitation of solids occurred after the antisolvent addition while stirring (300 rpm) at 20° C.
13. The suspension was allowed to stir (300 rpm) at 20° C. for 1 hour.
14. The solids were filtered under vacuum using a Buchner funnel, with Whatman #1 filter paper, and the solids were washed with tert-butyl methyl ether (2×12 mL).
15. The solids were dried under vacuum on the Buchner funnel for 1 hour, before being transferred to a drying oven and dried under vacuum at 80° C. for 16 hours.
16. 9.32 g (12.9 mmol (calculated without water of crystallization), 66.6% yield) of 14-hydroxycodeinone sulfate was isolated as fine yellow-white crystals and analyzed by the HPLC method described in USP 34-NF 29, First Supplement, Monograph on Oxycodone Hydrochloride, page 5016, Assay described in right column (official from Dec. 1, 2011). Analysis showed an HPLC area ratio of 14-hydroxycodeinone sulfate:8α-hydroxyoxycodone:8β-hydroxyoxycodone of 23,193,784:22,729:18,875. In other words, the composition comprised 99.56% 14-hydroxycodeinone (based on HPLC area percent), 980 ppm of 8α-hydroxyoxycodone (based on HPLC area percent) and 815 ppm 8β-hydroxyoxycodone (based on HPLC area percent).

About 4.2 molar equivalents of total acid per molar equivalent of thebaine were used in this example. The molar ratio of sulfuric acid to formic acid was about 1:6.7. No precipitation was observed in step 10, but precipitation could be achieved by the total amount of antisolvent added in steps 11 and 12.

Example 2: Preparation of Oxycodone Base

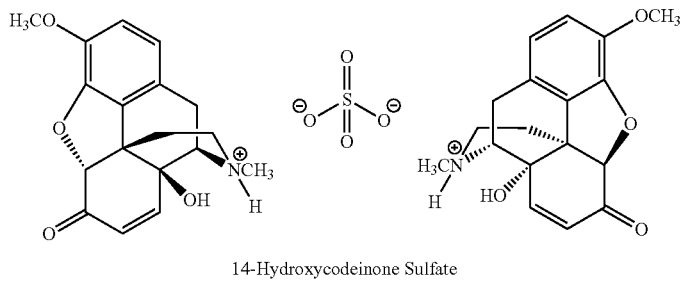

14-Hydroxycodeinone Sulfate

+

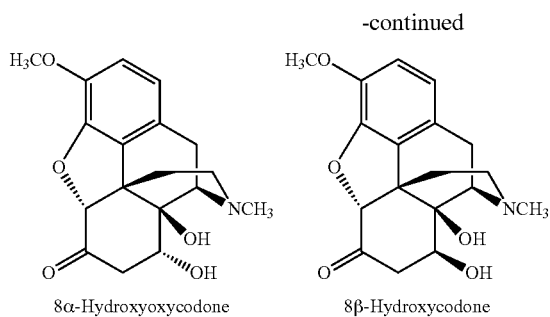
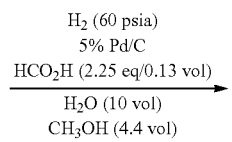

8α-Hydroxyoxycodone          8β-Hydroxycodone

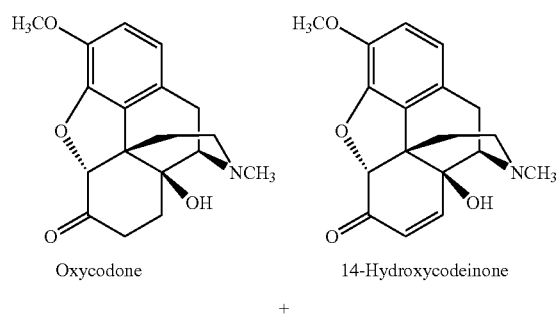

Oxycodone          14-Hydroxycodeinone

+

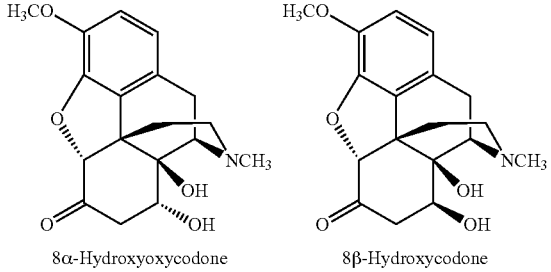

8α-Hydroxyoxycodone          8β-Hydroxycodone

A composition comprising 99.13% of oxycodone base, 26 ppm 14-hydroxycodeinone, 565 ppm of 8α-hydroxyoxycodone and 298 ppm of 8β-hydroxyoxycodone, based on HPLC area percent, was prepared as follows:

1. Into a 300 mL hydrogenation vessel equipped with a magnetic stir bar, 14-hydroxycodeinone sulfate obtained in Example 1 (9.01 g, 12.43 mmol (calculated without water of crystallization)), deionized water (90 mL) and methanol (40 mL) were charged. The majority of solids dissolved into solution.

2. Formic acid (1.20 mL, 28.0 mmol) and 5% palladium on carbon (0.065 g) were added into the reaction mixture.

3. The vessel was sealed, stirred at 750 rpm and heated to 40° C.

4. The mixture was then hydrogenated at 60 psia (413.69 kPa) for 5 hours.

5. The reaction was vented, purged with nitrogen, vented and hydrogenated at 60 psia (413.69 kPa) for an additional 1 hour.

6. The reaction was vented, purged with nitrogen and cooled to 22° C. over 8 hours.

7. The reaction mixture was filtered through filter paper to remove the palladium on carbon and the filtrate was sampled for HPLC analysis by the USP method referred to in Example 1. The results showed that less than 1% 14-hydroxycodeinone remained by HPLC area %.

8. The filtrate was transferred to a 250 mL Erlenmeyer flask equipped with a magnetic stir bar and pH probe. The solution pH was 2.64.

9. While stirring at 200 rpm, the solution was basified by adding 4.9 mL of 28% ammonium hydroxide; solids precipitated out of solution during the ammonium hydroxide addition and the final pH of the mixture was 9.08.

10. The mixture was allowed to stir (200 rpm) at 22° C. for an additional 30 minutes.

11. The solids were filtered under vacuum using a Buchner funnel with Whatman#2 filter paper, and the solids were washed with water (2×10 mL).

12. The solids were dried under vacuum on the Buchner funnel for 2 hours, before being transferred to a drying oven and dried under vacuum to a constant weight.

13. Isolated: 6.59 g (20.9 mmol, 84% yield) of oxycodone (base) as a white crystalline powder as analyzed by HPLC (USP method referred to in Example 1). The HPLC area ratio of oxycodone:14-hydroxycodeinone:8α-hydroxyoxycodone:8β-hydroxyoxycodone was 32,465,231:855 (26 ppm):18,285 (565 ppm):9,643 (298 ppm). In other words, the composition contained 99.13% of oxycodone base, 26 ppm of 14-hydroxycodeinone, 565 ppm of 8α-hydroxyoxycodone and 298 ppm of 8β-hydroxyoxycodone, based on HPLC area percent.

Example 3: Preparation of Oxycodone Hydrochloride

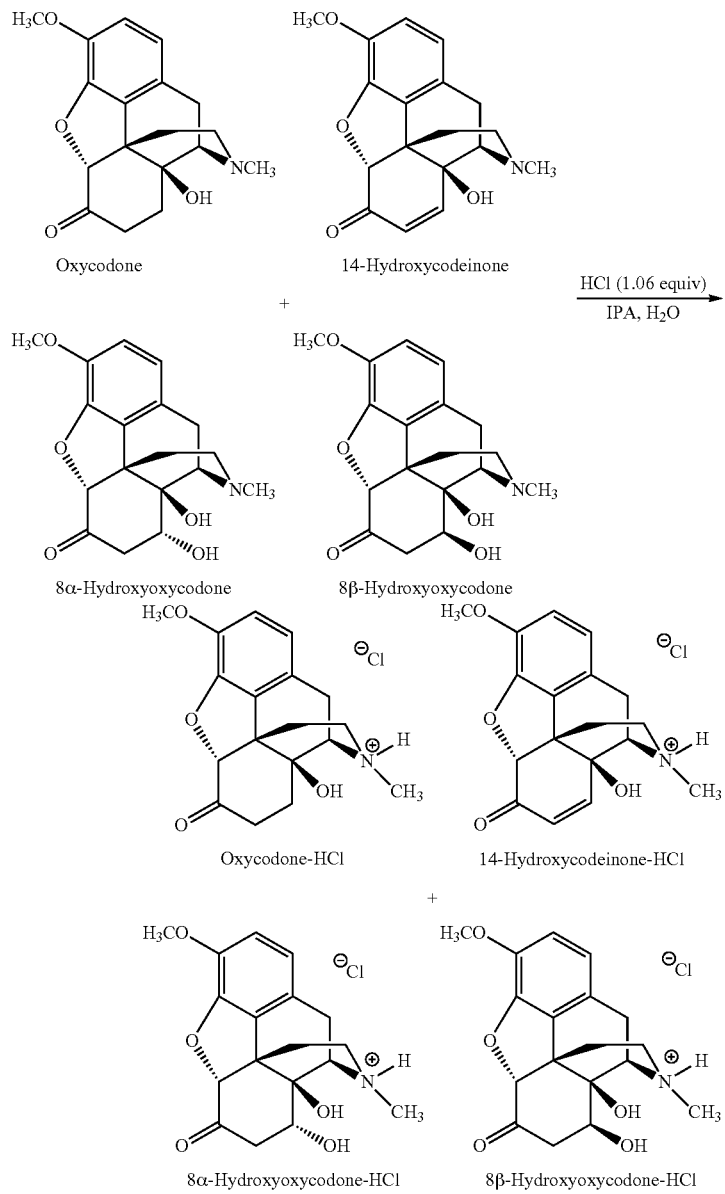

A composition comprising 99.72% of oxycodone hydrochloride, 9 ppm of 14-hydroxycodeinone hydrochloride, 103 ppm of 8α-hydroxyoxycodone hydrochloride, and 191 ppm of 8β-hydroxyoxycodone hydrochloride, based on HPLC area percent, was prepared as follows:

1. Into a 300 mL jacketed reaction vessel equipped with a temperature probe, reflux condenser, and overhead stirrer, was charged oxycodone (4.01 g, 12.0 mmol), deionized water (6 mL) and isopropanol (45 mL). The oxycodone comprised 99.13% of oxycodone, 26 ppm of 14-hydroxycodeinone, 565 ppm of 8α-hydroxyoxycodone, and 298 ppm of 8β-hydroxyoxycodone.

2. The mixture was stirred at 250 rpm and the external jacket of the vessel was heated to 80° C.

3. When the internal temperature of the mixture had reached 40° C., 37% hydrochloric acid (1.05 mL, 12.8 mmol) was added to the reaction vessel.

4. When the internal temperature of the mixture had reached 74° C., all visible solids were dissolved in the reaction mixture.

5. The mixture was stirred at 250 rpm for 30 minutes at a temperature of 74° C., before being gradually cooled to 6° C., over 8 hours. The mixture was stirred for an additional 8 hours at 6° C.

7. The resulting solids were filtered under vacuum using a Buchner funnel with Whatman#2 filter paper, and the solids were collected and washed with a 20:1 mixture of isopropanol:deionized water (30 mL).

8. The solids were dried under vacuum on the Buchner funnel for 3 hours, before being transferred to a drying oven and dried under vacuum to a constant weight. The solids contained 3.40 g (9.7 mmol, 80.3% yield) of oxycodone hydrochloride as fine white crystals, containing 9 ppm of 14-hydroxycodeinone hydrochloride (based on HPLC area percent using the USP method referred to in Example 1), 103 ppm of 8α-hydroxyoxycodone hydrochloride (based on HPLC area percent) and 191 ppm of 8β-hydroxyoxycodone hydrochloride (based on HPLC area percent).

A comparison of the components of the oxycodone base (OXY base), the solid oxycodone hydrochloride (OXY—HCl (dried solid)), and the filtrate of the oxycodone hydrochloride (OXY—HCl (filtrate)) is given in Table 1:

TABLE 1

|  | OXY base (starting material) | OXY-HCl (dried solid) | OXY-HCl (filtrate) |
| --- | --- | --- | --- |
| Oxycodone (OXY) | 99.13% | 99.72% | 96.78% |
| 14-Hydroxycodeinone | 26 ppm | 9 ppm | 208 ppm |
| 8α-hydroxyoxycodone | 565 ppm | 103 ppm | 149 ppm |
| 8β-hydroxyoxycodone | 298 ppm | 191 ppm | 173 ppm |

Example 4: Preparation of 14-Hydroxycodeinone Sulfate

1. Thebaine (30.02 g, 96.4 mmol) was charged into a 100 mL jacketed vessel equipped with a temperature probe, overhead stirrer and a funnel as a slurry in deionized water (60 mL).
2. The jacket temperature for the vessel was set to 20° C., and the slurry was stirred at 400 rpm.
3. Formic acid (88%, 10.5 mL, 244.9 mmol) was added to the reaction mixture. Upon addition of the formic acid, the solids readily dissolved.
4. Sulfuric acid (3.00 mL, 54.3 mmol) was added to the reaction mixture.
5. During the acid addition, the temperature of the reaction mixture increased to 30° C.
6. After the temperature of the reaction mixture had cooled to below 25° C., hydrogen peroxide (35%, 9.00 mL, 104.7 mmol) was added to the reaction mixture over 15 minutes.
7. After the addition of hydrogen peroxide was complete, an additional 6.75 mL of deionized water was added to the reaction. The reaction mixture was allowed to stir (400 rpm) at 20° C. for 20 minutes.
8. The reaction mixture was then heated to 29° C. and held at 29° C., while stirring at 400 rpm for 21 hours.
9. The reaction was then heated to 35° C. over 40 minutes and stirred for an additional 18 hours at 35° C.
10. Half of the reaction material (55 mL) was removed from the reaction at 35° C., and the remaining material was cooled to 10° C. at a rate of −1° C. per 5 minutes, while stirring at 200 rpm. When the solution temperature had dropped to 20° C., a solid composition precipitated out of the solution to form a suspension.
11. The suspension was stirred (200 rpm) at 10° C. for 1 hour.
12. Isopropanol (30 mL) was added to the reaction mixture, and the mixture was stirred (200 rpm) at 10° C. for an addition 1 hour.
13. The solids were filtered under vacuum using a Buchner funnel, with Whatman #1 filter paper, and washed with isopropanol (2×30 mL).
14. The solids were then dried under vacuum on the Buchner funnel for 1 hour, before being transferred to a drying oven and dried under vacuum at 80° C. for 16 hours to afford 9.69 g (13.4 mmol, 55.5% yield) of fine yellow-white crystals.

Analysis of the fine yellow-white crystals showed the composition had an HPLC peak area ratio of 14-hydroxycodeinone sulfate:8α-hydroxyoxycodone:8β-hydroxyoxycodone of 37,461,836:7,981 (216 ppm):55,441 (1,480 ppm) (based on HPLC area percent using the USP method referred to in Example 1). In other words, the composition comprised about 95.14% 14-hydroxycodeinone sulfate, about 216 ppm 8α-hydroxyoxycodone and about 1480 ppm 8β-hydroxyoxycodone.

Example 5: Preparation of Oxycodone Sulfate

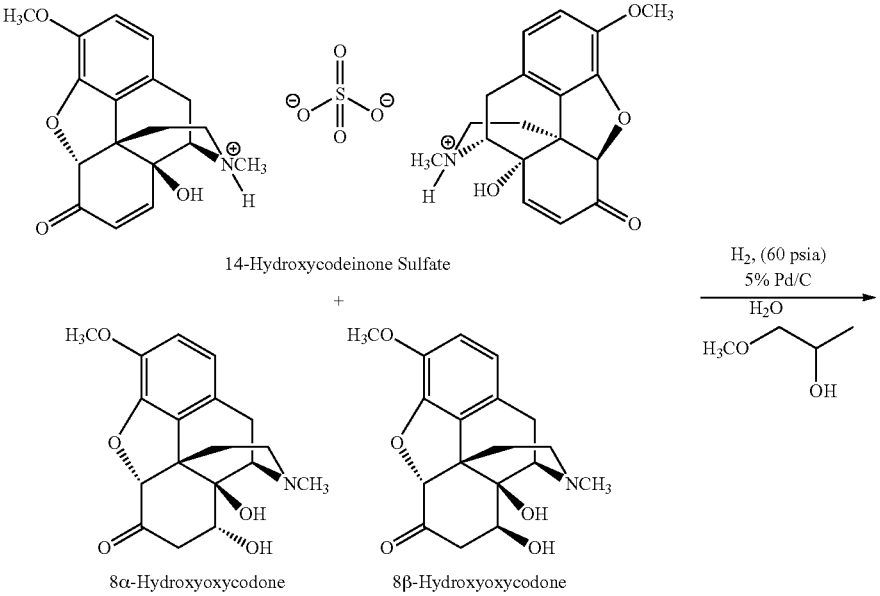

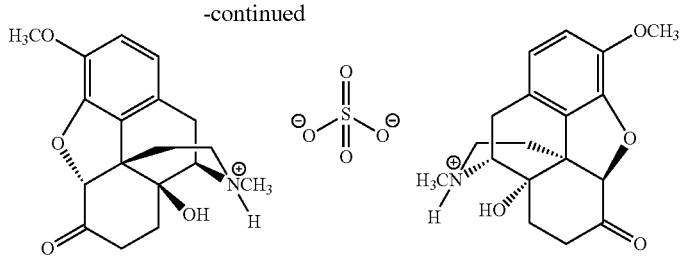

Oxycodone Sulfate

+

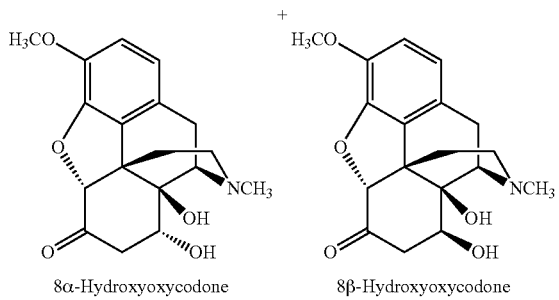

8α-Hydroxyoxycodone     8β-Hydroxyoxycodone

+

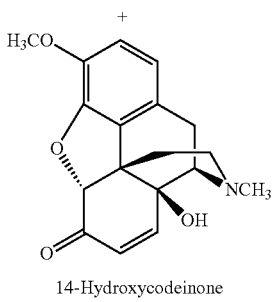

14-Hydroxycodeinone

1. Into a 300 mL hydrogenation vessel equipped with a magnetic stir bar, 14-hydroxycodeinone sulfate (25.03 g, 33.65 mmol (calculated without water of crystallization and based on 97.19% HPLC area percent using the USP HPLC method of Example 1)), deionized water (60 mL), 1-methoxy-2-propanol (60 mL) and 5% palladium on carbon (0.125 g) were charged. The solids partially dissolved into solution. The 14-hydroxycodeinone sulfate contained 2999 ppm of 8α-hydroxyoxycodone and 3647 ppm of 8β-hydroxyoxycodone, based on HPLC area percent using the USP HPLC method of Example 1.

2. The vessel was sealed, stirred at 750 rpm and heated to 40° C.

3. The mixture was then hydrogenated at 60 psia (413.69 kPa) for 12 hours.

4. The reaction was vented, purged with nitrogen and cooled to 22° C. over 8 hours.

5. The reaction mixture was sampled for HPLC analysis, indicating some 14-hydroxycodeinone was still present in the mixture.

6. The vessel was sealed, stirred at 750 rpm and heated to 40° C.

7. The mixture was then hydrogenated at 60 psia (413.69 kPa) for 4 hours.

8. The reaction was vented, purged with nitrogen and cooled to 22° C.

9. The reaction mixture was filtered through filter paper to remove the palladium on carbon. The filtered palladium on carbon was rinsed with a 1:1 mixture of deionized water:1-methoxy-2-propanol (50 mL) and the resulting rinsing solution was combined with the filtrate.

10. After sitting at ambient temperature for 48 hours, cube shaped crystals formed in the filtrate.

11. The filtrate was then treated with 175 mL of tert-butyl methyl ether and 75 mL of acetone. The mixture was stirred at ambient temperature for 1 hour.

12. The mixture was then filtered using a Buchner funnel with Whatman #1 filter paper.

13. The solids were dried under vacuum on the Buchner funnel for 2 hours.

14. The filtrate was transferred to a round bottom flask and concentrated under reduced pressure. The concentrated material was dried under house vacuum, at ambient temperature for 16 hours.

15. The concentrated filtrate was treated with 1-methoxy-2-propanol (200 mL) and deionized water (30 mL). The resulting suspension was transferred to a jacketed reaction vessel, equipped with an overhead stirrer.

16. The suspension was heated to 70° C., while stirring at 350 rpm. After stirring for 30 minutes at 70° C., deionized water (10 mL) was added to the reaction mixture.

17. While stirring at 350 rpm, the suspension was further heated to 85° C. Deionized water (5 mL) was added. The solids completely dissolved into the solution.

18. The mixture was stirred an additional 30 minutes at 85° C., and then cooled to ambient temperature over 1.5 hours. Solids precipitated out of solution during this cooling step.

19. The suspension was further cooled to 5° C. over 30 minutes, and further stirred (350 rpm) at 5° C. for an additional hour.

20. The solids were filtered under vacuum using a Buchner funnel with Whatman #2 filter paper.

15. The solids were dried under vacuum on the Buchner funnel for 30 minutes, before being transferred to a drying oven and dried under vacuum to a constant weight.

16. Isolated: 3.66 g of solid (oxycodone sulfate) from the first filtration (5.02 mmol, 14.5% yield) with an HPLC area ratio of oxycodone:14-hydroxycodeinone:8α-hydroxyoxycodone:8β-hydroxyoxycodone of 69,802,100:1412 (20 ppm):9803 (140 ppm):3051 (44 ppm). In other words, the composition contained 99.58% of oxycodone, 20 ppm of 14-hydroxycodeinone, 140 ppm of 8α-hydroxyoxycodone and 44 ppm of 8β-hydroxyoxycodone, based on HPLC area percent using the USP HPLC method of Example 1.

17. Isolated: 15.56 g of solid (oxycodone sulfate) from the second filtration (21.3 mmol, 61.8% yield) with an HPLC area ratio of oxycodone:14-hydroxycodeinone:8α-hydroxyoxycodone:8β-hydroxyoxycodone of 48,066,531:13,746 (286 ppm):40,497 (843 ppm):23,431 (487 ppm). In other words, the composition contained 99.55% of oxycodone, 286 ppm of 14-hydroxycodeinone, 843 ppm of 8α-hydroxyoxycodone and 487 ppm of 8β-hydroxyoxycodone, based on HPLC area percent using the USP Oxycodone HPLC method of Example 1.

Example 6: Preparation of Oxycodone Sulfate

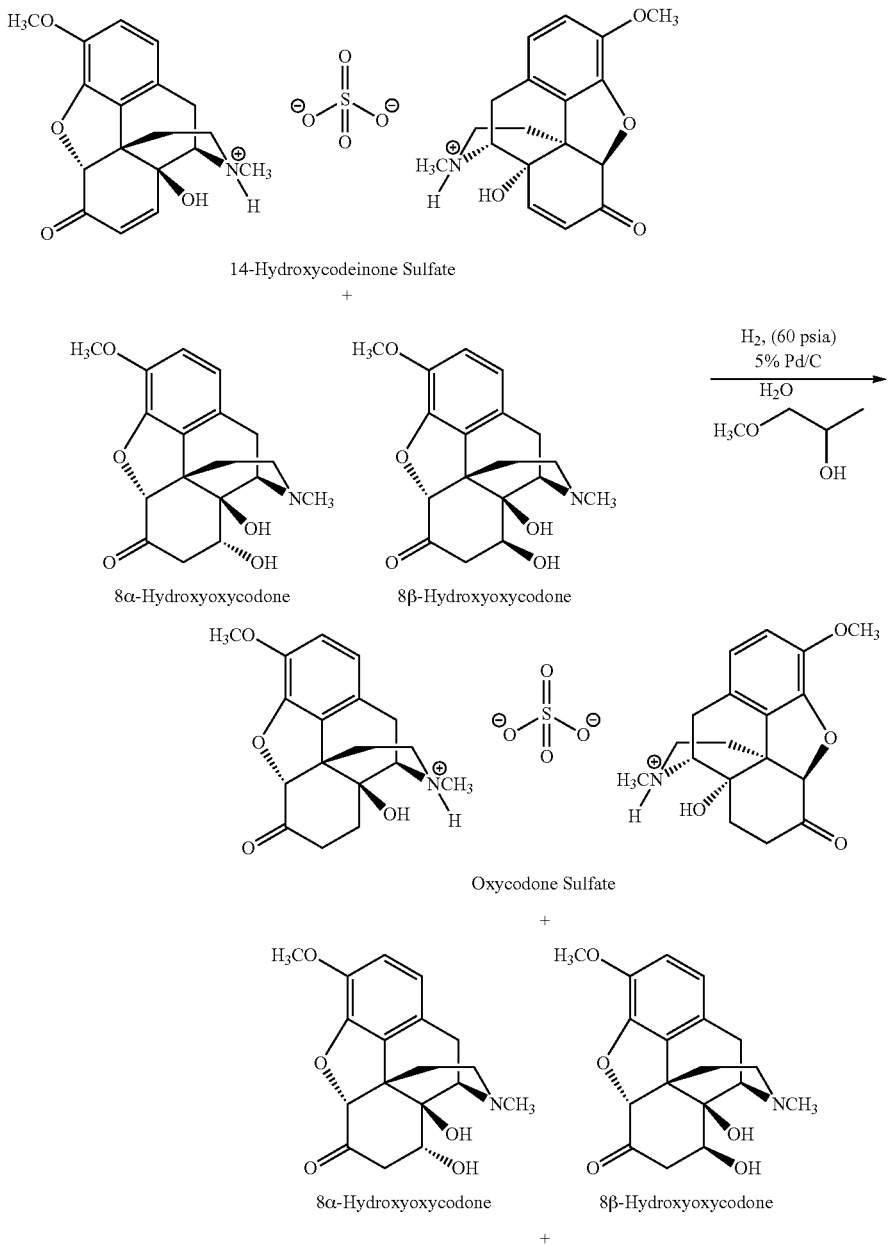

-continued

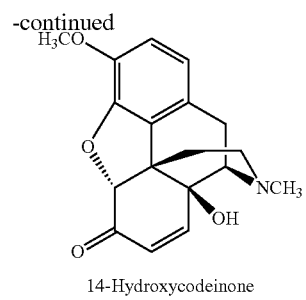

14-Hydroxycodeinone

1. Into a 80 mL hydrogenation vessel equipped with a magnetic stir bar, 14-hydroxycodeinone sulfate (7.68 g, 10.3 mmol (calculated without water of crystallization and based on 97.19% HPLC area percent using the USP HPLC method of Example 1)), deionized water (11 mL), 1-methoxy-2-propanol (21 mL) and 5% palladium on carbon (0.041 g) were charged. The solids partially dissolved into solution. The 14-hydroxycodeinone sulfate contained 2999 ppm of 8α-hydroxyoxycodone and 3647 ppm of 8β-hydroxyoxycodone, based on HPLC area percent using the USP HPLC method of Example 1.

2. The vessel was sealed, stirred at 750 rpm and heated to 40° C.

3. The mixture was then hydrogenated at 60 psia (413.69 kPa) for 16 hours.

4. The reaction was vented, purged with nitrogen and cooled to 22° C. The reaction mixture was left standing overnight at ambient temperature.

5. Solid material, in addition to the catalyst, was present in the reaction vessel after standing overnight.

6. The reaction mixture was diluted with 20 mL of deionized water and heated to 35° C., such that all of the solid material, aside from the catalyst, dissolved into solution.

8. The reaction mixture was filtered through three 5 μm (25 mm diameter) nylon filters to remove the palladium on carbon. The filtered palladium on carbon was rinsed with deionized water (10 mL) and the resulting rinsing solution was combined with the filtrate.

9. The filtrate was transferred to a round bottom flask and concentrated under reduced pressure to approximately 25% of the volume, using a rotovap at 60° C.

10. The concentrated material was transferred to an Erlenmeyer flask and treated with deionized water (10 mL) and 1-methoxy-2-propanol (7 mL).

11. As the solution cooled to ambient temperature over 1 hour, solids precipitated out of solution.

12. The solids were filtered under vacuum using a Buchner funnel with Whatman #1 filter paper and rinsed with 1-methoxy-2-propanol (2×25 mL).

15. The solids were dried under vacuum on the Buchner funnel for 1 hour, before being transferred to a drying oven and dried under vacuum to a constant weight.

16. Isolated: 3.59 g (4.93 mmol, 46% yield) of oxycodone sulfate as a white crystalline powder as analyzed by HPLC (USP Oxycodone HPLC method of Example 1). The HPLC area ratio of oxycodone:14-hydroxycodeinone:8α-hydroxyoxycodone:8β-hydroxyoxycodone was 31,744,691: 58,992 (1858 ppm):6418 (202 ppm):6784 (214 ppm). In other words, the composition contained 99.16% of oxycodone, 1858 ppm of 14-hydroxycodeinone, 202 ppm of 8α-hydroxyoxycodone and 214 ppm of 8β-hydroxyoxycodone, based on HPLC area percent.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

The invention claimed is:

1. A process for preparing isolated 14-hydroxycodeinone sulfate having formula

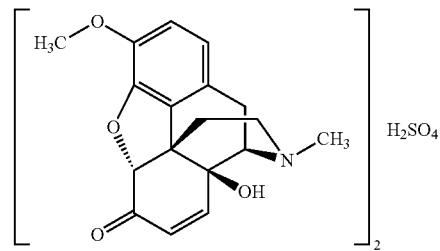

or a hydrate thereof, the process comprising:
(a) oxidizing thebaine, or a salt or solvate thereof, by reacting the thebaine with performic acid in an aqueous reaction mixture;
(b) adding sulfuric acid to the reaction mixture before or during the oxidation reaction, or both before and during the oxidation reaction,
(c) precipitating the 14-hydroxycodeinone sulfate or a hydrate thereof; and
(d) isolating the precipitate of the 14-hydroxycodeinone sulfate or a hydrate thereof from the reaction mixture to obtain isolated 14-hydroxycodeinone sulfate or a hydrate thereof.

2. The process of claim 1, wherein the 14-hydroxycodeinone sulfate is a hydrate of 14-hydroxycodeinone sulfate.

3. The process of claim 2, wherein the hydrate is a hydrate containing from 0.5 to 10.0 water molecules per molecule of the 14-hydroxycodeinone sulfate.

4. The process of claim 1, wherein the isolated precipitate is washed and/or (re)crystallized with a solvent which is suitable to remove from the precipitate a compound of the formula

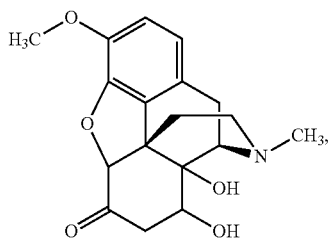 [SMILES: COc1ccc2c3c1OC1C(=O)CC(O)C4(O)[C@@H](C2)N(C)CC[C@]314]

or a salt or hydrate thereof.

5. The process of claim 4, wherein the solvent is selected from the group consisting of an ether, a ketone, an ester, an alcohol, water, an alkane (which may be halogenated), an aromatic solvent (which may be halogenated) and any combination of the foregoing.

6. The process of claim 1, wherein the performic acid is generated in situ in step (a) from hydrogen peroxide and formic acid.

7. The process of claim 1, wherein the performic acid is generated ex situ and then added to the reaction mixture.

8. The process of claim 1, wherein the sulfuric acid added in step (b) is added in an amount of from 0.1 to about 1.5 molar equivalents per molar equivalent of the thebaine.

9. The process of claim 8, wherein the sulfuric acid added in step (b) is added in an amount of from 0.51 to about 0.55 molar equivalents per molar equivalent of the thebaine.

10. The process of claim 1, wherein the total amount of acid in the reaction mixture, including the sulfuric acid and the formic acid used for generating the peracid, is from about 0.6 to about 14.0 molar equivalents of total acid per molar equivalent of the thebaine.

11. The process of claim 1, wherein the precipitation temperature is in a range of from about 5° C. to about 22° C., and the total amount of acid present in the reaction mixture is from about 1 to about 7 molar equivalents of total acid per molar equivalent of the thebaine.

12. The process of claim 2, wherein the hydrate is a monohydrate or dihydrate.

13. The process of claim 8, wherein the sulfuric acid added in step (b) is added in an amount of from about 0.4 to about 0.6 molar equivalents per molar equivalent of the thebaine.

14. A compound, which is a hydrate of isolated 14-hydroxycodeinone sulfate having formula

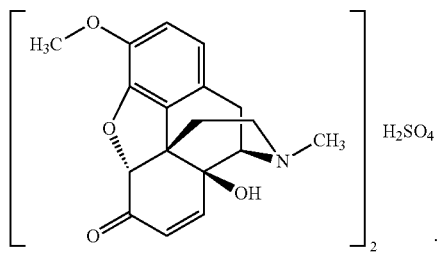

15. The compound of claim 14, which is a monohydrate or dihydrate.

16. Isolated 14-hydroxycodeinone sulfate hydrate prepared by the process according to claim 1.

17. A composition comprising the compound of claim 14.

18. The composition of claim 17, wherein the composition comprises 8-hydroxyoxycodone, or a salt or hydrate thereof, in an amount of less than about 1000 ppm of the 14-hydroxycodeinone sulfate (HPLC peak area ratio).

19. The process of claim 1, further comprising the steps of (e) providing a solution or suspension of the isolated 14-hydroxycodeinone sulfate or a hydrate thereof; and (f) reducing the 14-hydroxycodeinone present in the solution or suspension to obtain oxycodone, or a salt or hydrate thereof.

20. The process of claim 19, wherein the oxycodone is obtained in the form of oxycodone base.

21. The process of claim 19, wherein the oxycodone is prepared in the form of its salt or a hydrate thereof.

22. The process of claim 21, additionally comprising the step (g) isolating the oxycodone salt or the hydrate thereof.

23. The process of claim 22, wherein the salt is oxycodone sulfate or a hydrate thereof.

24. The process of claim 19, wherein the isolated 14-hydroxycodeinone sulfate or a hydrate thereof is dissolved or suspended in a solvent comprising methanol, tetrahydrofuran, isopropanol, acetone, ethanol, 1-methoxy-2-propanol, 2-ethoxyethanol, tert-amyl alcohol, isobutanol, 2-methyltetrahydrofuran, n-propanol, 1-butanol, 2-butanol, tert-butanol, isopropyl acetate, or di(ethylene glycol), or a mixture of any said solvent with water.

25. The process of claim 24, wherein the solvent further comprises an acid.

26. The process of claim 19, wherein the amount of 8-hydroxyoxycodone, or a salt or hydrate thereof, in the oxycodone or a salt or a hydrate thereof is less than about 1000 ppm of the oxycodone or a salt or hydrate thereof (HPLC peak ratio).

27. The process of claim 19, wherein the amount of 14-hydroxycodeinone, or a salt or hydrate thereof, in the oxycodone or a salt or hydrate thereof is less than about 500 ppm of the oxycodone or a salt or hydrate thereof (HPLC peak ratio).

28. The process of claim 23, wherein the isolated oxycodone sulfate or a hydrate thereof is further converted into another pharmaceutically acceptable salt or a hydrate thereof.

29. The process of claim 19, wherein the reduction reaction in step (f) is performed by hydrogenation.

* * * * *